US011186850B2

(12) United States Patent
Papapetridis et al.

(10) Patent No.: US 11,186,850 B2
(45) Date of Patent: *Nov. 30, 2021

(54) RECOMBINANT YEAST CELL

(71) Applicant: DSM IP ASSETS B.V., Heerlen (NL)

(72) Inventors: Ioannis Papapetridis, Delft (NL); Antonius Jeroen Adriaan Van Maris, Stockholm (SE); Jacobus Thomas Pronk, Delft (NL); Paulus Petrus De Waal, Echt (NL); Niels Lauret, Echt (NL); Maarten Dirk Verhoeven, Delft (NL); Jozef Petrus Johannes Schmitz, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/858,163

(22) Filed: Apr. 24, 2020

(65) Prior Publication Data

US 2020/0255871 A1 Aug. 13, 2020

Related U.S. Application Data

(63) Continuation of application No. 16/309,422, filed as application No. PCT/EP2017/064353 on Jun. 13, 2017, now Pat. No. 10,689,670.

(30) Foreign Application Priority Data

Jun. 14, 2016 (EP) ..................... 16174382

(51) Int. Cl.
| | | |
|---|---|---|
| C12P 7/06 | (2006.01) | |
| C12N 9/12 | (2006.01) | |
| C12N 9/88 | (2006.01) | |
| C12N 15/81 | (2006.01) | |
| C12N 1/14 | (2006.01) | |
| C12N 1/16 | (2006.01) | |
| C12R 1/645 | (2006.01) | |

(52) U.S. Cl.
CPC ............... *C12P 7/06* (2013.01); *C12N 1/145* (2021.05); *C12N 1/16* (2013.01); *C12N 9/1205* (2013.01); *C12N 9/88* (2013.01); *C12N 15/81* (2013.01); *C12R 2001/645* (2021.05); *C12Y 207/01019* (2013.01); *C12Y 401/01039* (2013.01); *Y02E 50/10* (2013.01)

(58) Field of Classification Search
CPC ........ C12N 15/81; C12N 9/1205; C12N 1/16; C12N 9/88; C12R 1/645; C12Y 207/01019; C12Y 401/01039; Y02E 50/10; C12P 7/06
See application file for complete search history.

(56) References Cited

U.S. PATENT DOCUMENTS

| | | |
|---|---|---|
| 6,265,186 B1 | 7/2001 | Swinkels et al. |
| 6,995,003 B1 | 2/2006 | Nieboer et al. |
| 9,303,253 B2 | 4/2016 | Van Maris et al. |
| 9,738,890 B2 | 8/2017 | Roubos et al. |
| 10,689,670 B2 * | 6/2020 | Papapetridis ......... C12N 15/81 |
| 2006/0127972 A1 | 6/2006 | Nieboer et al. |
| 2010/0086965 A1 | 4/2010 | Van Maris et al. |
| 2010/0248233 A1 | 9/2010 | Mueller et al. |
| 2014/0030730 A1 | 1/2014 | Mueller et al. |
| 2015/0299713 A1 | 10/2015 | Jiang et al. |
| 2017/0314011 A1 | 11/2017 | Roubos et al. |
| 2018/0010151 A1 | 1/2018 | Verwaal et al. |

FOREIGN PATENT DOCUMENTS

| | | |
|---|---|---|
| AU | 2014201742 A1 | 4/2014 |
| EP | 0481008 A1 | 4/1992 |
| EP | 0635574 A1 | 1/1995 |
| WO | 90/14423 A1 | 11/1990 |
| WO | 91/00920 A2 | 1/1991 |
| WO | 98/46772 A2 | 10/1998 |
| WO | 99/60102 A2 | 11/1999 |
| WO | 00/37671 A2 | 6/2000 |
| WO | 2008/041840 A1 | 4/2008 |
| WO | 2009/013159 A2 | 1/2009 |
| WO | 2013144257 A1 | 10/2013 |
| WO | 2014/033019 A1 | 3/2014 |
| WO | 2014/129898 A2 | 8/2014 |
| WO | 2015/107496 A1 | 7/2015 |
| WO | 2016/110512 A1 | 7/2016 |

OTHER PUBLICATIONS

Linde et al., Transcriptional regulation of YML083C under aerobic and anaerobic conditions. Yeast, 2003, vol. 20: 439-454. (Year: 2003).*

Verduyn, Cornelis et al., "Effect of Benzoic Acid on Metabolic Fluxes in Yeasts: A Continuous-Culture Study on the Regulation of Respiration and Alcoholic Fermentation", Yeast, 1992, pp. 501-517, vol. 8.

Guadalupe Medina, Victor et al., "Elimination of Glycerol Production in Anaerobic Cultures of a *Saccharomyces cerevisiae* Strain Engineered to Use Acetic Acid as an Electron Acceptor", Applied and Environmental Microbiology, Jan. 2010, pp. 190-195, vol. 76, No. 1.

Mans, Robert et al., "CRISPR/Cas9: a molecular Swiss army knife for simultaneous introduction of multiple genetic modifications in *Saccharomyces cerevisiae*", FEMS Yeast Research, 2015, pp. 1-15, vol. 15.

(Continued)

*Primary Examiner* — Ganapathirama Raghu
(74) *Attorney, Agent, or Firm* — McBee Moore & Vanik IP, LLC; Susan McBee; Chester Moore

(57) ABSTRACT

The present invention describes a recombinant yeast cell functionally expressing one or more heterologous nucleic acid sequences encoding for ribulose-1,5-phosphate carboxylase/oxygenase (EC4.1.1.39; Rubisco), and optionally one or more molecular chaperones for Rubisco, and one or more phosphoribulokinase (EC2.7.1.19; PRK), wherein the phosphoribulokinase is under control of a promoter (the "PRK promoter") that enables higher expression under anaerobic conditions than under aerobic conditions.

17 Claims, 6 Drawing Sheets

Specification includes a Sequence Listing.

(56) References Cited

OTHER PUBLICATIONS

Nijkamp, Jurgen F. et al., "De novo sequencing, assembly and analysis of the genome of the laboratory strain *Saccharomyces cerevisiae* CEN.PK113-7D, a model for modern industrial biotechnology", Microbial Cell Factories, 2012, pp. 1-16, vol. 11, No. 36.
Mikkelsen, Michael Dalgaard et al., "Microbial production of indolylglucosinolate through engineering of a multi-gene pathway in a versatile yeast expression platform", Metabolic Engineering, 2012, pp. 104-111, vol. 14.
DiCarlo, James E. et al., "Genome engineering in *Saccharomyces cerevisiae* using CRISPR-Cas systems", Nucleic Acids Research, 2013, pp. 4336-4343, vol. 41, No. 7.
Knijnenburg, Theo A. et al., "Combinatorial effects of environmental parameters on transcriptional regulation in *Saccharomyces cerevisiae*: A quantitative analysis of compendium of chemostat-based transcriptome data", BMC Genomics, Jan. 27, 2009, pp. 1-20, vol. 10, No. 53.
Mumberg, Dominik et al., "Yeast vectors for the controlled expression of heterologous proteins in different genetic backgrounds", Gene, 1995, pp. 119-122, vol. 156.
Gueldener, U. et al., "A second set of loxP marker cassettes for Cre-mediated multiple gene knockouts in budding yeast", Nucleic Acids Research, 2002, pp. 1-8, e23, vol. 30, No. 6.
Guadalupe-Medina, Victor et al., "Evolutionary engineering of a glycerol-3-phosphate dehydrogenase-negative, acetate-reducing *Saccharomyces cerevisiae* strain enables anaerobic growth at high glucose concentrations", Microbial Biotechnology, 2013, pp. 44-53, vol. 7.
Gietz, R. Daniel et al., "Transformation of Yeast by Lithium Acetate/Single-Stranded Carrier DNA/Polyethylene Glycol Method", Methods in Enzymology, 2002, pp. 87-96, vol. 350.
Solis-Escalante, Daniel et al., "amdSYM, a new dominant recyclable marker cassette for *Saccharomyces cerevisiae*", FEMS Yeast Res, 2013, pp. 126-139, vol. 13.
Papapetridis, Ioannis et al., "Improving ethanol yield in acetate-reducing *Saccharomyces cerevisiae* by cofactor engineering of 6-phosphogluconate dehydrogenase and deletion of ALD6", Microbial Cell Factories, 2016, pp. 1-16, vol. 15, No. 67.
Heijnen, J. J. et al., "In Search of a Thermodynamic Description of Biomass Yields for the Chemotrophic Growth of Microorganisms", Biotechnology and Bioengineering, 1992, pp. 833-858, vol. 39.
Postma, Erik et al., "Enzymic Analysis of the Crabtree Effect in Glucose-Limited Chemostat Cultures of *Saccharomyces cerevisiae*", Applied and Environmental Microbiology, Feb. 1989, pp. 468-477, vol. 55, No. 2.
Kwast, Kurt E. et al., "Genomic Analyses of Anaerobically Induced Genes in *Saccharomyces cerevisiae*: Functional Roles of Rox1 and Other Factors in Mediating the Anoxic Response", Journal of Bacteriology, Jan. 2002, pp. 250-265, vol. 184, No. 1.
Verduyn, Cornelis et al., "Physiology of *Saccharomyces cerevisiae* in anaerobic glucose-limited chemostat cultures", Journal of General Microbiology, 1990, pp. 395-403, vol. 136.
Keng, Teresa, "HAP1 and ROX1 Form a Regulatory Pathway in the Repression of HEM13 Transcription in *Saccharomyces cerevisiae*", Molecular and Cellular Biology, Jun. 1992, pp. 2616-2623, vol. 12, No. 6.
Zitomer, Richard S. et al., "Regulation of Gene Expression by Oxygen in *Saccharomyces cerevisiae*", Microbiological Reviews, Mar. 1992, p. 1-11, vol. 56, No. 1.
Entian, Karl-Dieter et al., "25 Yeast Genetic Strain and Plasmid Collections", Methods in Microbiology, 2007, pp. 630-666, vol. 36.
Zitomer, Richard S. et al., "Regulation of hypoxic gene expression in yeast", Kidney International, 1997, pp. 507-513, vol. 51.
Sertil, Odeniel et al., "The DAN1 gene of *S. cerevisiae* is regulated in parallel with the hypoxic genes, but by a different mechanism", Gene, 1997, pp. 199-205, vol. 192.
Ter Linde, Jose J.M. et al., "A microarray-assisted screen for potential Hap1 and Rox1 target genes in *Saccharomyces cerevisiae*", Yeast, 2002, pp. 825-840, vol. 19.
Yebenes, Hugo et al., "Chaperonins: two rings for folding", Trends in Biochemical Sciences, Aug. 2011, pp. 424-432, vol. 36, No. 8.
Horwich, Arthur L. et al., "Two Families of Chaperonin: Physiology and Mechanism", Annual Review of Cell and Developmental Biology, 2007, pp. 115-145, vol. 23.
Zeilstra-Ryalls, Jill et al., "The Universally Conserved GroE (Hsp60) Chaperonins", Annual Review of Microbiology, 1991, pp. 301-325, vol. 45.
Kadar, Zsofia et al., "Ethanol Fermentation of Various Pretreated and Hydrolyzed Substrates at Low Initial pH", Applied Biochemistry and Biotechnology, 2007, pp. 847-858, vol. 136-140.
Kuyper, Marko et al., "Evolutionary engineering of mixed-sugar utilization by a xylose-fermenting *Saccharomyces cerevisiae* strain", FEMS Yeast Research, 2005, pp. 925-934, vol. 5.
Luttik, Marijke et al., "The *Saccharomyces cerevisiae* ICL2 Gene Encodes a Mitochondrial 2-Methylisocitrate Lyase Involved in Propionyl-Coenzyme A Metabolism", Journal of Bacteriology, Dec. 2000, pp. 7007-7013, vol. 182, No. 24.
Guadalupe-Medina, Victor et al., "Carbon dioxide fixation by Calvin-Cycle enzymes improves ethanol yield in yeast", Biotechnology for Biofuels, 2013, pp. 1-12, vol. 6, No. 125.
Cohen, Brian D. et al., "Induction and repression of DAN1 and the family of anaerobic mannoprotein genes in *Saccharomyces cerevisiae* occurs through a complex array of regulatory sites", Nucleic Acids Research, 2001, pp. 799-808, vol. 29, No. 3.
International Search Report and Written Opinion of International Patent Application No. PCT/EP2017/064353 dated Sep. 7, 2017.
Broun et al., Catalytic plasticity of fatty acid modification enzymes underlying chemical diversity of plant lipids. Science, 1998, vol. 282: 1315-1317. (Year: 1998).
Devos et al.. Practical limits of function prediction. Proteins: Structure, Function, and Genetics. 2000, vol. 41: 98-107. (Year: 2000).
Seffernick et al., Melamine deaminase and Atrazine chlorohydrolase: 98 percent identical but functionally different. J. Bacteriol., 2001, vol. 183 (8): 2405-2410. (Year: 2001).
Whisstock et al., Prediction of protein function from protein sequence. Q. Rev. Biophysics., 2003, vol. 36 (3): 307-340. (Year: 2003).
Witkowski et al., Conversion of b-ketoacyl synthase to a Malonyl Decarboxylase by replacement of the active cysteine with glutamine. Biochemistry, 1999, vol. 38: 11643-11650. (Year: 1999).
Nissen, et al., "Anaerobic and aerobic batch cultivations of *Saccharomyces cerevisiae* mutants impaired in glycerol synthesis," Yeast, (2000), vol. 16: 463-474.
Labbe-Bois R. A. L. P., and P. Labbe. "Tetrapyrrole and heme biosynthesis in the yeast *Saccharomyces cerevisiae*." Biosynthesis of heme and chlorophylls, (1990): 235-285.

\* cited by examiner

RECOMBINANT YEAST CELL

CROSS-REFERENCE TO RELATED APPLICATIONS

This application is a Continuation of U.S. patent application Ser. No. 16/309,422, filed 12 Dec. 2018 (now U.S. Pat. No. 10,689,670), which is a National Stage entry of International Application No. PCT/EP2017/064353, filed 13 Jun. 2017, which claims priority to European Patent Application No. 16174382.8, filed 14 Jun. 2016. Each of these applications is incorporated by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2919208-485001_Sequence_Listing_ST25.txt" created on 14 Apr. 2020 and 52,492 bytes in size) is submitted concurrently with the instant application, and the entire contents of the Sequence Listing are incorporated herein by reference.

FIELD OF THE INVENTION

The invention relates to a recombinant yeast cell having the ability to produce a desired fermentation product, to the functional expression of heterologous peptides in a yeast cell, and to a method for producing a fermentation product wherein said yeast cell is used. The invention is further related to a use of $CO_2$ in the yeast cell.

BACKGROUND OF THE INVENTION

Microbial fermentation processes are applied to industrial production of a broad and rapidly expanding range of chemical compounds from renewable carbohydrate feedstocks. Especially in anaerobic fermentation processes, redox balancing of the cofactor couple $NADH/NAD^+$ can cause important constraints on product yields. This challenge is exemplified by the formation of glycerol as major by-product in the industrial production of—for instance— fuel ethanol by *Saccharomyces cerevisiae*, a direct consequence of the need to reoxidize NADH formed in biosynthetic reactions. Ethanol production by *Saccharomyces cerevisiae* is currently, by volume, the single largest fermentation process in industrial biotechnology, but various other compounds, including other alcohols, carboxylic acids, isoprenoids, amino acids etc, are also currently produced in industrial biotechnological processes. Various approaches have been proposed to improve the fermentative properties of organisms used in industrial biotechnology by genetic modification. A major challenge relating to the stoichiometry of yeast-based production of ethanol, but also of other compounds, is that substantial amounts of NADH-dependent side-products (in particular glycerol) are generally formed as a by-product, especially under anaerobic and oxygen-limited conditions or under conditions where respiration is otherwise constrained or absent. It has been estimated that, in typical industrial ethanol processes, up to about 4 wt. % of the sugar feedstock is converted into glycerol (Nissen et al. Yeast 16 (2000) 463-474). Under conditions that are ideal for anaerobic growth, the conversion into glycerol may even be higher, up to about 10%.

Glycerol production under anaerobic conditions is primarily linked to redox metabolism. During anaerobic growth of *S. cerevisiae*, sugar dissimilation occurs via alcoholic fermentation. In this process, the NADH formed in the glycolytic glyceraldehyde-3-phosphate dehydrogenase reaction is reoxidized by converting acetaldehyde, formed by decarboxylation of pyruvate to ethanol via $NAD^+$-dependent alcohol dehydrogenase. The fixed stoichiometry of this redox-neutral dissimilatory pathway causes problems when a net reduction of $NAD^+$ to NADH occurs elsewhere in metabolism. Under anaerobic conditions, NADH reoxidation in *S. cerevisiae* is strictly dependent on reduction of sugar to glycerol. Glycerol formation is initiated by reduction of the glycolytic intermediate dihydroxyacetone phosphate (DHAP) to glycerol 3-phosphate (glycerol-3P), a reaction catalyzed by $NAD^+$-dependent glycerol 3-phosphate dehydrogenase. Subsequently, the glycerol 3-phosphate formed in this reaction is hydrolysed by glycerol-3-phosphatase to yield glycerol and inorganic phosphate. Consequently, glycerol is a major by-product during anaerobic production of ethanol by *S. cerevisiae*, which is undesired as it reduces overall conversion of sugar to ethanol. Further, the presence of glycerol in effluents of ethanol production plants may impose costs for waste-water treatment. WO2014/129898 describes a recombinant cell functionally heterologous nucleic acid sequences encoding for ribulose-1,5-phosphate carboxylase/oxygenase (EC 4.1.1.39; herein abbreviated as "Rubisco"), and optionally molecular chaperones for Rubisco, and phosphoribulokinase (EC 2.7.1.19; herein abbreviated as "PRK"). WO2015107496 describes a recombinant cell functionally heterologous nucleic acid sequences encoding for ribulose-1,5-phosphate carboxylase/oxygenase units RbcL, RbcS and RcbX, molecular chaperones for Rubisco GroEL and GroES. In the examples PRK is expressed with a tetracyclin-iinducible promoter TetO7, see table 5. Thereby, a process aid is needed for this promoter i.e. the additions of a compound to the propagation which adds to the cost and complexity of the process. The said compound is doxycycline, an antibiotic, which is not preferred as an additive in the ethanol fermentation process. Although the described process in WO2014/129898 is advantageous, there is a continuing need for improvement, in particular improved production of a useful organic compound, such as ethanol. Also, it would be desirable to provide a microorganism wherein NADH-dependent side-products are further reduced. Also a process is desirable wherein no additives, such as antibiotic, are needed. Further, it is desirable that the propagation characteristics of the strain are improved. These are among objects of the invention.

SUMMARY OF THE INVENTION

One or more of the aforementioned objects is realized according to the present invention that provides a recombinant yeast cell functionally expressing one or more heterologous nucleic acid sequences encoding for ribulose-1,5-phosphate carboxylase/oxygenase (EC4.1.1.39; Rubisco), and optionally one or more molecular chaperones for Rubisco, and one or more phosphoribulokinase (EC2.7.1.19; PRK), wherein the phosphoribulokinase is under control of a promoter which has a PRK expression ratio $_{anaerobic/aerobic}$ of 2 or more. Advantageously, such recombinant yeast cell has improved product yields and/or reduced side-product formation and/or improved propagation characteristics and/ or absence of additives, such as antibiotic, to the fermentation process, so that the conventional fermentation process does not need to be changed.

TABLE 1

Description of the sequence listing

Figure 1:
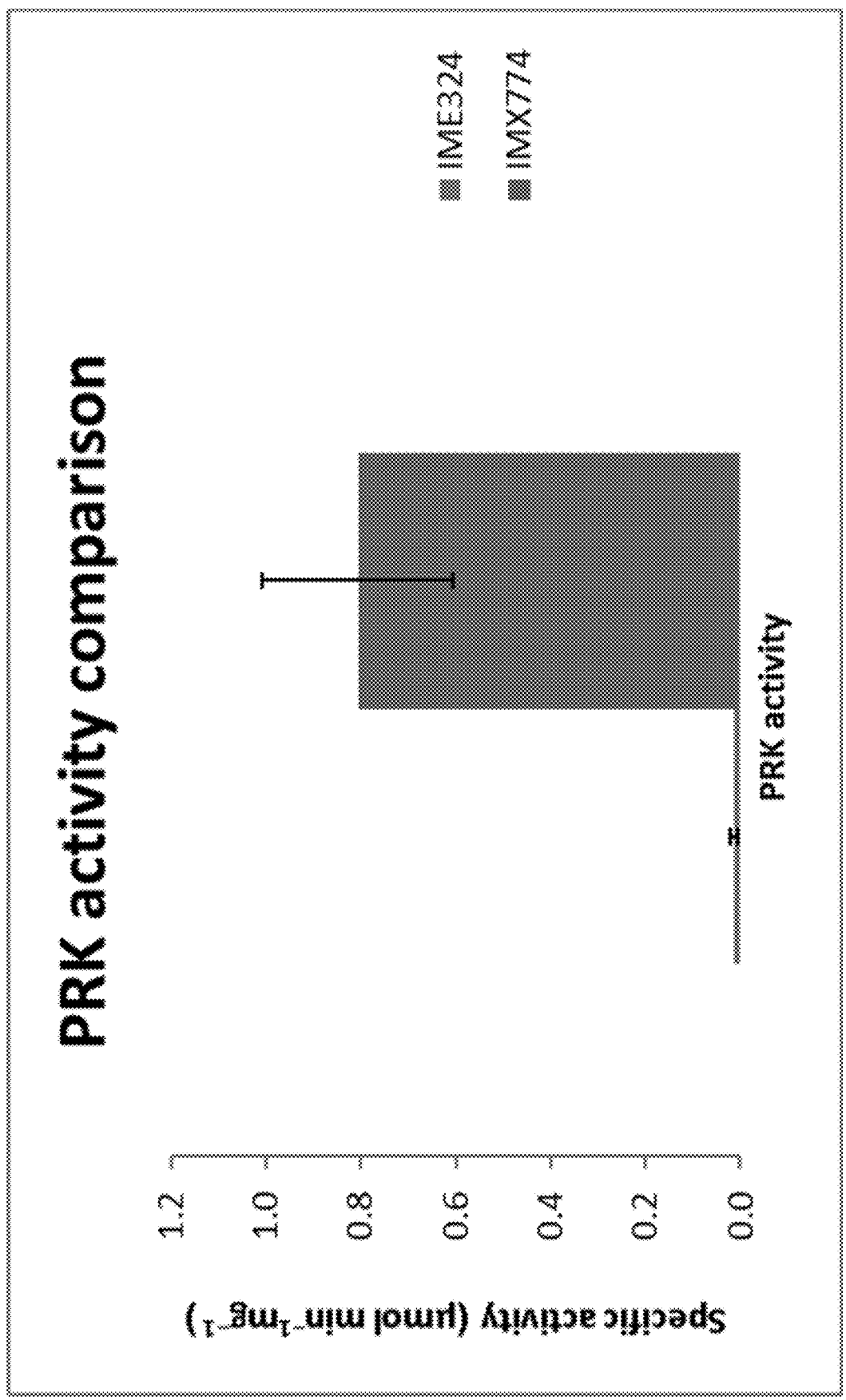
FIG. 1 PRK activity in cell-free extracts of IME324 (left in FIG. 1) and IMX774 (right in FIG. 1), harvested during exponential growth phase of anaerobic shake-flask cultures in synthetic medium (20 g L$^{-1}$ glucose). Values represent the averages and the standard deviations of activity when 30, 50 or 100 μl of cell-free extract were used. Data were collected from single cultures.

| SEQ ID NO: | Description | Purpose |
|---|---|---|
| 1 | | pUDR240 construction |
| 2 | | pUDR240 construction |
| 3 | | pUDR240 construction |
| 4 | | pUDR119 and pUDR164 construction |
| 5 | Plasmid construction | pUDR119 and pUDR164 construction |
| 6 | | pUDR119 and pUDR164 construction |
| 7 | | pUDR119 construction |
| 8 | | pUDR164 construction |
| 9 | | pUDR164 diagnostic PCR |
| 10 | | Addition of 20 bp primer-binding sequence to cbbM |
| 11 | | Addition of 20 bp primer-binding sequence to cbbM |
| 12 | | cbbM cassette construction - D tag addition (single copy cbbm-prk-chaperone integration) |
| 13 | | cbbM cassette construction - J tag addition (single copy cbbm-prk-chaperone integration) |
| 14 | | cbbM cassette construction - SGA1 tag addition |
| 15 | | cbbM cassette construction - G tag addition |
| 16 | | cbbM cassette construction - A tag addition |
| 17 | | cbbM cassette construction - G tag addition |
| 18 | | cbbM cassette construction - B tag addition |
| 19 | | cbbM cassette construction - A tag addition |
| 20 | cbbM cassettes construction | cbbM cassette construction - C tag addition |
| 21 | | cbbM cassette construction - B tag addition |
| 22 | | cbbM cassette construction - D tag addition |
| 23 | | cbbM cassette construction - C tag addition |
| 24 | | cbbM cassette construction - D tag addition |
| 25 | | cbbM cassette construction - M tag addition |
| 26 | | cbbM cassette construction - M tag addition |
| 27 | | cbbM cassette construction - N tag addition |
| 28 | | cbbM cassette construction - N tag addition |
| 29 | | cbbM cassette construction - O tag addition |
| 30 | | cbbM cassette construction - O tag addition |
| 31 | | Diagnostic primer cbbM integration |
| 32 | | Diagnostic primer cbbM integration |
| 33 | | Diagnostic primer cbbM integration |
| 34 | | Diagnostic primer cbbM integration |
| 35 | | Diagnostic primer cbbM integration |
| 36 | | Diagnostic primer cbbM integration |
| 37 | | Diagnostic primer cbbM integration |
| 38 | | Diagnostic primer cbbM integration |
| 39 | | Diagnostic primer cbbM integration |
| 40 | | Diagnostic primer cbbM integration |
| 41 | | Diagnostic primer cbbM integration |
| 42 | cbbM integration diagnostic primers | Diagnostic primer cbbM integration |
| 43 | | Diagnostic primer cbbM integration |
| 44 | | Diagnostic primer cbbM integration |
| 45 | | Diagnostic primer cbbM integration |

TABLE 1-continued

| SEQ ID NO: | Description | Purpose |
|---|---|---|
| 46 | | Diagnostic primer cbbM integration |
| 47 | | Diagnostic primer cbbM integration |
| 48 | | Diagnostic primer cbbM integration |
| 49 | | Diagnostic primer cbbM integration |
| 50 | | Diagnostic primer cbbM integration |
| 51 | | Diagnostic primer cbbM integration |
| 52 | | Diagnostic primer cbbM integration |
| 53 | | Diagnostic primer cbbM integration |
| 54 | | Diagnostic primer cbbM integration |
| 55 | | groEL cassette construction - J tag addition |
| 56 | groES, groEL cassette construction | groEL cassette construction - H tag addition |
| 57 | | groES cassette construction - H tag addition |
| 58 | | groES cassette construction - SGA1 tag addition |
| 59 | | LYS1p prk cassette construction |
| 60 | | LYS1p prk cassette construction |
| 61 | | UBC6p prk cassette construction |
| 62 | | UBC6p prk cassette construction |
| 63 | | YEN1p prk cassette construction |
| 64 | | YEN1p prk cassette construction |
| 65 | | DAN1p prk cassette construction |
| 66 | | DAN1p prk cassette construction |
| 67 | prk cassettes construction | prk cassette construction (PGK1t) |
| 68 | | prk cassette construction (PGK1t) - D tag addition (single copy cbbm-prk-chaperone integration) |
| 69 | | prk cassette construction (PGK1t) - X-2 tag addition |
| 70 | | prk amplification (LYS1p cassette) |
| 71 | | prk amplification |
| 72 | | prk amplification (UBC6p cassette) |
| 73 | | prk amplification (YEN1p cassette) |
| 74 | | prk amplification (DAN1p cassette) |
| 75 | URA3 cassette construction | URA3 amplification - SGA1 tag addition (single copy cbbm-prk-chaperone integration) |
| 76 | | URA3 amplification - C tag addition (single copy cbbm-prk-chaperone integration) |
| 77 | | Diagnostic primer single copy cbbm-prk-chaperone integration |
| 78 | | Diagnostic primer single copy cbbm-prk-chaperone integration |
| 79 | Misc. diagnostic primers | Diagnostic primer prk integration in X-2 |
| 80 | | Diagnostic primer prk integration in X-2 |
| 81 | | Diagnostic primer prk integration in X-2 |
| 82 | | Diagnostic primer prk integration in X-2 |
| 83 | | Repair fragment GPD1 |
| 84 | | Repair fragment GPD1 |
| 85 | | Repair fragment GPD2 |
| 86 | IMX675 construction and verification | Repair fragment GPD2 |
| 87 | | Diagnostic primer GPD1 deletion |
| 88 | | Diagnostic primer GPD1 deletion |
| 89 | | Diagnostic primer GPD2 deletion |
| 90 | | Diagnostic primer GPD2 deletion |
| 91 | Promoter ANB1, *S. cervisiae* | |
| 92 | Promoter DAN1, *S. cerevisiae* | |
| 93 | Sc_DAN1 promoter | |
| 94 | Sc_DIP5 promoter | |
| 95 | Sc_TIR3 promoter | |
| 96 | Sc_TIR2 promoter | |
| 97 | Sc_HEM13 promoter | |
| 98 | Sc_YHK8 promoter | |
| 99 | Sc_FET4 promoter | |
| 100 | Sc_TIR4 promoter | |
| 101 | Sc_AAC3 promoter | |
| 102 | Sc_PGK1 terminator | |
| 103 | Oligononucleotide primer Fw-PRK (DBC-15631) | |
| 104 | Oligononucleotide primer Rv-PRK (DBC-15632) | |
| 105 | gBLOCK bearing sequence of SNR52p-gRNA.INT1-SUP4t | |
| 106 | pRN599 | |
| 107 | Forward primer INT1-5'flank (BOZ-783) | |

TABLE 1-continued

Description of the sequence listing

| SEQ ID NO: | Description | Purpose |
|---|---|---|
| 108 | reverse primer INT1-5 'flank with connector c (DBC-19944) | |
| 109 | forward primer connector c to amplify anaerobic promoter-PRK-PGK1 terminator expression cassette (DBC-5799) | |
| 110 | reverse primer connector d to amplify PRK expression cassette (DBC-5800) | |
| 111 | forward primer to amplify URA3 marker with flank connector d (DBC-19947) | |
| 112 | reverse primer to amplify URA3 locus with flank connector e (DBC-19949) | |
| 113 | forward primer INT1-3'flank with connectord (DBC-19946) | |
| 114 | reverse primer INT1-3 'flank (BoZ-788) | |
| 115 | forward primer on backbone pRN599 (DBC-13775) | |
| 116 | reverse primer on backbone pRN599 (DBC-13776) | |
| 117 | forward primer on gRNA cassette INT1 (DBC-13773) | |
| 118 | reverse primer on gRNA cassette INT1 (DBC-13774) | |
| 119 | forward primer 7933 YEN1p prk cassette construction | |

DETAILED DESCRIPTION OF THE INVENTION

The invention thus relates to a recombinant yeast cell functionally expressing one or more heterologous nucleic acid sequences encoding for ribulose-1,5-phosphate carboxylase/oxygenase (EC4.1.1.39; Rubisco), and optionally one or more molecular chaperones for Rubisco, and one or more phosphoribulokinase (EC2.7.1.19; PRK), wherein the phosphoribulokinase is under control of a promoter (herein "the PRK promoter") which has a PRK expression ratio $_{anaerobic/aerobic}$ of 2 or more.

In an embodiment, the PRK promoter comprises in its sequence one or more of the motif NNNATTGTTNNN (SEQ ID NO:120).

In an embodiment, the PRK promoter is the native promoter of a gene selected from the list consisting of: FET4 (FErrous Transport; YMR319C), ANB1 (ANaeroBically induced; YJR047C), YHK8 (YHR048W), DAN1 (Delayed ANaerobic; YJR150C), AAC3 (ADP/ATP Carrier; YBR085W), TIR2 (TIp1-Related; YOR010C), DIP5 (DIcarboxylic amino acid Permease; YPL265W), HEM13 (HEMe biosynthesis; YDR044W), YNR014W, YAR028W, FUN 57, COX5B (Cytochrome c OXidase; YIL111W), OYE2 (Old Yellow Enzyme; YHR179W), SUR2 (SUppressor of Rvs161 and rvs167 mutations; YDR297W), FRDS1 (Fumarate ReDuctase; YEL047C), PIS1 (Phosphatidyl Inositol Synthase; YPR113W), LAC1 (Longevity-Assurance gene Cognate (LAG1 Cognate); YKL008C), YGR035C, FRT2 (Functionally Related to TCP1;YAL028W), EUG1 (ER protein Unnecessary for Growth; YDR518W), HEM14 (HEMe biosynthesis; YER014W), ISU2 (IscU homolog; YOR226C), ERG26 (ERGosterol biosynthesis; YGL001C), MLO1 (Mitochondrially LOcalized protein; YMR252C), and SML1 (Suppressor of Mec1 Lethality; YML058W); in particular FET4, ANB1, YHR048W, DAN1, AAC3, TIR2, DIP5 and HEM13.

In an embodiment, the PRK promoter comprises in its sequence one or more of the motif:

TCGTTYAG (SEQ ID NO: 121)

and/or

AAAAATTGTTGA. (SEQ ID NO: 122)

In an embodiment, the PRK promoter is comprises in its sequence one or more sequence motif:

TCGTTYAG (SEQ ID NO: 121)

and/or

AAAAATTGTTG. (SEQ ID NO: 123)

In particular such PRK promoter is native promoter of a DAN (Delayed ANaerobic), TIR (TIp1-Related), or PAU (seriPAUperin family) gene. In an embodiment, the PRK promoter is the native promoter of a gene selected from the list consisting of: TIR2, DAN1, TIR4 (YOR009W), TIR3 (YIL011W), PAU7 (YAR020C), PAU5 (YFL020C), YLL064C, YGR294W, DAN3 (YBR301W; PAU24), YIL176C, YGL261C, YOL161C, PAU1 (YJL223C), PAU6 (YNR076W), DAN2 (YLR037C; PAU23), YDR542W, YIR041W, YKL224C, PAU3 (YCR104W), YLL025W, YOR394W, YHL046C, YMR325W, YAL068C, YPL282C, PAU2 (YEL049W), and PAU4 (YLR461W), in particular the PRK promoter is the native promoter of a gene selected from the list consisting of: TIR2, DAN1, TIR4, TIR3, PAU7, PAU5, YLL064C, YGR294W, DAN3, YIL176C, YGL261C, YOL161C, PAU1, PAU6, DAN2, YDR542W, YIR041W, YKL224C, PAU3, and YLL025W.

The PRK promoter has a PRK expression ratio $_{anaerobic/aerobic}$ of 2 or more, preferably of 3 or more, 4 or more, 5 or more, 6 or more, 7 or more, 8 or more, 9 or more, 10 or more, 20 or more or 50 or more. This is to say that the expression of PRK is at least a factor 2 higher under anaerobic conditions than under aerobic conditions.

"Expression" refers to the transcription of a gene into structural RNA (rRNA, tRNA) or messenger RNA (mRNA) with subsequent translation into a protein.

In an embodiment the PRK expression ratio is determined by measuring the amount of PRK protein of cells grown under aerobic and anaerobic conditions. The amount of PRK protein can be determined by proteomics, as shown in the Examples.

In another embodiment the level or PRK expression ratio is determined by measuring the PRK activity of cells grown under aerobic and anaerobic conditions, e.g. in a cell-free extract. Methods to measure PRK activity are for instance described in Example 1.

In yet another embodiment the level or PRK expression ratio is determined by measuring the transcription level (e.g. as amount of mRNA) of the PRK gene of cells grown under aerobic and anaerobic conditions. The skilled person knows how to determine translation levels using methods commonly known in the art, e.g. Q-PCR, real-time PCR, northern blot, RNA-seq.

As used herein "promoter" is a DNA sequence that directs the transcription of a (structural) gene, in particular one or more phosphoribulokinase gene. The promoter enables higher expression during anaerobic conditions than under aerobic conditions.

In an embodiment, the PRK promoter may be a synthetic oligonucleotide. It may be a product of artificial oligonucleotide synthesis. Artificial oligonucleotide synthesis is a method in synthetic biology that is used to create artificial oligonucleotides, such as genes, in the laboratory. Commercial gene synthesis services are now available from numerous companies worldwide, some of which have built their business model around this task. Current gene synthesis approaches are most often based on a combination of organic chemistry and molecular biological techniques and entire genes may be synthesized "de novo", without the need for precursor template DNA.

In an embodiment, the promoter is located in the 5'-region of a the PRK gene, In an embodiment it is located proximal to the transcriptional start site of PRK gene.

The invention further relates to a vector (as defined hereinafter) comprising PRK and a promoter which has a PRK expression ratio $_{anaerobic/aerobic}$ of 2 or more.

The invention further relates to a process for preparing an organic compound, in particular an alcohol, comprising converting a carbon source, in particular a carbohydrate or another organic carbon source using a yeast cell, thereby forming the organic compound, wherein the yeast cell is a yeast cell according to the invention.

The term "a" or "an" as used herein is defined as "at least one" unless specified otherwise.

When referring to a noun (e.g. a compound, an additive, etc.) in the singular, the plural is meant to be included. Thus, when referring to a specific moiety, e.g. "compound", this means "at least one" of that moiety, e.g. "at least one compound", unless specified otherwise. The term 'or' as used herein is to be understood as 'and/or'.

When referring to a compound of which several isomers exist (e.g. a D and an L enantiomer), the compound in principle includes all enantiomers, diastereomers and cis/trans isomers of that compound that may be used in the particular method of the invention; in particular when referring to such as compound, it includes the natural isomer(s).

The term 'fermentation', 'fermentative' and the like is used herein in a classical sense, i.e. to indicate that a process is or has been carried out under anaerobic conditions. Anaerobic conditions are herein defined as conditions without any oxygen or in which essentially no oxygen is consumed by the yeast cell, in particular a yeast cell, and usually corresponds to an oxygen consumption of less than 5 mmol/l·h, in particular to an oxygen consumption of less than 2.5 mmol/l·h, or less than 1 mmol/l·h. More preferably 0 mmol/L/h is consumed (i.e. oxygen consumption is not detectable. This usually corresponds to a dissolved oxygen concentration in the culture broth of less than 5% of air saturation, in particular to a dissolved oxygen concentration of less than 1% of air saturation, or less than 0.2% of air saturation.

The term "yeast" or "yeast cell" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well-known species.

The term "recombinant (cell)" or "recombinant microorganism" as used herein, refers to a strain (cell) containing nucleic acid which is the result of one or more genetic modifications using recombinant DNA technique(s) and/or another mutagenic technique(s). In particular a recombinant cell may comprise nucleic acid not present in a corresponding wild-type cell, which nucleic acid has been introduced into that strain (cell) using recombinant DNA techniques (a transgenic cell), or which nucleic acid not present in said wild-type is the result of one or more mutations—for example using recombinant DNA techniques or another mutagenesis technique such as UV-irradiation—in a nucleic acid sequence present in said wild-type (such as a gene encoding a wild-type polypeptide) or wherein the nucleic acid sequence of a gene has been modified to target the polypeptide product (encoding it) towards another cellular compartment. Further, the term "recombinant (cell)" in particular relates to a strain (cell) from which DNA sequences have been removed using recombinant DNA techniques.

The term "transgenic (yeast) cell" as used herein, refers to a strain (cell) containing nucleic acid not naturally occurring in that strain (cell) and which has been introduced into that strain (cell) using recombinant DNA techniques, i.e. a recombinant cell).

The term "mutated" as used herein regarding proteins or polypeptides means that at least one amino acid in the wild-type or naturally occurring protein or polypeptide sequence has been replaced with a different amino acid, inserted or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989). The term "mutated" as used herein regarding genes means that at least one nucleotide in the nucleic acid sequence of that gene or a regulatory sequence thereof, has been replaced with a different nucleotide, or has been deleted from the sequence via mutagenesis, resulting in the transcription of a protein sequence with a qualitatively of quantitatively altered function or the knock-out of that gene.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e. g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at chem.qmul.ac.uk/iubmb/enzyme. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found via ncbi.nlm.nih.gov, (as available on 14 Jun. 2016) unless specified otherwise.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

The term "functional homologue" (or in short "homologue") of a polypeptide having a specific sequence (e.g. SEQ ID NO: X), as used herein, refers to a polypeptide comprising said specific sequence with the proviso that one or more amino acids are substituted, deleted, added, and/or inserted, and which polypeptide has (qualitatively) the same enzymatic functionality for substrate conversion. This functionality may be tested by use of an assay system comprising a recombinant yeast cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity in the yeast cell is to be tested, and assessing whether said conversion occurs in said cells. Candidate homologues may be identified by using in silico similarity analyses. A detailed example of such an analysis is described in Example 2 of WO2009/013159. The skilled person will be able to derive there from how suitable candidate homologues may be found and, optionally upon codon(pair) optimization, will be able to test the required functionality of such candidate homologues using a suitable assay system as described above. A suitable homologue represents a polypeptide having an amino acid sequence similar to a specific polypeptide of more than 50%, preferably of 60% or more, in particular of at least 70%, more in particular of at least 80%, at least 90%, at least 95%, at least 97%, at least 98% or at least 99% and having the required enzymatic functionality. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, http://emboss.bioinformatics.nl). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labeled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. In an embodiment, conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. In an embodiment, conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in eukaryotic host cell systems such as yeast are well known to those of skill in the art. A polynucleotide comprising a nucleic acid sequence of a gene encoding an enzyme with a specific activity can be expressed in such a eukaryotic system. In some embodiments, transformed/transfected yeast cells may be employed as expression systems for the expression of the enzymes. Expression of heterologous proteins in yeast is well known. Sherman, F., et al., Methods in Yeast Genetics, Cold Spring Harbor Laboratory (1982) is a well-recognized work describing the various methods available to express proteins in yeast. Two widely utilized yeasts are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. In an embodiment there is no (external) inducer needed.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleic acid sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

By "host cell" is meant a cell which contains a vector and supports the replication and/or expression of the vector.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

The recombinant yeast cell is preferably selected from the group of Saccharomycetaceae, such as *Saccharomyces cerevisiae, Saccharomyces pastorianus, Saccharomyces beticus, Saccharomyces fermentati, Saccharomyces paradoxus, Saccharomyces uvarum* and *Saccharomyces bayanus*; *Schizosaccharomyces* such as *Schizosaccharomyces pombe, Schizosaccharomyces japonicus, Schizosaccharomyces octosporus* and *Schizosaccharomyces cryophilus*; *Torulaspora* such as *Torulaspora delbrueckii*; *Kluyveromyces* such as *Kluyveromyces marxianus*; *Pichia* such as *Pichia stipitis, Pichia pastoris* or *pichia angusta*, *Zygosaccharomyces* such as *Zygosaccharomyces bailii*; *Brettanomyces* such as *Brettanomyces intermedius, Brettanomyces bruxellensis, Brettanomyces anomalus, Brettanomyces custersianus, Brettanomyces naardenensis, Brettanomyces nanus, Dekkera Bruxellis* and *Dekkera anomala*; *Metschnikowia, Issatchenkia*, such as *Issatchenkia orientalis, Kloeckera* such as *Kloeckera apiculata; Aureobasisium* such as *Aureobasidium pullulans*.

In an embodiment, the yeast cell is selected from the group of Saccharomycetaceae. In particular, good results have been achieved with a *Saccharomyces cerevisiae* cell. It has been found possible to use such a cell according to the invention in a method for preparing an alcohol (ethanol) wherein the NADH-dependent side-product formation (glycerol) was reduced by about 90%, and wherein the yield of the desired product (ethanol) was increase by about 10%, compared to a similar cell without Rubisco and PRK.

The Rubisco may in principle be selected from eukaryotic and prokaryotic Rubiscos. The Rubisco is preferably from a non-phototrophic organism. In particular, the Rubisco may be from a chemolithoautotrophic microorganism. Good results have been achieved with a bacterial Rubisco. Preferably, the bacterial Rubisco originates from a *Thiobacillus*, in particular, *Thiobacillus denitrificans*, which is chemolithoautotrophic. The Rubisco may be a single-subunit Rubisco or a Rubisco having more than one subunit. In particular, good results have been achieved with a single-subunit Rubisco. In particular, good results have been achieved with a form-II Rubisco, more in particular CbbM. A suitable Rubisco in accordance with the invention is encoded by the cbbM gene from *Thiobacillus denitrificans*. An alternative to this Rubisco, is a functional homologue of this Rubisco, in particular such functional homologue comprising a sequence having at least 80%, 85%, 90% or 95% sequence identity with the cbbM gene from *Thiobacillus denitrificans*. Suitable natural Rubisco polypeptides are given in Table 2, with identity to the cbbM gene from *Thiobacillus denitrificans*.

TABLE 2

| Natural Rubisco polypeptides suitable for expression | | |
|---|---|---|
| Source | Accession no. | MAX ID (%) |
| *Thiobacillus denitrificans* | AAA99178.2 | 100 |
| *Sideroxydans lithotrophicus* ES-1 | YP_003522651.1 | 94 |
| *Thiothrix nivea* DSM 5205 | ZP_10101642.1 | 91 |
| *Halothiobacillus neapolitanus* c2 | YP_003262978.1 | 90 |
| *Acidithiobacillus ferrooxidans* ATCC 53993 | YP_002220242.1 | 88 |
| *Rhodoferax ferrireducens* T118 | YP_522655.1 | 86 |
| *Thiorhodococcus drewsii* AZ1 | ZP_08824342.1 | 85 |
| uncultured prokaryote | AGE14067.1 | 82 |

In accordance with the invention, the Rubisco is functionally expressed in the microorganism, at least during use in an industrial process for preparing a compound of interest.

To increase the likelihood that herein enzyme activity is expressed at sufficient levels and in active form in the transformed (recombinant) host cells of the invention, the nucleotide sequence encoding these enzymes, as well as the Rubisco enzyme and other enzymes of the invention (see below), are preferably adapted to optimise their codon usage to that of the host cell in question. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. In an embodiment, the sequences which have been codon optimised for expression in the fungal host cell in question such as e.g. *S. cerevisiae* cells.

Preferably the functionally expressed Rubisco has an activity, defined by the rate of ribulose-1,5-bisphosphate-dependent $^{14}$C-bicarbonate incorporation by cell extracts of at least 1 nmol·min$^{-1}$·(mg protein)$^{-1}$, in particular an activity of at least 2 nmol·min$^{-1}$·(mg protein)$^{-1}$, more in particular an activity of at least 4 nmol·min$^{-1}$·(mg protein)$^{-1}$. The upper limit for the activity is not critical. In practice, the activity may be about 200 nmol·min$^{-1}$·(mg protein)$^{-1}$ or less, in particular 25 nmol·min$^{-1}$·(mg protein)$^{-1}$, more in particular 15 nmol·min$^{-1}$·(mg protein)$^{-1}$ or less, e.g. about 10 nmol·min$^{-1}$·(mg protein)$^{-1}$ or less. The conditions for an assay for determining this Rubisco activity are as found in the Examples.

A functionally expressed phosphoribulokinase (PRK, (EC 2.7.1.19)) according to the invention is capable of catalyzing the chemical reaction:

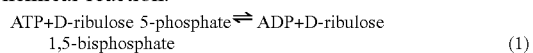
(1)

Thus, the two substrates of this enzyme are ATP and D-ribulose 5-phosphate; its two products are ADP and D-ribulose 1,5-bisphosphate.

PRK belongs to the family of transferases, specifically those transferring phosphorus-containing groups (phosphotransferases) with an alcohol group as acceptor. The systematic name of this enzyme class is ATP:D-ribulose-5-phosphate 1-phosphotransferase. Other names in common use include phosphopentokinase, ribulose-5-phosphate kinase, phosphopentokinase, phosphoribulokinase (phosphorylating), 5-phosphoribulose kinase, ribulose phosphate kinase, PKK, PRuK, and PRK. This enzyme participates in carbon fixation. The PRK can be from a prokaryote or a eukaryote. Good results have been achieved with a PRK originating from a eukaryote. Preferably the eukaryotic PRK originates from a plant selected from *Caryophyllales*, in particular from *Amaranthaceae*, more in particular from *Spinacia*. As an alternative to PRK from *Spinacia* a functional homologue of PRK from *Spinacia* may be present, in particular a functional homologue comprising a sequence having at least 70%, 75%, 80%. 85%, 90% or 95% sequence identity with the PRK from *Spinacia*. Suitable natural PRK polypeptides are given in Table 3.

TABLE 3

| Natural PRK polypeptides suitable for expression with identity to PRK from *Spinacia* | | |
|---|---|---|
| Source | Accession no. | MAX ID (%) |
| *Spinacia oleracea* | P09559.1 | 100 |
| *Medicago truncatula* | XP_003612664.1 | 88 |
| *Arabidopsis thaliana* | NP_174486.1 | 87 |
| *Vitis vinifera* | XP_002263724.1 | 86 |
| *Closterium peracerosum* | BAL03266.1 | 82 |
| *Zea mays* | NP_001148258.1 | 78 |

In an embodiment the recombinant microorganism further comprises a nucleic acid sequence encoding one or more heterologous prokaryotic or eukaryotic molecular chaperones, which—when expressed—are capable of functionally interacting with an enzyme in the microorganism, in particular with at least one of Rubisco and PRK.

Chaperonins are proteins that provide favourable conditions for the correct folding of other proteins, thus preventing aggregation. Newly made proteins usually must fold from a linear chain of amino acids into a three-dimensional form. Chaperonins belong to a large class of molecules that assist protein folding, called molecular chaperones. The energy to fold proteins is supplied by adenosine triphosphate (ATP). A review article about chaperones that is useful herein is written by Yébenes (2001); "Chaperonins: two rings for folding"; Hugo Yébenes et al. Trends in Biochemical Sciences, August 2011, Vol. 36, No. 8.

In an embodiment the chaperone or chaperones are from a bacterium, more preferably from *Escherichia*, in particular *E. coli* GroEL and GroEs from *E. coli* may in particular encoded in a microorganism according to the invention. In an embodiment, chaperones are chaperones from *Saccha-*

*romyces*, in particular *Saccharomyces cerevisiae* Hsp10 and Hsp60. If the chaperones are naturally expressed in an organelle such as a mitochondrion (examples are Hsp60 and Hsp10 of *Saccharomyces cerevisiae*) relocation to the cytosol can be achieved e.g. by modifying the native signal sequence of the chaperonins. In eukaryotes the proteins Hsp60 and Hsp10 are structurally and functionally nearly identical to GroEL and GroES, respectively. Thus, it is contemplated that Hsp60 and Hsp10 from any recombinant yeast cell may serve as a chaperone for the Rubisco. See Zeilstra-Ryalls J, Fayet O, Georgopoulos C (1991). "The universally conserved GroE (Hsp60) chaperonins". Annu Rev Microbiol. 45: 301-25. doi:10.1146/annurev. mi.45. 100191.001505. PMID 1683763 and Horwich A L, Fenton W A, Chapman E, Farr G W (2007). "Two Families of Chaperonin: Physiology and Mechanism". Annu Rev Cell Dev Biol. 23: 115-45. doi:10.1146/annurev.cellbio.23.090506.123555. PMID 17489689. Good results have been achieved with a recombinant yeast cell comprising both the heterologous chaperones GroEL and GroES. As an alternative to GroES a functional homologue of GroES may be present, in particular a functional homologue comprising a sequence having at least 70%, 75%, 80%, 85%, 90% or 95% sequence identity with GroES. Suitable natural chaperones polypeptide homologous to GroES are given in Table 4.

TABLE 4

Natural chaperones homologous to GroES polypeptides suitable for expression

>gi|115388105|ref|XP_001211558.1|:2-101 10 kDa heat shock protein, mitochondrial
[*Aspergillus terreus* NIH2624]
>gi|116196854|ref|XP_001224239.1|:1-102 conserved hypothetical protein
[*Chaetomium globosum* CBS 148.51]
>gi|119175741|ref|XP_001240050.1|:3-102 hypothetical protein CIMG_09671
[*Coccidioides immitis* RS]
>gi|119471607|ref|XP_001258195.1|:12-111 chaperonin, putative [*Neosartorya fischeri* NRRL181]
>gi|121699818|ref|XP_001268174.1|:8-106 chaperonin, putative [*Aspergillus clavatus* NRRL 1]
>gi|126274604|ref|XP_001387607.1|:2-102 predicted protein [*Scheffersomyces stipitis* CBS 6054]
>gi|146417701|ref|XP_001484818.1|:5-106 conserved hypothetical protein
[*Meyerozyma guilliermondii* ATCC 6260]
>gi|154303611|ref|XP_001552212.1|:1-102 10 kDa heat shock protein, mitochondrial
[*Botryotinia fuckeliana* B05.10]
>gi|156049571|ref|XP_001590752.1|:1-102 hypothetical protein SS1G_08492
[*Sclerotinia sclerotiorum* 1980]
>gi|156840987|ref|XP_001643870.1|:1-103 hypothetical protein Kpol_495p10
[*Vanderwaltozyma polyspora* DSM 70924]
>gi|169608295|ref|XP_001797567.1|:1-101 hypothetical protein SNOG_07218
[*Phaeosphaeria nodorum* SN15]
>gi|171688384|ref|XP_001909132.1|:1-102 hypothetical protein [*Podospora anserina* S mat+]
>gi|189189366|ref|XP_001931022.1|:71-168 10 kDa chaperonin [*Pyrenophora tritici-repentis* Pt-1C-BFP]
>gi|19075598|ref|NP_588098.1|:1-102 mitochondrial heat shock protein Hsp10 (predicted)
[*Schizosaccharomyces pombe* 972h-]
>gi|212530240|ref|XP_002145277.1|:3-100 chaperonin, putative
[*Talaromyces marneffei* ATCC 18224]
>gi|212530242|ref|XP_002145278.1|:3-95 chaperonin, putative
[*Talaromyces marneffei* ATCC 18224]
>gi|213404320|ref|XP_002172932.1|:1-102 mitochondrial heat shock protein Hsp10
[*Schizosaccharomyces japonicus* yFS275]
>gi|225557301|gb|EEH05587.1|:381-478 pre-mRNA polyadenylation factor fip1
[*Ajellomyces capsulatus* G186AR]
>gi|225684092|gb|EEH22376.1|:3-100 heat shock protein [*Paracoccidioides brasiliensis* Pb03]
>gi|238490530|ref|XP_002376502.1|:2-104 chaperonin, putative [*Aspergillus flavus* NRRL3357]
>gi|238878220|gb|EEQ41858.1|:1-106 10 kDa heat shock protein, mitochondrial
[*Candida albicans* WO-1]
>gi|240280207|gb|EER43711.1|:426-523 pre-mRNA polyadenylation factor fip1
[*Ajellomyces capsulatus* H143]
>gi|241950445|ref|XP_002417945.1|:1-103 10 kda chaperonin, putative; 10 kda heat shock protein mitochondrial (hsp10), putative [*Candida dubliniensis* CD36]
>gi|242819222|ref|XP_002487273.1|:90-182 chaperonin, putative [*Talaromyces stipitatus* ATC
>gi|254566327|ref|XP_002490274.1|:1-102 Putative protein of unknown function
[*Komagataella pastoris* GS115]
>gi|254577241|ref|XP_002494607.1|:1-103 ZYRO0A05434p [*Zygosaccharomyces rouxii*]
>gi|255717999|ref|XP_002555280.1|:1-103 KLTH0G05588p [*Lachancea thermotolerans*]
>gi|255956581|ref|XP_002569043.1|:2-101 Pc21g20560 [*Penicillium chrysogenum* Wisconsin 54-1255]
>gi|258572664|ref|XP_002545094.1|:16-108 chaperonin GroS [*Uncinocarpus reesii* 1704]
>gi|261190594|ref|XP_002621706.1|:3-100 chaperonin [*Ajellomyces dermatitidis* SLH14081]
>gi|295664909|ref|XP_002793006.1|:3-100 10 kDa heat shock protein, mitochondrial
[*Paracoccidioides* sp. 'lutzii' Pb01]
>gi|296412657|ref|XP_002836039.1|:76-177 hypothetical protein [*Tuber melanosporum* Mel28]
>gi|302307854|ref|NP_984626.2|:2-102 AEL235Wp [*Ashbya gossypii* ATCC 10895]
>gi|302894117|ref|XP_003045939.1|:1-102 predicted protein [*Nectria haematococca* mpVI 77-13-4]
>gi|303318351|ref|XP_003069175.1|:3-100 10 kDa heat shock protein, mitochondrial, putative
[*Coccidioides posadasii* C735 delta SOWgp]
>gi|310795300|gb|EFQ30761.1|:1-102 chaperonin 10 kDa subunit [*Glomerella graminicola* M1.001]
>gi|315053085|ref|XP_003175916.1|:12-109 chaperonin GroS [*Arthroderma gypseum* CBS 118893]
>gi|317032114|ref|XP_001394060.2|:334-433 heat shock protein [*Aspergillus niger* CBS 513.88]
>gi|317032116|ref|XP_001394059.2|:2-101 heat shock protein [*Aspergillus niger* CBS 513.88]
>gi|320583288|gb|EFW97503.1|:6-106 chaperonin, putative heat shock protein, putative
[*Ogataea parapolymorpha* DL-1]

TABLE 4-continued

Natural chaperones homologous to GroES polypeptides suitable for expression

>gi|320591507|gb|EFX03946.1|:1-102 heat shock protein [*Grosmannia clavigera* kw1407]
>gi|322700925|gb|EFY92677.1|:1-102 chaperonin [*Metarhizium acridum* CQMa 102]
>gi|325096696|gb|EGC50006.1|:409-506 pre-mRNA polyadenylation factor fip1
[*Ajellomyces capsulatus* H88]
>gi|326471604|gb|EGD95613.1|:14-111 chaperonin 10 Kd subunit
[*Trichophyton tonsurans* CBS112818]
>gi|327293056|ref|XP_003231225.1|:3-100 chaperonin [*Trichophyton rubrum* CBS 118892]
>gi|330942654|ref|XP_003306155.1|:37-136 hypothetical protein PTT_19211 [*Pyrenophora teres f. teres* 0-1]
>gi|336268042|ref|XP_003348786.1|:47-147 hypothetical protein SMAC_01809
[*Sordaria macrospora* khell]
>gi|340519582|gb|EGR49820.1|:1-109 predicted protein [*Trichoderma reesei* QM6a]
>gi|340960105|gb|EGS21286.1|:3-103 putative mitochondrial 10 kDa heat shock protein
[*Chaetomium thermophilum* var. *thermophilum* DSM 1495]
>gi|342883802|gb|EGU84224.1|:1-102 hypothetical protein FOXB_05181
[*Fusarium oxysporum* Fo5176]
>gi|344302342|gb|EGW32647.1|:2-102 hypothetical protein SPAPADRAFT_61712
[*Spathaspora passalidarum* NRRL Y-27907]
>gi|345570750|gb|EGX53571.1|:1-102 hypothetical protein AOL_s00006g437
[*Arthrobotrys oligospora* ATCC 24927]
>gi|346321154|gb|EGX90754.1|:1-102 chaperonin [*Cordyceps militaris* CM01]
>gi|346970393|gb|EGY13845.1|:1-102 heat shock protein [*Verticillium dahliae* VdLs.17]
>gi|354548296|emb|CCE45032.1|:1-106 hypothetical protein CPAR2_700360
[*Candida parapsilosis*]
>gi|358385052|gb|EHK22649.1|:1-102 hypothetical protein TRIVIDRAFT_230640
[*Trichoderma virens* Gv 29-8]
>gi|358393422|gb|EHK42823.1|:1-101 hypothetical protein TRIATDRAFT_258186
[*Trichoderma atroviride* IMI 206040]
>gi|361126733|gb|EHK98722.1|:1-97 putative 10 kDa heat shock protein, mitochondrial
[*Glarea lozoyensis* 74030]
>gi|363753862|ref|XP_003647147.1|:2-102 hypothetical protein Ecym_5593
[*Eremothecium cymbalariae* DBVPG#7215]
>gi|365758401|gb|EHN00244.1|:1-106 Hsp10p
[*Saccharomyces cerevisiae* × *Saccharomyces kudriavzevii* VIN7]
>gi|365987664|ref|XP_003670663.1|:1-103 hypothetical protein NDAI_0F01010
[*Naumovozyma dairenensis* CBS 421]
>gi|366995125|ref|XP_003677326.1|:1-103 hypothetical protein NCAS_0G00860
[*Naumovozyma castellii* CBS 4309]
>gi|366999797|ref|XP_003684634.1|:1-103 hypothetical protein TPHA_0C00430
[*Tetrapisispora phaffii* CBS 4417]
>gi|367009030|ref|XP_003679016.1|:1-103 hypothetical protein TDEL_0A04730
[*Torulaspora delbrueckii*]
>gi|367023138|ref|XP_003660854.1|:1-104 hypothetical protein MYCTH_59302
[*Myceliophthora thermophila* ATCC 42464]
>gi|367046344|ref|XP_003653552.1|:1-102 hypothetical protein THITE_2116070
[*Thielavia terrestris* NRRL8126]
>gi|378726440|gb|EHY52899.1|:9-109 chaperonin GroES [*Exophiala dermatitidis* NIH/UT8656]
>gi|380493977|emb|CCF33483.1|:1-102 chaperonin 10 kDa subunit [*Colletotrichum higginsianu*
>gi|385305728|gb|EIF49680.1|:1-102 10 kda heat shock mitochondrial
[*Dekkera bruxellensis* AWRI1499]
>gi|389628546|ref|XP_003711926.1|:1-102 hsp10-like protein [*Magnaporthe oryzae* 70-15]
>gi|396462608|ref|XP_003835915.1|:1-101 similar to 10 kDa heat shock protein
[*Leptosphaeria maculans* JN3]
>gi|398392541|ref|XP_003849730.1|:1-102 hypothetical protein MYCGRDRAFT_105721
[*Zymoseptoria tritici* IPO323]
>gi|400597723|gb|EJP65453.1|:24-124 chaperonin 10 kDa subunit
[*Beauveria bassiana* ARSEF 2860]
>gi|401623646|gb|EJS41738.1|:1-106 hsp10p [*Saccharomyces arboricola* H-6]
>gi|401842164|gb|EJT44422.1|:1-92 HSP10-like protein [*Saccharomyces kudriavzevii* IFO 1802]
>gi|402084027|gb|EJT79045.1|:1-102 hsp10-like protein [*Gaeumannomyces graminis* var. *triti*
>gi|403215209|emb|CCK69709.1|:1-104 hypothetical protein KNAG_0C06130
[*Kazachstania naganishii* CBS 8797]
>gi|406604629|emb|CCH43969.1|:4-100 hypothetical protein BN7_3524 [*Wickerhamomyces ciferrii*]
>gi|406867021|gb|EKD20060.1|:56-156 hypothetical protein MBM_02012
[*Marssonina brunnea* f. sp. 'multigermtubi' MB_m1]
>gi|407926227|gb|EKG19196.1|:74-174 GroES-like protein [*Macrophomina phaseolina* MS6]
>gi|408398157|gb|EKJ77291.1|:11-111 hypothetical protein FPSE_02566
[*Fusarium pseudograminearum* CS3096]
>gi|410082063|ref|XP_003958610.1|:1-103 hypothetical protein KAFR_0H00660
[*Kazachstania africana* CBS2517]
>gi|425777664|gb|EKV15823.1|:58-157 Chaperonin, putative [*Penicillium digitatum* Pd1]
>gi|440639680|gb|ELR09599.1|:1-102 chaperonin GroES [*Geomyces destructans* 20631-21]
>gi|444323906|ref|XP_004182593.1|:1-105 hypothetical protein TBLA_0J00760
[*Tetrapisisporablattae* CBS 6284]
>gi|448083208|ref|XP_004195335.1|:2-101 Piso0_005888 [*Millerozyma farinosa* CBS 7064]
>gi|448087837|ref|XP_004196425.1|:2-102 Piso0_005888 [*Millerozyma farinosa* CBS 7064]
>gi|448534948|ref|XP_003870866.1|:1-106 Hsp10 protein [*Candida orthopsilosis* Co 90-125]

TABLE 4-continued

Natural chaperones homologous to GroES polypeptides suitable for expression

>gi|449295977|gb|EMC91998.1|:1-102 hypothetical protein BAUCODRAFT_39148
[*Baudoinia compn*]
>gi|46123659|ref|XP_386383.1|:3-103 hypothetical protein FG06207.1 [*Gibberella zeae* PH-1]
>gi|50289455|ref|XP_447159.1|:1-103 hypothetical protein [*Candida glabrata* CBS 138]
>gi|50308731|ref|XP_454370.1|:1-103 hypothetical protein [*Kluyveromyces lactis* NRRL Y-1140]
>gi|50411066|ref|XP_457014.1|:1-106 DEHA2B01122p [*Debaryomyces hansenii* CBS767]
>gi|50545998|ref|XP_500536.1|:1-102 YALI0B05610p [*Yarrowia lipolytica*]
>gi|51013895|gb|AAT93241.1|:1-106 YOR020C [*Saccharomyces cerevisiae*]
>gi|6324594|ref|NP_014663.1|:1-106 Hsp10p [*Saccharomyces cerevisiae* S288c]
>gi|67523953|ref|XP_660036.1|:2-101 hypothetical protein AN2432.2
[*Aspergillus nidulans* FGSCA4]
>gi|70992219|ref|XP_750958.1|:12-106 chaperonin [*Aspergillus fumigatus* Af293]
>gi|85079266|ref|XP_956315.1|:1-104 hypothetical protein NCU04334 [*Neurospora crassa* OR74A]

As an alternative to GroEL a functional homologue of GroEL may be present, in particular a functional homologue comprising a sequence having at least 70%, 75%, 80%, 85%, 90% or 95% sequence identity with SEQUENCE of GroEL. Suitable natural chaperones polypeptides homologous to GroEL are given in Table 5.

TABLE 5

Natural chaperones homologous to GroEL polypeptides suitable for expression

>gi|115443330|ref|XP_001218472.1| heat shock protein 60, mitochondrial precursor
[*Aspergillus terreus* NIH2624]
>gi|114188341|gb|EAU30041.1| heat shock protein 60, mitochondrial precursor
[*Aspergillus terreus* NIH2624]
>gi|119480793|ref|XP_001260425.1| antigenic mitochondrial protein HSP60, putative
[*Neosartorya fischeri* NRRL 181] >gi|119408579|gb|EAW18528.1| antigenic mitochondrial
protein HSP60, putative [*Neosartorya fischeri* NRRL 181]
>gi|126138730|ref|XP_001385888.1| hypothetical protein PICST_90190
[*Scheffersomyces stipitis* CBS 6054] >gi|126093166|gb|ABN67859.1| mitochondrial groEL-type heat shock
protein [*Scheffersomyces stipitis* CBS 6054]
>gi|145246630|ref|XP_001395564.1| heat shock protein 60 [*Aspergillus niger* CBS 513.88]
>gi|134080285|emb|CAK46207.1| unnamed protein product [*Aspergillus niger*]
>gi|350636909|gb|EHA25267.1| hypothetical protein ASPNIDRAFT_54001
[*Aspergillus niger* ATCC 1015]
>gi|146413148|ref|XP_001482545.1| heat shock protein 60, mitochondrial precursor
[*Meyerozyma guilliermondii* ATCC 6260]
>gi|154277022|ref|XP_001539356.1| heat shock protein 60, mitochondrial precursor
[*Ajellomyces capsulatus* NAm1] >gi|150414429|gb|EDN09794.1| heat shock protein 60,
mitochondrial precursor [*Ajellomyces capsulatus* NAm1]
>gi|154303540|ref|XP_001552177.1| heat shock protein 60 [*Botryotinia fuckeliana* B05.10]
>gi|347840915|emb|CCD55487.1| similar to heat shock protein 60 [*Botryotinia fuckeliana*]
>gi|156063938|ref|XP_001597891.1| heat shock protein 60, mitochondrial precursor
[*Sclerotinia sclerotiorum* 1980] >gi|154697421|gb|EDN97159.1| heat shock protein 60,
mitochondrial precursor [*Sclerotinia sclerotiorum* 1980 UF-70]
>gi|156844469|ref|XP_001645297.1| hypothetical protein Kpol_1037p35
[*Vanderwaltozyma polyspora* DSM 70294] >gi|156115957|gb|EDO17439.1| hypothetical protein Kpol_1037p35
[*Vanderwaltozyma polyspora* DSM 70294]
>gi|16416029|emb|CAB91379.2| probable heat-shock protein hsp60 [*Neurospora crassa*]
>gi|350289516|gb|EGZ70741.1| putative heat-shock protein hsp60
[*Neurospora tetrasperma* FGSC 2509]
>gi|169626377|ref|XP_001806589.1| hypothetical protein SNOG_16475
[*Phaeosphaeria nodorum* SN15] >gi|111055053|gb|EAT76173.1| hypothetical protein SNOG_16475
[*Phaeosphaeria nodorum* SN15]
>gi|169783766|ref|XP_001826345.1| heat shock protein 60 [*Aspergillus oryzae* RIB40]
>gi|238493601|ref|XP_002378037.1| antigenic mitochondrial protein HSP60, putative
[*Aspergillus flavus* NRRL3357] >gi|83775089|dbj|BAE65212.1| unnamed protein product
[*Aspergillus oryzae* RIB40] >gi|220696531|gb|EED52873.1| antigenic mitochondrial protein
HSP60, putative [*Aspergillus flavus* NRRL3357] >gi|391869413|gb|EIT78611.1| chaperonin,
Cpn60/Hsp60p [*Aspergillus oryzae* 3.042]
>gi|189190432|ref|XP_001931555.1| heat shock protein 60, mitochondrial precursor
[*Pyrenophora tritici-repentis* Pt-1C-BFP] >gi|187973161|gb|EDU40660.1| heat shock protein
60, mitochondrial precursor [*Pyrenophora tritici-repentis* Pt-1C-BFP]
>gi|190348913|gb|EDK41467.2| heat shock protein 60, mitochondrial precursor
[*Meyerozyma guilliermondii* ATCC 6260]
>gi|225554633|gb|EEH02929.1| hsp60-like protein [*Ajellomyces capsulatus* G186AR]
>gi|238880068|gb|EEQ43706.1| heat shock protein 60, mitochondrial precursor
[*Candida albicans* WO-1]
>gi|239613490|gb|EEQ90477.1| chaperonin GroL [*Ajellomyces dermatitidis* ER-3]
>gi|240276977|gb|EER40487.1| hsp60-like protein [*Ajellomyces capsulatus* H143]
>gi|241958890|ref|XP_002422164.1| heat shock protein 60, mitochondrial precursor, putative
[*Candida dubliniensis* CD36] >gi|223645509|emb|CAX40168.1| heat shock protein 60,
mitochondrial precursor, putative [*Candida dubliniensis* CD36]

TABLE 5-continued

Natural chaperones homologous to GroEL polypeptides suitable for expression

>gi|254572906|ref|XP_002493562.1| Tetradecameric mitochondrial chaperonin
[*Komagataella pastoris* GS115] >gi|238033361|emb|CAY71383.1| Tetradecameric mitochondrial chaperonin
[*Komagataella pastoris* GS115]
>gi|254579947|ref|XP_002495959.1| ZYRO0C07106p [*Zygosaccharomyces rouxii*]
>gi|238938850|emb|CAR27026.1| ZYRO0C07106p [*Zygosaccharomyces rouxii*]
>gi|255712781|ref|XP_002552673.1| KLTH0C10428p [*Lachancea thermotolerans*]
>gi|238934052|emb|CAR22235.1| KLTH0C10428p [*Lachancea thermotolerans* CBS 6340]
>gi|255721795|ref|XP_002545832.1| heat shock protein 60, mitochondrial precursor
[*Candida tropicalis* MYA-3404] >gi|240136321|gb|EER35874.1| heat shock protein 60, mitochondrial
precursor [*Candida tropicalis* MYA-3404]
>gi|255941288|ref|XP_002561413.1| Pc16g11070 [*Penicillium chrysogenum* Wisconsin 54-
1255] >gi|211586036|emb|CAP93777.1| Pc16g11070 [*Penicillium chrysogenum* Wisconsin 54-1255]
>gi|259148241|emb|CAY81488.1| Hsp60p [*Saccharomyces cerevisiae* EC1118]
>gi|260950325|ref|XP_002619459.1| heat shock protein 60, mitochondrial precursor
[*Clavispora lusitaniae* ATCC 42720] >gi|238847031|gb|EEQ36495.1| heat shock protein 60,
mitochondrial precursor [*Clavispora lusitaniae* ATCC 42720]
>gi|261194577|ref|XP_002623693.1| chaperonin GroL [*Ajellomyces dermatitidis* SLH14081]
>gi|239588231|gb|EEQ70874.1| chaperonin GroL [*Ajellomyces dermatitidis* SLH14081]
>gi|327355067|gb|EGE83924.1| chaperonin GroL [*Ajellomyces dermatitidis* ATCC 18188]
>gi|296422271|ref|XP_002840685.1| hypothetical protein [*Tuber melanosporum* Mel28]
>gi|295636906|emb|CAZ84876.1| unnamed protein product [*Tuber melanosporum*]
>gi|296809035|ref|XP_002844856.1| heat shock protein 60 [*Arthroderma otae* CBS 113480]
>gi|238844339|gb|EEQ34001.1| heat shock protein 60 [*Arthroderma otae* CBS 113480]
>gi|302308696|ref|NP_985702.2| AFR155Wp [*Ashbya gossypii* ATCC 10895]
>gi|299790751|gb|AAS53526.2| AFR155Wp [*Ashbya gossypii* ATCC 10895]
>gi|374108933|gb|AEY97839.1| FAFR155Wp [*Ashbya gossypii* FDAG1]
>gi|302412525|ref|XP_003004095.1| heat shock protein [*Verticillium albo-atrum* VaMs.102]
>gi|261356671|gb|EEY19099.1| heat shock protein [*Verticillium albo-atrum* VaMs.102]
>gi|302505585|ref|XP_003014499.1| hypothetical protein ARB_07061
[*Arthroderma benhamiae* CBS 112371] >gi|291178320|gb|EFE34110.1| hypothetical protein ARB_07061
[*Arthroderma benhamiae* CBS 112371]
>gi|302656385|ref|XP_003019946.1| hypothetical protein TRV_05992
[*Trichophyton verrucosum* HKI 0517] >gi|291183723|gb|EFE39322.1| hypothetical protein TRV_05992
[*Trichophyton verrucosum* HKI 0517]
>gi|302915513|ref|XP_003051567.1| predicted protein [*Nectria haematococca* mpVI 77-13-4]
>gi|256732506|gb|EEU45854.1| predicted protein [*Nectria haematococca* mpVI 77-13-4]
>gi|310794550|gb|EFQ30011.1| chaperonin GroL [*Glomerella graminicola* M1.001]
>gi|315048491|ref|XP_003173620.1| chaperonin GroL [*Arthroderma gypseum* CBS 118893]
>gi|311341587|gb|EFR00790.1| chaperonin GroL [*Arthroderma gypseum* CBS 118893]
>gi|320580028|gb|EFW94251.1| Tetradecameric mitochondrial chaperonin
[*Ogataea parapolymorpha* DL-1]
>gi|320586014|gb|EFW98693.1| heat shock protein mitochondrial precursor
[*Grosmannia clavigera* kw1407]
>gi|322692465|gb|EFY84374.1| Heat shock protein 60 precursor (Antigen HIS-62)
[*Metarhizium acridum* CQMa 102]
>gi|322705285|gb|EFY96872.1| Heat shock protein 60 (Antigen HIS-62)
[*Metarhizium anisopliae* ARSEF 23]
>gi|323303806|gb|EGA57589.1| Hsp60p [*Saccharomyces cerevisiae* FostersB]
>gi|323307999|gb|EGA61254.1| Hsp60p [*Saccharomyces cerevisiae* FostersO]
>gi|323332364|gb|EGA73773.1| Hsp60p [*Saccharomyces cerevisiae* AWRI796]
>gi|326468648|gb|EGD92657.1| heat shock protein 60 [*Trichophyton tonsurans* CBS 112818]
>gi|326479866|gb|EGE03876.1| chaperonin GroL [*Trichophyton equinum* CBS 127.97]
>gi|330915493|ref|XP_003297052.1| hypothetical protein PTT_07333
[*Pyrenophora teres* f. *teres* 0-1] >gi|311330479|gb|EFQ94847.1|
hypothetical protein PTT_07333 [*Pyrenophora teres* f. *teres* 0-1]
>gi|336271815|ref|XP_003350665.1| hypothetical protein SMAC_02337
[*Sordaria macrospora* k-hell] >gi|380094827|emb|CCC07329.1| unnamed protein product
[*Sordaria macrospora* k-hell]
>gi|336468236|gb|EGO56399.1| hypothetical protein NEUTE1DRAFT_122948
[*Neurospora tetrasperma* FGSC 2508]
>gi|340522598|gb|EGR52831.1| hsp60 mitochondrial precursor-like protein
[*Trichoderma reesei* QM6a]
>gi|341038907|gb|EGS23899.1| mitochondrial heat shock protein 60-like protein
[*Chaetomium thermophilum* var. *thermophilum* DSM 1495]
>gi|342886297|gb|EGU86166.1| hypothetical protein FOXB_03302
[*Fusarium oxysporum* Fo5176]
>gi|344230084|gb|EGV61969.1| chaperonin GroL [*Candida tenuis* ATCC 10573]
>gi|344303739|gb|EGW33988.1| hypothetical protein SPAPADRAFT_59397
[*Spathaspora passalidarum* NRRL Y-27907]
>gi|345560428|gb|EGX43553.1| hypothetical protein AOL_s00215g289
[*Arthrobotrys oligospora* ATCC 24927]
>gi|346323592|gb|EGX93190.1| heat shock protein 60 (Antigen HIS-62)
[*Cordyceps militaris* CM01]
>gi|346975286|gb|EGY18738.1| heat shock protein [*Verticillium dahliae* VdLs.17]
>gi|354545932|emb|CCE42661.1| hypothetical protein CPAR2_203040 [*Candida parapsilosis*]
>gi|358369894|dbj|GAA86507.1| heat shock protein 60, mitochondrial precursor
[*Aspergillus kawachii* IFO 4308]

TABLE 5-continued

Natural chaperones homologous to GroEL polypeptides suitable for expression

>gi|358386867|gb|EHK24462.1| hypothetical protein TRIVIDRAFT_79041
[*Trichoderma virens* Gv29-8]
>gi|358399658|gb|EHK48995.1| hypothetical protein TRIATDRAFT_297734
[*Trichoderma atroviride* IMI 206040]
>gi|363750488|ref|XP_003645461.1| hypothetical protein Ecym_3140
[*Eremothecium cymbalariae* DBVPG#7215]
>gi|356889095|gb|AET38644.1| Hypothetical protein Ecym_3140
[*Eremothecium cymbalariae* DBVPG#7215]
>gi|365759369|gb|EHN01160.1| Hsp60p
[*Saccharomyces cerevisiae* × *Saccharomyces kudriavzevii* VIN7]
>gi|365764091|gb|EHN05616.1| Hsp60p
[*Saccharomyces cerevisiae* × *Saccharomyces kudriavzevii* VIN7]
>gi|365985626|ref|XP_003669645.1| hypothetical protein NDAI_0D00880
[*Naumovozyma dairenensis* CBS 421]
>gi|343768414|emb|CCD24402.1| hypothetical protein NDAI_0D00880
[*Naumovozyma dairenensis* CBS 421]
>gi|366995970|ref|XP_003677748.1| hypothetical protein NCAS_0H00890
[*Naumovozyma castellii* CBS 4309]
>gi|342303618|emb|CCC71399.1| hypothetical protein NCAS_0H00890
[*Naumovozyma castellii* CBS 4309]
>gi|367005154|ref|XP_003687309.1| hypothetical protein TPHA_0J00520
[*Tetrapisispora phaffii* CBS 4417] >gi|357525613|emb|CCE64875.1| hypothetical protein TPHA_0J00520
[*Tetrapisispora phaffii* CBS 4417]
>gi|367017005|ref|XP_003683001.1| hypothetical protein TDEL_0G04230
[*Torulaspora delbrueckii*] >gi|359750664|emb|CCE93790.1| hypothetical protein TDEL_0G04230
[*Torulaspora delbrueckii*]
>gi|367035486|ref|XP_003667025.1| hypothetical protein MYCTH_2097570
[*Myceliophthora thermophila* ATCC 42464]
>gi|347014298|gb|AEO61780.1| hypothetical protein MYCTH_2097570
[*Myceliophthora thermophila* ATCC 42464]
>gi|367055018|ref|XP_003657887.1| hypothetical protein THITE_127923
[*Thielavia terrestris* NRRL 8126] >gi|347005153|gb|AEO71551.1| hypothetical protein THITE_127923
[*Thielavia terrestris* NRRL 8126]
>gi|378728414|gb|EHY54873.1| heat shock protein 60 [*Exophiala dermatitidis* NIH/UT8656]
>gi|380494593|emb|CCF33032.1| heat shock protein 60 [*Colletotrichum higginsianum*]
>gi|385305893|gb|EIF49836.1| heat shock protein 60 [*Dekkera bruxellensis* AWRI1499]
>gi|389638386|ref|XP_003716826.1| heat shock protein 60 [*Magnaporthe oryzae* 70-15]
>gi|351642645|gb|EHA50507.1| heat shock protein 60 [*Magnaporthe oryzae* 70-15]
>gi|440474658|gb|ELQ43388.1| heat shock protein 60 [*Magnaporthe oryzae* Y34]
>gi|440480475|gb|ELQ61135.1| heat shock protein 60 [*Magnaporthe oryzae* P131]
>gi|393243142|gb|EJD50658.1| chaperonin GroL [*Auricularia delicata* TFB-10046 SS5]
>gi|396494741|ref|XP_003844378.1| similar to heat shock protein 60
[*Leptosphaeria maculans* JN3] >gi|312220958|emb|CBY00899.1| similar to heat shock protein 60
[*Leptosphaeria maculans* JN3]
>gi|398393428|ref|XP_003850173.1| chaperone ATPase HSP60 [*Zymoseptoria tritici* IPO323]
>gi|339470051|gb|EGP85149.1| hypothetical protein MYCGRDRAFT_75170
[*Zymoseptoria tritici* IPO323]
>gi|401624479|gb|EJS42535.1| hsp60p [*Saccharomyces arboricola* H-6]
>gi|401842294|gb|EJT44530.1| HSP60-like protein [*Saccharomyces kudriavzevii* IFO 1802]
>gi|402076594|gb|EJT72017.1| heat shock protein 60 [*Gaeumannomyces graminis* var. *tritici*
R3-111a-1]
>gi|403213867|emb|CCK68369.1| hypothetical protein KNAG_0A07160
[*Kazachstania naganishii* CBS 8797]
>gi|406606041|emb|CCH42514.1| Heat shock protein 60, mitochondrial
[*Wickerhamomyces ciferrii*]
>gi|406863285|gb|EKD16333.1| heat shock protein 60 [*Marssonina brunnea* f. sp.
'multigermtubi' MB_m1]
>gi|407922985|gb|EKG16075.1| Chaperonin Cpn60 [*Macrophomina phaseolina* MS6]
>gi|408399723|gb|EKJ78816.1| hypothetical protein FPSE_00959
[*Fusarium pseudograminearum* CS3096]
>gi|410083028|ref|XP_003959092.1| hypothetical protein KAFR_0I01760
[*Kazachstania africana* CBS 2517] >gi|372465682|emb|CCF59957.1| hypothetical protein KAFR_0I01760
[*Kazachstania africana* CBS 2517]
>gi|444315528|ref|XP_004178421.1| hypothetical protein TBLA_0B00580
[*Tetrapisispora blattae* CBS 6284] >gi|387511461|emb|CCH58902.1| hypothetical protein TBLA_0B00580
[*Tetrapisispora blattae* CBS 6284]
>gi|448090588|ref|XP_004197110.1| Piso0_004347 [*Millerozyma farinosa* CBS 7064]
>gi|448095015|ref|XP_004198141.1| Piso0_004347 [*Millerozyma farinosa* CBS 7064]
>gi|359378532|emb|CCE84791.1| Piso0_004347 [*Millerozyma farinosa* CBS 7064]
>gi|359379563|emb|CCE83760.1| Piso0_004347 [*Millerozyma farinosa* CBS 7064]
>gi|448526196|ref|XP_003869293.1| Hsp60 heat shock protein [*Candida orthopsilosis* Co 90-
125] >gi|380353646|emb|CCG23157.1| Hsp60 heat shock protein [*Candida orthopsilosis*]
>gi|46123737|ref|XP_386422.1| HS60_AJECA Heat shock protein 60, mitochondrial precursor
(Antigen HIS-62) [*Gibberella zeae* PH-1]
>gi|50292099|ref|XP_448482.1| hypothetical protein [*Candida glabrata* CBS 138]
>gi|49527794|emb|CAG61443.1| unnamed protein product [*Candida glabrata*]
>gi|50310975|ref|XP_455510.1| hypothetical protein [*Kluyveromyces lactis* NRRL Y-1140]
>gi|49644646|emb|CAG98218.1| KLLA0F09449p [*Kluyveromyces lactis*]

TABLE 5-continued

Natural chaperones homologous to GroEL polypeptides suitable for expression

>gi|50422027|ref|XP_459575.1| DEHA2E05808p [*Debaryomyces hansenii* CBS767]
>gi|49655243|emb|CAG87802.1| DEHA2E05808p [*Debaryomyces hansenii* CBS767]
>gi|50555023|ref|XP_504920.1| YALI0F02805p [*Yarrowia lipolytica*]
>gi|49650790|emb|CAG77725.1| YALI0F02805p [*Yarrowia lipolytica* CLIB122]
>gi|6323288|ref|NP_013360.1| Hsp60p [*Saccharomyces cerevisiae* S288c]
>gi|123579|sp|P19882.1|HSP60_YEAST RecName: Full = Heat shock protein 60, mitochondrial;
AltName: Full = CPN60; AltName: Full = P66; AltName: Full = Stimulator factor I 66 kDa
component; Flags: Precursor >gi|171720|gb|AAA34690.1| heat shock protein 60 (HSP60)
[*Saccharomyces cerevisiae*] >gi|577181|gb|AAB67380.1| Hsp60p: Heat shock protein 60
[*Saccharomyces cerevisiae*] >gi|151941093|gb|EDN59473.1| chaperonin
[*Saccharomyces cerevisiae* YJM789] >gi|190405319|gb|EDV08586.1| chaperonin
[*Saccharomyces cerevisiae* RM11-1a] >gi|207342889|gb|EDZ70518.1| YLR259Cp-like protein
[*Saccharomyces cerevisiae* AWRI1631] >gi|256271752|gb|EEU06789.1| Hsp60p
[*Saccharomyces cerevisiae* JAY291] >gi|285813676|tpg|DAA09572.1| TPA: chaperone ATPase HSP60
[*Saccharomyces cerevisiae* S288c] >gi|323353818|gb|EGA85673.1| Hsp60p
[*Saccharomyces cerevisiae* VL3] >gi|349579966|dbj|GAA25127.1| K7_Hsp60p
[*Saccharomyces cerevisiae* Kyokai no. 7] >gi|392297765|gb|EIW08864.1| Hsp60p
[*Saccharomyces cerevisiae* CEN.PK113-7D] >gi|226279|prf||1504305A mitochondrial assembly factor
>gi|68485963|ref|XP_713100.1| heat shock protein 60 [*Candida albicans* SC5314]
>gi|68486010|ref|XP_713077.1| heat shock protein 60 [*Candida albicans* SC5314]
>gi|6016258|sp|O74261.1|HSP60_CANAL RecName: Full = Heat shock protein 60,
mitochondrial; AltName: Full = 60 kDa chaperonin; AltName: Full = Protein Cpn60; Flags:
Precursor >gi|3552009|gb|AAC34885.1| heat shock protein 60 [*Candida albicans*]
>gi|46434552|gb|EAK93958.1| heat shock protein 60 [*Candida albicans* SC5314]
>gi|46434577|gb|EAK93982.1| heat shock protein 60 [*Candida albicans* SC5314]
>gi|71001164|ref|XP_755263.1| antigenic mitochondrial protein HSP60
[*Aspergillus fumigatus* Af293] >gi|66852901|gb|EAL93225.1| antigenic mitochondrial protein HSP60, putative
[*Aspergillus fumigatus* Af293] >gi|159129345|gb|EDP54459.1| antigenic mitochondrial protein
HSP60, putative [*Aspergillus fumigatus* A1163]
>gi|90970323|gb|ABE02805.1| heat shock protein 60 [*Rhizophagus intraradices*]

In an embodiment a 10 kDa chaperone from Table 4 is combined with a matching 60 kDa chaperone from Table 4 of the same organism genus or species for expression in the host. For instance: >gi|189189366|ref|XP_001931022.1|: 71-168 10 kDa chaperonin [Pyrenophora tritici-repentis] expressed together with matching >gi|189190432|ref|XP_001931555.1| heat shock protein 60, mitochondrial precursor [Pyrenophora tritici-repentis Pt-1C-BFP]. All other combinations from Table 4 and 5 similarly made with same organism source are also available to the skilled person for expression. Furthermore, one may combine a chaperone from Table 4 from one organism with a chaperone from Table 5 from another organism, or one may combine GroES with a chaperone from Table 4, or one may combine GroEL with a chaperone from Table 5. As follows from the above, the invention further relates to a method for preparing an organic compound comprising converting a carbon source, using a microorganism, thereby forming the organic compound. The method may be carried out under aerobic, oxygen-limited or anaerobic conditions.

The invention allows in particular a reduction in formation of an NADH dependent side-product, especially glycerol, by up to 100%, up to 99%, or up to 90%, compared to said production in a corresponding reference strain. The NADH dependent side-product formation is preferably reduced by more than 10% compared to the corresponding reference strain, in particular by at least 20%, more in particular by at least 50%. NADH dependent side-product production is preferably reduced by 10-100%, in particular by 20-95%, more in particular by 50-90%.

In an embodiment a fermentation process is provided, wherein Rubisco, or another enzyme capable of catalysing the formation of an organic compound from $CO_2$ (and another substrate) or another enzyme that catalyses the function of $CO_2$ as an electron acceptor, is used, and carbon dioxide is present in the gas mixture above the fermentation broth and/or dissolved in the fermentation broth. In a specific embodiment, the carbon dioxide or part thereof is formed in situ by the microorganism.

If desired, the method further comprises the step of adding external $CO_2$ to the reaction system, usually by aeration with $CO_2$ or a gas mixture containing $CO_2$, for instance a $CO_2$/nitrogen mixture. Adding external $CO_2$ in particular is used to (increase or) maintain the $CO_2$ within a desired concentration range, if no or insufficient $CO_2$ is formed in situ.

As a carbon source, in principle any carbon source that the microorganism can use as a substrate can be used. In particular an organic carbon source may be used, selected from the group of carbohydrates and lipids (including fatty acids). Suitable carbohydrates include monosaccharides, disaccharides, and hydrolysed polysaccharides (e.g. hydrolysed starches, lignocellulosic hydrolysates). Although a carboxylic acid may be present, it is not necessary to include a carboxylic acid such as acetic acid, as a carbon source.

As shown in the Examples below, the invention is in suitable for the production of an alcohol, notably ethanol. However, it is contemplated that the insight that $CO_2$ can be used as an electron acceptor in microorganisms that do not naturally allow this, has an industrial benefit for other biotechnological processes for the production of organic molecules, in particular organic molecules of a relatively low molecular weight, particularly organic molecules with a molecular weight below 1000 g/mol. The following items are mentioned herein as embodiments of the use of carbon dioxide as an electron acceptor in accordance with the invention.

Regarding the production of ethanol, details are found herein above, when describing the yeast cell comprising PRK and Rubisco and in the examples. The ethanol or another alcohol is preferably produced in a fermentative process.

For the production of several organic acids (carboxylates), e.g. citric acid, an aerobic process is useful. For citric acid production for instance *Aspergillus niger, Yarrowia lipolytica*, or another known citrate producing organism may be used.

An example of an organic acid that is preferably produced anaerobically is lactic acid. Various lactic acid producing bacterial strains and yeast strains that have been engineered for lactate production are generally known in the art. Other embodiments of the invention are now described in more detail.

In an embodiment the invention relates to the use of the recombinant yeast cell as described herein in fermentation in the biofuel industry. The recombinant yeast cell may contain genes of a pentose metabolic pathway non-native to the recombinant yeast cell and/or that allow the recombinant yeast cell to convert pentose(s). In one embodiment, the recombinant yeast cell may comprise one or two or more copies of one or more xylose isomerases and/or one or two or more copies of one or more xylose reductase and xylitol dehydrogenase genes, allowing the recombinant yeast cell to convert xylose. In an embodiment thereof, these genes may be integrated into the recombinant yeast cell genome. In another embodiment, the recombinant yeast cell comprises the genes araA, araB and araD. It is then able to ferment arabinose. In one embodiment of the invention the recombinant yeast cell comprises xy/A-gene, XYL1 gene and XYL2 gene and/or XKS1-gene, to allow the recombinant yeast cell to ferment xylose; deletion of the aldose reductase (GRE3) gene; and/or overexpression of GAL2 and/or deletion of GAL80. Thus though inclusion of the above genes, suitable pentose or other metabolic pathway(s) may be introduced in the recombinant yeast cell that were non-native in the (wild type) recombinant yeast cell. According to an embodiment, the following genes may be introduced in the recombinant yeast cell by introduction into a host cell:

1) a set consisting of PPP-genes TAL1, TKL1, RPE1 and RKI1, optionally under control of strong constitutive promoter;
2) a set consisting of a xy/A-gene under control of strong constitutive promoter;
3) a set comprising a XKS1-gene under control of strong constitutive promoter,
4) a set consisting of the genes araA, araB and araD under control of a strong constitutive promoter
5) deletion of an aldose reductase gene The above cells may be constructed using known recombinant expression techniques. The co-factor modification may be effected before, simultaneous or after any of the modifications 1) to 5). The recombinant yeast cell according to the invention may be subjected to evolutionary engineering to improve its properties. Evolutionary engineering processes are known processes. Evolutionary engineering is a process wherein industrially relevant phenotypes of a microorganism, herein the recombinant yeast cell, can be coupled to the specific growth rate and/or the affinity for a nutrient, by a process of rationally set-up natural selection. Evolutionary Engineering is for instance described in detail in Kuijper, M, et al, FEMS, Eukaryotic cell Research 5(2005) 925-934, WO2008/041840 and WO2009/112472. After the evolutionary engineering the resulting pentose fermenting recombinant yeast cell is isolated. The isolation may be executed in any known manner, e.g. by separation of cells from a recombinant yeast cell broth used in the evolutionary engineering, for instance by taking a cell sample or by filtration or centrifugation.

In an embodiment, the recombinant yeast cell is marker-free. As used herein, the term "marker" refers to a gene encoding a trait or a phenotype which permits the selection of, or the screening for, a host cell containing the marker. Marker-free means that markers are essentially absent in the recombinant yeast cell. Being marker-free is particularly advantageous when antibiotic markers have been used in construction of the recombinant yeast cell and are removed thereafter. Removal of markers may be done using any suitable prior art technique, e.g. intramolecular recombination.

In one embodiment, the industrial recombinant yeast cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

The recombinant yeast cell further may comprise those enzymatic activities required for conversion of pyruvate to a desired fermentation product, such as ethanol, butanol (e.g. n-butanol, 2-butanol and isobutanol), lactic acid, 3-hydroxypropionic acid, acrylic acid, acetic acid, succinic acid, citric acid, fumaric acid, malic acid, itaconic acid, an amino acid, 1,3- propane-diol, ethylene, glycerol, a ß-lactam antibiotic or a cephalosporin.

In an embodiment, the recombinant yeast cell is derived from an industrial recombinant yeast cell. An industrial cell and industrial recombinant yeast cell may be defined as follows. The living environments of (recombinant yeast cell) cells in industrial processes are significantly different from that in the laboratory. Industrial recombinant yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial recombinant yeast cell strains are generally more robust towards these changes in environmental conditions which may occur in the applications they are used, such as in the baking industry, brewing industry, wine making and the biofuel ethanol industry. In one embodiment, the industrial recombinant yeast cell is constructed on the basis of an industrial host cell, wherein the construction is conducted as described hereinafter. Examples of industrial yeast cell (*S. cerevisiae*) are Ethanol Red® (Fermentis) Fermiol® (DSM) and Thermosacc® (Lallemand).

The recombinant yeast cells according to the invention are preferably inhibitor tolerant, i.e. they can withstand common inhibitors at the level that they typically have with common pretreatment and hydrolysis conditions, so that the recombinant yeast cells can find broad application, i.e. it has high applicability for different feedstock, different pretreatment methods and different hydrolysis conditions. In an embodiment the recombinant yeast cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxy- methylfurfural. Examples or phenolic compounds are vannilin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions. For phenolics: several tens of milligrams per liter, up to a gram per liter, depending on the feedstock, the pretreatment and the hydrolysis conditions.

In an embodiment, the recombinant yeast cell is a cell that is naturally capable of alcoholic fermentation, preferably, anaerobic alcoholic fermentation. A recombinant yeast cell preferably has a high tolerance to ethanol, a high tolerance to low pH (i.e. capable of growth at a pH lower than about 5, about 4, about 3, or about 2.5) and towards organic and/or a high tolerance to elevated temperatures.

In an embodiment one or more genes of the non-oxidative branch of the pentose phosphate pathway of the recombinant yeast of the invention are overexpressed, and/or a glycerol-3-phosphate dehydrogenase (GPD) gene is deleted or disrupted. In another embodiment a glycerol-3-phosphate dehydrogenase (GPD) gene is deleted or disrupted. In yet another embodiment one or more genes of the non-oxidative branch of the pentose phosphate pathway of the recombinant yeast of the invention are overexpressed and a glycerol-3-phosphate dehydrogenase (GPD) gene is deleted or disrupted. The GPD gene may be a GPD1 and/or a GPD2 gene. Both GPD1 and GPD2 genes may be deleted or disrupted, although it is preferred that GPD2, but not GPD1 is deleted or disrupted. The GPD gene encodes for an enzyme having at least EC number 1.1.1.8. WO2011/010923 describes methods to delete or disrupt a glycerol-3-phosphate dehydrogenase. In an embodiment the one or more genes of the pentose phosphate pathway that is overexpressed encodes for an enzyme selected from the list of a transaldolase (EC 2.2.1.2), a transketolase (EC 2.2.1.1), a ribose-5-phosphate isomerase (EC 5.3.1.6) and a D-ribulose-5-phosphate 3-epimerase (EC 5.1.3.1). In another embodiment the one or more genes of the pentose phosphate pathway that is overexpressed is selected from the list of TAL1, TAL2, NQM1, TKL1, TKL2, RPE1 and RKI1.

The invention also relates to a process for the fermentation of a substrate to produce a fermentation product with a recombinant yeast cell as described herein, in the biofuel industry, wherein the glycerol yield is at least 5%, at least 10% or at least 10%, at least 20% or at least 30% lower than that of a process with the corresponding wild-type recombinant yeast cell. In an embodiment of such process, the ethanol yield is not increased or decreased, compared to that of a process with the corresponding wild-type recombinant yeast cell.

Any of the above characteristics or activities of a recombinant yeast cell may be naturally present in the cell or may be introduced or modified by genetic modification.

Recombinant Expression

The recombinant yeast cell is a recombinant cell. That is to say, a recombinant yeast cell comprises, or is transformed with or is genetically modified with a nucleotide sequence that does not naturally occur in the cell in question. Techniques for the recombinant expression of enzymes in a cell, as well as for the additional genetic modifications of a recombinant yeast cell are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of fungal host cells are known from e.g. EP-A-0635574, WO98/46772, WO 99/60102, WO00/37671, WO90/14423, EP-A-0481008, EP-A-0635574 and U.S. Pat. No. 6,265,186.

Bioproducts Production

Over the years suggestions have been made for the introduction of various organisms for the production of bio-ethanol from crop sugars. In practice, however, all major bio-ethanol production processes have continued to use the recombinant yeast cells of the genus *Saccharomyces* as ethanol producer. This is due to the many attractive features of *Saccharomyces* species for industrial processes, i. e. a high acid-, ethanol tolerance and osmotolerance, capability of anaerobic growth, and of course its high alcoholic fermentative capacity. In an embodiment, recombinant yeast cell species as host cells include *S. cerevisiae, S. bulderi, S. barnetti, S. exiguus, S. uvarum, S. diastaticus, K. lactis, K. marxianus* or *K. fragilis*. A recombinant yeast cell may be a cell suitable for the production of ethanol. A recombinant yeast cell may, however, be suitable for the production of fermentation products other than ethanol. Such non-ethanolic fermentation products include in principle any bulk or fine chemical that is producible by a eukaryotic microorganism such as a recombinant yeast cell or a filamentous fungus.

In an embodiment, recombinant yeast cell for production of non-ethanolic fermentation products is a host cell that contains a genetic modification that results in decreased alcohol dehydrogenase activity.

Lignocellulose

Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. In addition, pectins and other pectic substances such as arabinans may make up considerably proportion of the dry mass of typically cell walls from non-woody plant tissues (about a quarter to half of dry mass may be pectins).

Pretreatment

Before enzymatic treatment, the lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Enzymatic Hydrolysis

The pretreated material is commonly subjected to enzymatic hydrolysis to release sugars that may be fermented according to the invention. This may be executed with conventional methods, e.g. contacting with cellulases, for instance cellobiohydrolase(s), endoglucanase(s), beta-glucosidase(s) and optionally other enzymes, The conversion with the cellulases may be executed at ambient temperatures or at higher temperatures, at a reaction time to release sufficient amounts of sugar(s). The result of the enzymatic hydrolysis is hydrolysis product comprising C5/C6 sugars, herein designated as the sugar composition.

The Sugar Composition

The sugar composition used according to the invention comprises glucose and one or more pentose, e.g. arabinose and/or xylose. Any sugar composition may be used in the invention that suffices those criteria. Optional sugars in the sugar composition are galactose and mannose. In an embodiment, the sugar composition is a hydrolysate of one or more lignocellulosic material. Lignocelllulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof. The conversion of glucose, xylose, arabinose and galactose to fermentation product is of great economic importance. Also mannose is present in some lignocellulose materials be it usually in lower amounts than the previously mentioned sugars. Advantageously therefore also mannose is converted by the recombinant yeast cell. It is expected that recombinant yeast cells of the present invention can be further manipulated to achieve other desirable characteristics, or even higher overall ethanol yields. Selection of improved recombinant yeast cells by passaging the recombinant yeast cells on medium containing hydrolysate has resulted in improved recombinant yeast cell with enhanced fermentation rates. Using the teachings of the present invention, one could readily such improved strains. By pentose-containing material, it is meant any medium comprising pentose, whether liquid or solid. Suitable pentose-containing materials include hydrolysates of polysaccharide or lignocellulosic biomass such as corn hulls, wood, paper, agricultural byproducts, and the like.

By a "hydrolysate" as used herein, it is meant a polysaccharide that has been depolymerized through the addition of water to form mono and oligosaccharide sugars. Hydrolysates may be produced by enzymatic or acid hydrolysis of the polysaccharide-containing material.

Preferably, the recombinant yeast cell is able to grow under conditions similar to those found in industrial sources of pentose. The method of the present invention would be most economical when the pentose-containing material can be inoculated with the recombinant yeast cell variant without excessive manipulation. By way of example, the pulping industry generates large amounts of cellulosic waste. Sacharification of the cellulose by acid hydrolysis yields hexoses and pentoses that can be used in fermentation reactions. However, the hydrolysate or sulfite liquor contains high concentrations of sulfite and phenolic inhibitors naturally present in the wood which inhibit or prevent the growth of most organisms. The examples below describe the fermentation of pentose in acid hydrolysates (or sulfite waste liquor) of hard woods and soft woods by the recombinant yeast cells of the present invention. It is reasonably expected that recombinant yeast cell strains capable of growing in sulfite waste liquor could grow be expected grow in virtually any other biomass hydrolysate.

Propagation

The invention further relates to a process for aerobic propagation of the recombinant yeast cell, in particular aerobic propagation of the recombinant yeast cell strain. Propagation is herein any process of recombinant yeast cell growth that leads to increase of an initial recombinant yeast cell population. Main purpose of propagation is to increase a recombinant yeast cell population using the recombinant yeast cell's natural reproduction capabilities as living organisms. There may be other reasons for propagation, for instance, in case dry recombinant yeast cell is used, propagation is used to rehydrate and condition the recombinant yeast cell, before it is grown. Fresh recombinant yeast cell, whether active dried recombinant yeast cell or wet cake may be added to start the propagation directly. The conditions of propagation are critical for optimal recombinant yeast cell production and subsequent fermentation, such as for example fermentation of lignocellulosic hydrolysate into ethanol. They include adequate carbon source, aeration, temperature and nutrient additions. Tank size for propagation and is normally between 2 percent and 5 percent of the (lignocellulosic hydrolysate to ethanol) fermentor size. In the propagation the recombinant yeast cell needs a source of carbon. The source of carbon may herein comprise glycerol, ethanol, acetate and/or sugars (C6 and C5 sugars). Other carbon sources may also be used. The carbon source is needed for cell wall biosynthesis and protein and energy production. Propagation is an aerobic process, thus the propagation tank must be properly aerated to maintain a certain level of dissolved oxygen. Adequate aeration is commonly achieved by air inductors installed on the piping going into the propagation tank that pull air into the propagation mix as the tank fills and during recirculation. The capacity for the propagation mix to retain dissolved oxygen is a function of the amount of air added and the consistency of the mix, which is why water is often added at a ratio of between 50:50 to 90:10 mash to water. "Thick" propagation mixes (80:20 mash-to-water ratio and higher) often require the addition of compressed air to make up for the lowered capacity for retaining dissolved oxygen. The amount of dissolved oxygen in the propagation mix is also a function of bubble size, so some ethanol plants add air through spargers that produce smaller bubbles compared to air inductors. Along with lower glucose, adequate aeration is important to promote aerobic respiration, which differs from the comparably anaerobic environment of fermentation. One sign of inadequate aeration or high glucose concentrations is increased ethanol production in the propagation tank. Generally during propagation, recombinant yeast cell requires a comfortable temperature for growth and metabolism, for instance the temperature in the propagation reactor is between 25-40° C. Generally lower temperatures result in slower metabolism and reduced reproduction, while higher temperatures can cause production of stress compounds and reduced reproduction. In an embodiment the propagation tanks are indoors and protected from the insult of high summer or low winter temperatures, so that maintaining optimum temperatures of between within the range of 30-35 degrees C. is usually not a problem. Further propagation may be conducted as propagation of recombinant yeast cell is normally conducted.

Fermentation

The invention provides a process for the fermentation of a recombinant yeast cell according to the invention e.g. ethanol, that is advantageous in the biofuel industry.

In an embodiment, the recombinant yeast cell according to the invention may be a pentose and glucose fermenting recombinant yeast cell, including but not limited to such cells that are capable of anaerobic simultaneous pentose and glucose consumption. In an embodiment of the process the pentose-containing material comprises a hydrolysate of ligno-cellulosic material. The hydrolysate may be an enzymatic hydrolysate of ligno-cellulosic material.

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$.

Thus, in an embodiment, anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, malic acid, fumaric acid, an amino acid and ethylene.

The fermentation process is preferably run at a temperature that is optimal for the cell. Thus, for most recombinant yeast cells, the fermentation process is performed at a temperature which is less than about 50° C., less than about 42° C., or less than about 38° C. For recombinant yeast cell or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also provides a process for producing a fermentation product. The fermentation process according to the present invention may be run under aerobic and anaerobic conditions. In an embodiment, the process is carried out under micro-aerophilic or oxygen limited conditions. An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

Preferably, in a process under oxygen-limited conditions, the rate of oxygen consumption is at least about 5.5, more preferably at least about 6, such as at least 7 mmol/L/h. A process of the invention may comprise recovery of the fermentation product. In an embodiment of the process, the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as recombinant yeast cells are well known in the art. The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more. According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 gl/L-200 g/L, 40 g/L-200 g/L, 50 g/L-200 g/L, 60 g/L-200 g/L, 70 g/L-200 g/L, 80 g/L-200 g/L, 90 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical maximum yield (Yps max in gr product per gram glucose). The theoretical maximum yield (Yps max in gr product per gram glucose) of a fermentation product can be derived from textbook biochemistry. For ethanol, 1 mole of glucose (180 gr) yields according to normal glycolysis fermentation pathway in recombinant yeast cell 2 moles of ethanol (=2×46=92 gr ethanol. The theoretical maximum yield of ethanol on glucose is therefore 92/180=0.511 gr ethanol/gr glucose). For n-butanol (MW 74 gr/mole) or iso butanol, the theoretical maximum yield is 1 mole of butanol per mole of glucose. So Yps max for (iso-)butanol=74/180=0.411 gr (iso-)butanol/gr glucose. For lactic acid the fermentation yield for homolactic fermentation is 2 moles of lactic acid (MW=90 gr/mole) per mole of glucose. According to this stoichiometry, the Yps max=1 gr lactic acid/gr glucose. Similar calculation may be made for C5/C6 fermentations, in which in addition to glucose also pentoses are included e.g. xylose and/or arabinose. For other fermentation products a similar calculation may be made.

SSF Mode

In SSF operation the product concentration is 25 g*Yps g/L /L or more, 30*Yps g/L or more, 35g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps gl/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L. Accordingly, the invention provides a method for the preparation of a fermentation product, which method comprises:

a. degrading lignocellulose using a method as described herein; and b. fermenting the resulting material, thereby to prepare a fermentation product.

Fermentation Product

The fermentation product of the invention may be any useful product. In one embodiment, it is a product selected from the group consisting of ethanol, n-butanol, 2-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase.

Recovery of the Fermentation Product

For the recovery of the fermentation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol. In an embodiment in addition to the recovery of fermentation product, the yeast may be recycled. The following non-limiting examples are intended to be purely illustrative.

EXAMPLES

Example 1: Expression of DAN1p-prk in a Rubisco Expressing Strain from the CEN.PK Lineage Maintenance of Strains Strains originating from the CEN.PK lineage were used in this example (Table 6) [1,2]. Cultures were propagated in synthetic medium [3], supplemented with 20 g $L^{-1}$ glucose. Propagation of *E. coli* DH5a stock cultures was performed in LB medium (5 g $L^{-1}$ Bacto yeast extract, 10 g $L^{-1}$ Bacto tryptone, 5 g $L^{-1}$ NaCl), supplemented with 100 µg $mL^{-1}$ ampicillin or 50 µg $mL^{-1}$ kanamycin. Frozen stocks were prepared by addition of glycerol (30% v/v final concentration) to growing cultures and subsequent storage at −80° C.

TABLE 6

*S. cerevisiae* strains used in this example.

| Strain name | Relevant Genotype | Origin |
| --- | --- | --- |
| CEN.PK113-5D | MATa ura3-52 | [1, 2] |
| IMX585 | MATa URA3 can1::cas9-natNT2 | [4] |
| IMX581 | MATa ura3-52 can1::cas9-natNT2 | [4] |
| IMX675 | MATa ura3-52 can1::cas9-natNT2 gpd1Δ gpd2Δ | Examples |
| IME324 | MATa ura3-52 can1::cas9-natNT2 p42G-TEF (empty) | Examples |
| IMX765 | MATa ura3-52 can1::cas9-natNT2 sga1:: cbbM (9 copies), groES, groEL | Examples |
| IMX773 | MATa ura3-52 can1::cas9-natNT2 sga1:: cbbM (9 copies), groES, groEL X-2::YEN1p-prk pUDR164 | Examples |
| IMX774 | MATa ura3-52 can1::cas9-natNT2 sga1:: cbbM (9 copies), groES, groEL X-2::DAN1p-prk pUDR164 | Examples |
| IMX1443 | IMX774 gpd2::RPE1, TKL1, TAL1, TAL2, RKI1, NQM1 | Examples |

Plasmid and Cassette Construction

A list of plasmids used in this example is given in Table 7. CRISPR/Cas9 genome editing was used to perform genetic modifications in all constructed strains [5]. Unique CRISPR/Cas9 sequences targeting GPD1, GPD2, SGA1 or X-2 were identified using a publicly available list [5]. For markerless deletion of GPD1 and GPD2, plasmid pUDR240 was constructed. The plasmid backbone was PCR amplified using primer combination 5793-5793 (double-binding) and pROS10 as template. The plasmid insert, containing the expression cassettes coding for the unique 20-bp gRNA sequences targeting GPD1 and GPD2, was obtained using primer combination 6965-6966 and plasmid pROS10 as template. For markerless genomic integration of gene cassettes, plasmids expressing unique gRNAs targeting the SGA1 locus or the intergenic region X-2 [6] were constructed. The plasmid backbones of puDR119 and pURD164 were obtained by PCR amplification using the primer combination 5792-5980 and plasmids pMEL11 and pMEL10, respectively, as templates. The plasmid inserts of pUDR119 and pUDR164, containing the expression cassettes coding for the unique 20-bp gRNA sequences targeting SGA1 and X-2 respectively, were obtained by PCR amplification using the primer combinations 5979-7023 for SGA1 and 5979-7374 for X-2 and plasmids pMEL11 and pMEL10, respectively, as templates. Phusion® Hot Start II High Fidelity DNA Polymerase (Thermo Scientific, Waltham, Mass., USA) was used for construction of plasmids and expression cassettes in all cases, according to the manufacturer's guidelines. The assembly of plasmids pUDR119, pUDR164 and pUDR240 was performed in vitro using the Gibson Assembly® Cloning kit (New England Biolabs, Ipswich, Mass., USA) following the supplier's guidelines. The assembly was enabled by homologous sequences present at the 5' and 3' ends of the PCR-amplified plasmid backbones and inserts. In each case, 1 ul of the Gibson-assembly mix was used for E. coli DH5a transformation by electroporation, performed in a Gene PulserXcell Electroporation System (Biorad, Hercules, Calif., USA). Correct assembly of plasmids was confirmed by diagnostic PCR (Dreamtaq®, Thermo Scientific) or restriction digestion. The constructed plasmids pUDR119, pUDR164 and pUDR240 were isolated from transformed E. coli cultures using a Sigma GenElute Plasmid kit (Sigma-Aldrich, St. Louis, Mo., USA) and used for transformation of S. cerevisiae.

A yeast expression cassette of cbbM was obtained by PCR amplification using plasmid pBTWW002 as template and primer combination 7549-7550. The resulting fragment was ligated to a pJET/1.2 blunt vector (Thermo-Scientific) following the supplier's protocol and cloned to E. coli. The resulting plasmid was used as PCR template to generate integration cbbM cassettes, using primer combinations 7074-7075 (integration at the SGA1 locus along with prk, groES, groEL), 7548-6285, 6280-6273, 6281-6270, 6282-6271, 6284-6272, 6283-6275, 6287-6276, 6288-6277, 6289-7075 (multiple-cbbM-copy integration at the SGA1 locus). The expression cassettes of cbbM were genetically identical, except for different overhangs present at the 5' and 3' ends of the fragments to allow for in vivo homologous recombination. Yeast expression cassettes of groEL and groES were obtained using plasmids pUD232 and pUD233 as templates and primer combinations 7076-7077 and 7078-7079 respectively. The genomic sequences corresponding to the constitutive promoters of LYS1, UBC6, YEN1 and the anaerobically active promoter of DAN1 [7] were obtained by PCR amplification with primer combinations 7082-7083, 7292-7294, 7293-7295 and 7930-7931 respectively, using genomic DNA of IMX585 as template. In the case of integration at the X-2 locus, primer combination 7933-7295 was used for amplification of the YEN1 promoter region. The terminator of PGK1 was obtained by PCR amplification with genomic DNA of IMX585 as template using primer combinations 7084-7085 (integration at the SGA1 locus along with cbbM, groES, groEL) and 7084-7934 (individual integration of prk at the X-2 locus). The ORF of prk was obtained by PCR amplification using primer combinations 7080-7081 (LYS1p cassette construction), 7296-7081 (UBC6p cassette construction), 7297-7081 (YEN1p cassette construction), 7932-7081 (DAN1p cassette construction) and plasmid pUDE046 as template. The various primer combinations resulted in prk-ORF fragments with homologous overhangs to the different promoter sequences and the terminator of PGK1. The expression cassettes LYS1p-prk-PGK1t, UBC6p-prk-PGK1t and YEN1p-prk-PGK1t were assembled in vitro using fusion PCR by combining the respective promoter/prk/PGK1t fragments as templates and primer combinations 7082-7085, 7292-7085 and 7293-7085 respectively, in the case of aimed integration at the SGA1 locus of strain IMX675 (along with a KlURA3 fragment, cbbM cassete and groEL, groES chaperones. When prk cassettes were integrated individually (integration at the X-2 locus), the complete expression cassettes (YEN1p-prk-PGK1t and DAN1p-prk-PGK1t) was assembled by in vivo homologous recombination after transformation to yeast and correct assembly was verified by diagnostic PCR. Primer combination 7086-7087 was used to obtain a KlURA3 fragment using plasmid pUG72 as template.

TABLE 7

Plasmids used in this example.

| Name | Characteristics | Origin |
| --- | --- | --- |
| p426-TEF | 2 μm ori, URA3, empty vector | [8] |
| pUG72 | KlURA3, PCR template | [9] |
| pMEL10 | 2 μm ori, URA3, SNR52p-gRNA.CAN1-SUP4t | [4] |
| pMEL11 | 2 μm ori, amdS, SNR52p-gRNA.CAN1-SUP4t | [4] |
| pROS10 | URA3, gRNA.CAN1-2 μm ori-gRNA.ADE2 | [4] |
| pUD232 | Delivery vector, TEF1p-groEL-ACT1t | [10] |
| pUD233 | Delivery vector, TPI1p-groES-PGI1t | [10] |
| pUDE046 | 2 μm ori, GAL1p-prk-CYC1t | [10] |
| pBTVWV002 | 2 μm ori, URA3, TDH3p-cbbM-CYC1t | [10] |
| pUDR119 | 2 μm ori, amdS, SNR52p-gRNA.SGA1-SUP4t | This example |
| pUDR164 | 2 μm ori, URA3, SNR52p-gRNA.X-2-SUP4t | This example |
| pUDR240 | URA3, gRNA.GPD1-2 μm ori-gRNA.GPD2 | This example |

Strain Construction

The lithium-acetate transformation protocol was used for yeast transformations [11]. Transformation mixtures were plated on synthetic medium agar plates [3] (2 Bacto Agar, BD, Franklin Lakes, N.J., USA), supplemented with 20 g $L^{-1}$ glucose in the case of transformations performed with puDR164 and pUDR240. In transformations performed with plasmid pUDR119, the agar plates were prepared as described previously [12]. For the construction of strain IMX765 uracil was additionally supplemented to the agar plates (150 mg $L^{-1}$) (Sigma-Aldrich). Confirmation of the desired genotypes in each case was performed by diagnostic colony PCR. Recycling of pUDR240 was performed using 5-fluoorotic acid (Zymo Research, Irvine, Calif., USA) counter-selection, following the supplier's guidelines. Recycling of pUDR119 was performed as described previously [12]. Strain IMX675 was constructed by co-transformation of the double-gRNA-expressing, GPD1/GPD2 targeting plasmid pUDR240 and the repair-oligonucleotide combinations 6967-6968 and 6969-6970 to the Cas9-expressing strain IMX581 (after plasmid recycling from the correct mutant). The expression cassettes LYS1p-prk-PGK1t, UBC6p-prk-PGK1t and YEN1p-prk-PGK1t were respectively co-transformed to strain IMX675 along with a single copy of the cbbM cassette, groEL, groES, the URA3 fragment and the gRNA-expressing, SGA1-targeting plasmid pUDR119. Overhangs present at the 5' and 3' ends of the molecules were designed to allow for complete assembly of the pathways in the SGA1 locus. Strain IMX765 was obtained by co-transformation of pUDR119, 9 copies of the expression cassette of cbbM and the expression cassettes of groEL and groES to IMX581 (after plasmid recycling from the correct mutant). Overhangs present at the 5' and 3' ends of the molecules allowed for in vivo assembly of the entire construct (11 fragments) and integration in the SGA1 locus. Strain IMX774 was obtained by transformation of strain IMX765 with the gRNA-expressing, X-2 targeting plasmid pUDR164 and the DAN1p, prk ORF, PGK1t fragments which were assembled in vivo into the complete construct and subsequently integrated in the X-2 locus. Strain IMX773 was obtained by transformation of strains IMX765 with pUDR164 and the YEN1p, prk ORF, PGK1t fragments which were similarly assembled in vivo and subsequently integrated in the X-2 locus. The control strain IME324 was obtained by transformation of IMX581 with the empty vector p 426-TEF.

Cultivation Media and Analytical Methods

Physiological characterization of S. cerevisiae strains was performed in anaerobic batch cultivations in 2-L bioreactors (Applikon, Delft, The Netherlands), with 1-L working volume. Salt solutions were sterilized by autoclaving at 120° C. for 20 min. Glucose solutions were autoclaved separately at 110° C. for 20 min and subsequently added to the sterile salt solutions. All fermentations were performed in synthetic medium [3] (20 g $L^{-1}$ glucose), supplemented with sterile solutions of the anaerobic growth factors ergosterol (10 mg $L^{-1}$) and Tween 80 (420 mg $L^{-1}$), as well as with 0.2 g $L^{-1}$ sterile antifoam C (Sigma-Aldrich). Anaerobic conditions were maintained by sparging of a gas mixture of $N_2/CO_2$ (90%/10%, <10 ppm oxygen) at a rate of 0.5 L $min^{-1}$ and culture pH was maintained at 5 by automatic addition of 2 M KOH. All cultivations were performed at a stirrer speed of 800 rpm and at a temperature of 30° C. Oxygen diffusion in the bioreactors was minimized by equipping them with Norprene tubing and Viton 0-rings. Pre-culture shake flask cultivations were performed aerobically in 500-mL flasks containing 100 mL synthetic medium (20 g $L^{-1}$ glucose). Initial flask pH was adjusted to 6 by addition of KOH. Cultures were grown at 30° C. and shaken at 200 rpm. In each case, pre-culture flasks were inoculated from frozen S. cerevisiae stock cultures. After incubation for 8-12 h, cultures from these flasks were used to inoculate fresh pre-culture flasks for bioreactor inoculum propagation. Bioreactors were inoculated to a starting OD660 of ca. 0.2. Off-gas analysis, biomass dry weight measurements, HPLC analysis of culture supernatants and correction for ethanol evaporation in bioreactor experiments were performed as described previously [13]. Optical density was determined at 660 nm, using a Libra S11 spectrophotometer (Biochrom, Cambridge, UK). Yields of products in each cultivation were calculated from samples taken at mid-exponential phase (minimum of five samples), as described previously [14]. For the calculation of the degree of reduction (electron) balances in performed fermentations, reported degree of reduction values for biomass, $CO_2$, $NH_4^+$ and extracellular metabolites (glucose, ethanol, glycerol, succinate, pyruvate, lactate, acetate) were used [15]. For determination of in vitro enzymatic activity of PRK, cells from exponentially growing, anaerobic shake-flask cultures in synthetic-medium were harvested and cell-free extracts were prepared as previously described [16]. The harvesting and sonification buffer contained 100 mM Tris-HCl, 20 mM $MgCl_2.6H_2O$ and 5 mM DTT (pH 8.2). The PRK assay contained 50 mM Tris-HCl (pH 8.2), 40 mM KCl, 10 mM $MgCl_{12}.6H_2O$, 0.15 mM NADH, 1 mM ATP, 3 mM phosphoenolpyruvate, 1 mM 1,4-dithiothreitol, 5 U of pyruvate kinase (EC 2.7.1.40), 6 U of L-lactate dehydrogenase (EC 1.1.1.27) and 30, 50 or 100 µl cell-free extract in 1 ml total volume. Reactions were started by addition of D-ribulose-5-phosphate (2.5 mM final concentration) and PRK activity was measured at 30° C. on a Hitachi 100-60 spectrophotometer by monitoring NADH oxidation at 340 nm over time. Protein content determination in cell-free extracts was performed as previously described (Lowrey protein assay) [17].

Physiological Characterization of Strains

Figure 2:
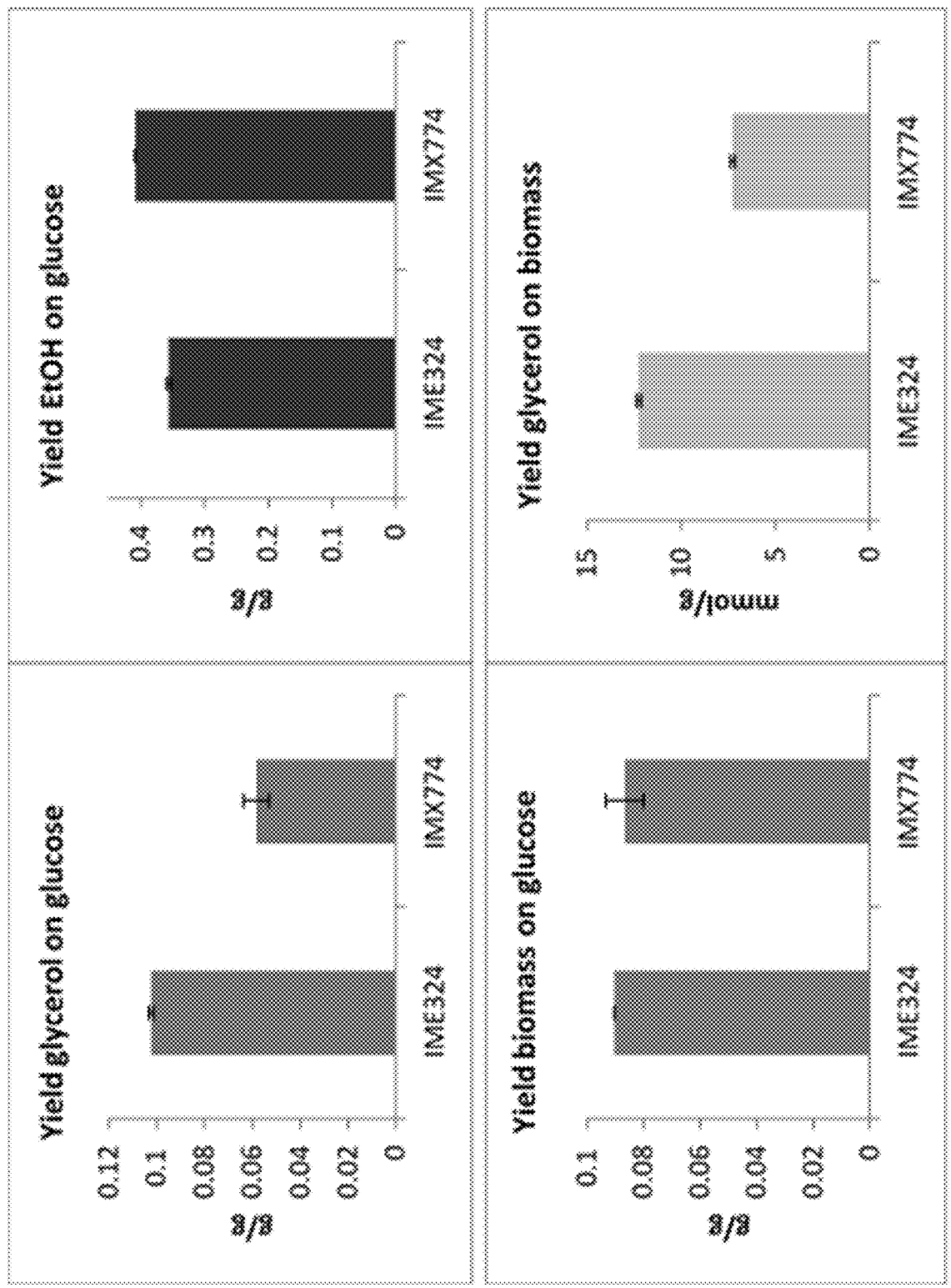
FIG. 2 Yields (Y) of glycerol, biomass and ethanol on glucose and the ratio of glycerol formation to biomass formation in anaerobic bioreactor batch cultures of *S. cerevisiae* strains IME324 and IMX774. Cultures were grown on synthetic medium containing 20 g L$^{-1}$ glucose (pH 5) and sparged with a gas mixture of $N_2/CO_2$ (90%/10%). Yields and ratios were calculated from the exponential growth phase. The ethanol yield on glucose was corrected for evaporation. Values represent average and mean deviation of data from independent duplicate cultures.

Expression of cbbM and prk in S. cerevisiae has previously been shown to result in decreased formation of the by-product glycerol under anaerobic conditions that are relevant for industrial ethanol production [10]. However, in this previous research, prk was expressed under the control of the galactose-inducible GAL1-promoter. The requirement for the presence of galactose and low levels of glucose are a drawback of the use of this promoter. This example investigates the expression of prk under the control of different promoters in a strain that co-expresses Rubisco. Expression cassettes were constructed based on three constitutive promoter sequences of varied expression strengths, with LYS1p being the strongest and YEN1p being the weakest, as well as a weak promoter that is only active in anaerobic conditions (DAN1p) [7]. Initially, transformations were performed with prk cassettes under the control of LYS1p, UBC6p and YEN1p and copies of cbbM, groEL, groES, according to [10]. It was not possible to obtain correct mutant colonies in the case where the LYS1p-prk-PGK1t cassette was used. In the case where UBC6p-prk-PGK1t was used, colonies were obtained but growth was inconsistent and severely impacted, and a stable strain was not obtained, see Table 9. However, in the cases where YEN1p-prk-PGK1t (weakest constitutive promoter tested) it was possible to obtain correct mutant colonies (Table 9). These results could be an indication that high & medium-constitutive expression of prk in S. cerevisiae under aerobic conditions (biomass propagation phase) results in inhibitory effects and are in agreement to data available in literature [10]. Based on the above, a multi-copy, cbbM-expressing strain was constructed with prk under the control of YEN1p (IMX773, low-prk-expression strain). Additionally, a strain was constructed in which a DAN1p-prk-PGK1t cassette was used instead. The promoter of DAN1 (or any other similar promoter) is of particular interest, because it is active in the process conditions of bioethanol production (anaerobic conditions in this case) and does not require the use of specific carbon sources (like GAL1p does) or any other change to the commonly used production process. This promoter (or any other similar promoter) should alleviate the toxicity of prk-expression under aerobic conditions (no transcription). The strain was designated IMX774 (high-prk-expression strain). FIG. 1 shows the PRK activity in cell-free extracts of exponentially growing shake-flask cultures on synthetic medium containing 20 g $L^{-1}$ glucose. Left: IME324, Right: IMX774. To determine whether the promoter of DAN1 could drive the expression of prk in S. cerevisiae, PRK enzymatic activity determination was performed in vitro, using cell-free extracts of anaerobically-grown cultures of strains IME324 (reference) and IMX774 (9*cbbM, DAN1p-prk). PRK activity in IMX774 was ca. 0.8 µmol (mg protein)$^{-1}$ $min^{-1}$ (FIG. 1). To quantitatively analyze the impact of expression of the introduced Rubisco pathway, strains IME324 (reference), IMX773 (9*cbbM, YEN1p-prk) and IMX774 (9*cbbM, DAN1p-prk) were compared in glucose-grown, anaerobic batch cultures in bioreactors. The engineered strains IMX773 and IMX774 grew at 82% and 61%, respectively, of the specific growth rate of the reference strain IME324. The glycerol yield on glucose of strains IMX773 and IMX774 was 0.098 and 0.058 g/g, respectively. This corresponds to 96% of the glycerol yield for IMX773 compared to IME324 indicating a limited impact of the Rubisco pathway in a design in which prk is expressed under control of the weak constitutive promoter YEN1p (Table 8). In contrast, for IMX774 a 43% decrease in glycerol yield compared to the reference strain IME324 was observed (Table 8, FIG. 2). Furthermore, the ratio of glycerol production per g biomass formed of strain IMX774 decreased by 41% compared to the reference strain, whereas for IMX773 this was maintained to 97% of IME324 levels indicating a limited effect. A decrease of glycerol production can be expected when $NAD^+$ is being regenerated via the Rubisco pathway. Therefore, these findings are in agreement with results reported elsewhere on galactose-grown Rubisco-expressing strains [10] and show that the effect of the pathway on galactose-grown cultures can be replicated in glucose-grown ones, when prk is expressed under the control of the promoter of DAN1 but not under control of a weak constitutive promoter such as YEN1p. Even more, prk expression in IMX765 under control of stronger constitutive promoters did not even yield viable colonies, indicating cellular toxicity as a result of transformation of these prk specific expression cassettes. Strains IME324 and IMX774 showed an ethanol yield on glucose of 0.356 and 0.409 g/g respectively (corrected for evaporation). This means that the combination of the decrease in glycerol production, $CO_2$ fixation via the Rubisco pathway and decrease in biomass yield of the engineered, Rubisco-expressing strain IMX774 (FIG. 2) resulted in a ca. 14% increase in the ethanol yield on glucose in the experiments performed in this example.

Cultures were grown on synthetic medium containing 20 g $L^{-1}$ glucose (pH 5) and sparged with a gas mixture of $N_2/CO_2$ (90%/10%). Yields and ratios were calculated from the exponential growth phase. The ethanol yield on glucose was corrected for evaporation. Values represent average and mean deviation of data from independent duplicate cultures.

TABLE 9

Aerobic growth properties and glycerol reduction

| Promoter from the PRK | Strength promoter | Conditions active | Aerobic propagation | Glycerol reduction |
|---|---|---|---|---|
| LYS1p | strong | Constitutive | No colonies formed | n.a. |
| UBC6p | medium | Constitutive | No colonies formed | n.a. |
| YEN1p | Weak | Constitutive | Growth | −3% |
| DAN1p | weak | Anaerobic | Growth | −41% |

Example 2: *S. oleracea* prk Protein Expressed Exclusively Under Anaerobic Conditions in IMX774

Shake Flask Cultivation Strains

IME324 and IMX774 were cultivated in duplicate in mineral medium (according to Luttik et al., 2000) supplemented with 20 g $L^{-1}$ glucose and 0.05 g $L^{-1}$ uracil in shake flasks under aerobic and anaerobic conditions. After overnight aerobic propagation on YePhD, 75 mg $L^{-1}$ of yeast was inoculated to the above described medium in either a 100 mL shake flask filled with 25 mL medium closed afterwards with a cotton plug to recreate aerobic cultivation conditions, or a 25 mL shake flask filled with 25 mL medium (leaving limited head space for aeration) closed afterwards with a water lock to recreate conditions which shortly after inoculation and closing off become anaerobic in the vessel. After 24 hours of cultivation at 32° C. and 250 rpm (for aerobic cultures) and 150 rpm (for anaerobic cultures), 10 OD600 units/mL of cells were harvested from each of the eight shake flasks by centrifugation and cells were washed with ice cold demineralized water. Cell pellets were stored at −80° C. for further processing.

TABLE 8

Maximum specific growth rate (µ), yields (Y) of glycerol, biomass and ethanol on glucose and the ratio of glycerol formation to biomass formation in anaerobic bioreactor batch cultures of *S. cerevisiae* strains IME324, IMX773 and IM3X774.

| Strain | IME324 | IMX773 | IMX774 |
|---|---|---|---|
| Relevant genotype | reference | 9*cbbM, YEN1p-prk, groES, groEL | 9*cbbM, DAN1p-prk, groES, groEL |
| µ ($h^{-1}$) | 0.33 ± 0.01 | 0.27 ± 0.01 | 0.20 ± 0.03 |
| Y glycerol/glucose (g $g^{-1}$) | 0.102 ± 0.001 | 0.098 ± 0.000 | 0.058 ± 0.005 |
| Y biomass/glucose ($g_x$ $g^{-1}$) | 0.091 ± 0.000 | 0.089 ± 0.000 | 0.087 ± 0.007 |
| Y EtOH/glucose (g $g^{-1}$) | 0.356 ± 0.004 | 0.385 ± 0.002 | 0.409 ± 0.001 |
| Ratio glycerol produced/biomass (mmol $g_x^{-1}$) | 12.262 ± 0.122 | 11.879 ± 0.008 | 7.272 ± 0.115 |
| *Degree of reduction ($\gamma_D$) balance | 0.95 ± 0.01   0.95 ± 0.01 | 0.99 ± 0.01   X1.01 ± 0.01 | 1.03 ± 0.01   1.01 ± 0.01 |

*Degree of reduction balances are given for each individual experiment of independent duplicate cultures. Balances calculated over the exponential sampling phase. Averages and standard deviation values of the balances over the sampling points are given.

Protein Extraction and Proteomics

Frozen cells were lysed using mechanical based disruption approach via VK05 glass beads and Precellys 24 homogeniser (Bertin Technologies) in the environment of cold Methanol (Sigma). Protein concentration of the disrupted cell suspension was measured using the Qubit 2.0 fluorometer (Invitrogen, Life Technologies). Two hundred fifty ug of total protein was taken from each methanol suspension and 10 ug BSA was spiked to all the samples for quality control. Proteins were extracted from the disrupted cell suspension using chloroform (Sigma) and 20% TCA (Sigma). The obtained protein pellet was dissolved in 100 mM NH4CO3 buffer at pH 7 (Sigma) to a final concentration of 0.5 ug/uL. Proteins were reduced through the addition of 5 ul of 500 mM Tris(2-carboxyethyl)phosphine hydrochloride solution (TCEP, sigma) and incubated at 55° C. for 30 minutes in a thermocycler to facilitate disulfide reduction. Alkylation was performed through the addition of 5 ul of 550 mM iodoactamide and incubated at 25° C. in the dark for 30 minutes. Proteolysis was carried out overnight in a thermomixer at 37° C. with Trypsin Gold (Promega) at an enzyme to substrate ration of 1:25, which specifically cleaves C-terminally of Lysine and Arginine. Tryptic digests were analyzed on an Ultimate3000 coupled to a QExactive Plus (Thermo Scientific). Gradient elution of peptide was performed on a C18 (Acquity UPLC CSH C18 Column, 130 Å, 1.7 μm, 2.1 mm×100 mm). Twenty uL of injected peptides were separated with a gradient of mobile phase A (99.9% water and 0.1% formic acid; VWR) to 20% B (99.9% acetonitrile and 0.1% formic acid; VWR) over 20 minutes, and to 50% B over 30 minutes, for a final length of 60 minutes. Data acquisition on the qExactive MS was carried out using a data-dependent method. The top 15 precursors were selected for tandem-MS/MS (MS2) analysis after HCD fragmentation. Full MS scans covering the mass range of 400 to 1600 were acquired at a resolution of 70,000 (at m/z 200), with a maximum fill time of 75 milliseconds, and an automatic gain control (AGC) target value of 3e6. MS2 scans were acquired at a resolution of 17,500 (at m/z 200), with a maximum fill time of 75 milliseconds, and an AGC target value of 1e5. An isolation window of 2.0 m/z with a fixed first mass of 110.0 m/z was applied in all experiments. HCD fragmentation was induced with a normalized collision energy of (NCE) of 27 for all peptides. Charge state exclusion was set to ignore unassigned 1 charge. Isotope exclusion was enabled and peptide match was preferred. All LC-MS/MS results were searched against the S. cerevisiae protein database to which the amino acid sequences of the heterologous introduced enzymes were manually added, using Sequest HT on Proteome Discover 1.4 Sequest HT (Thermo Fisher Scientific, San Jose, Calif., USA). The cleavage preference of trypsin was used, allowing up to 2 missed cleavages (C-Term K/R restrict P). Dynamic modifications were set to carbamidomethyl (C), deamidation (N/Q) and oxidation (M). Precursor mass tolerance was set to 10 ppm and fragment mass tolerance 0.6 Da. Following peptide identification, their q-values were calculated based on target decoy approach with a 1% false discovery rate (FDR) and filtered in the Percolator.

Analysis Results

Figure 3:
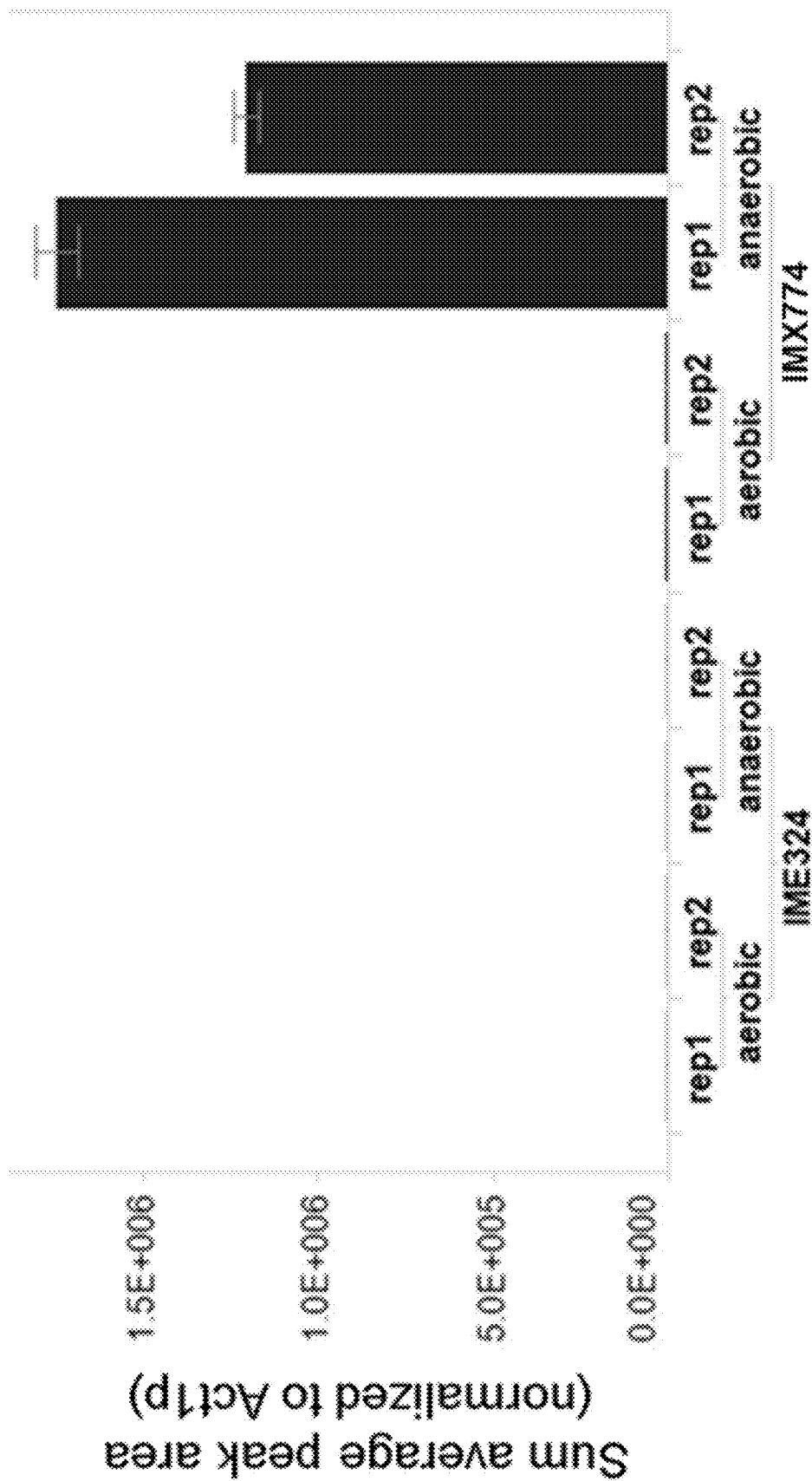
FIG. 3 Sum of peak area of selected unique peptides from *S. oleracea* prk among samples from both strains against prk. The peak areas give an indication of protein amount.

Around 1000 unique proteins were identified in each sample. To quantify the amount of S. oleracea PRK, among all samples, most abundant unique peptides were selected. Peak areas of all peptides were summed up. By normalizing against beta-actin (S. cerevisiae Act1p) amount determined by LC-MS/MS, this value finally gave an indication concerning the protein amount among all samples. As shown in FIG. 3, under both aerobic and anerobic conditions no unique prk peptides are detected for negative control strain IME324 which does not express prk. For IMX774 prk peptides are detected solely under anaerobic conditions indicating that the DAN1p is only inducing prk expression.under anaerobic conditions.

Example 3: Expression of S. oleracea prk Under Control of More Anaerobically Upregulated Promoters Results in Glycerol Reduction in IMX765

Introduction of S. oleracea prk expressed under control of the anaerobically upregulated DAN1 promoter was found to be beneficial to the reduction of glycerol byproduct formation and ethanol yield improvement (Example 1). In constrast to DAN1p, prk introduction with other, constitutively active promoters (UBC6, LYS1, YEN1) placed upstream of S. oleracea prk did not yield viable, correct transformants (UBC6, LYS1) or did not show an impact on glycerol reduction (YEN1p) by implementing the Rubisco pathway. This led us to the conclusion that anaerobically induced/derepressed prk is beneficial to Rubisco pathway flux and results in ethanol yield improvement by reduction of glycerol. DAN1 is regulated by repressor ROX1 which is absent in anaerobic conditions thereby relieving repression on the DAN1 promoter. More such promoters are regulated by ROX1 which display a differential expression pattern being expressed at a higher level under anaerobic conditions than under aerobic conditions (Kwast et al., 1998). In this example, several of these promoters were placed upstream of S. oleracea prk and introduced to strain IMX765 after which resulting strains were subjected to anaerobic growth cultivations. In Table 10, the promoters tested in Example 3 are listed.

TABLE 10

| Anaerobic PRK promotors | | |
|---|---|---|
| Promoter | SEQ ID NO | Length (bp) |
| Sc_DAN1_long | 93 | 1000 |
| Sc_DIP5 | 94 | 967 |
| Sc_TIR3 | 95 | 1000 |
| Sc_TIR2 | 96 | 1000 |
| Sc_HEM13 | 97 | 1000 |
| Sc_YHK8 | 98 | 1000 |
| Sc_FET4 | 99 | 1000 |
| Sc_TIR4 | 100 | 1000 |
| Sc_AAC3 | 101 | 600 |
| Sc_ANB1 | 91 | 601 |

Material and Methods

Expression Cassette Construction The promoters (listed in Table 10; SEQ ID NOs: 91 and 93-101) and terminator, namely Sc_PGK1.ter (SEQ ID NO: 102) sequences were synthesized at DNA2.0 (Menlo Park, Calif. 94025, USA). The S. oleracea prk ORF sequence (Sole_PRK.orf) was obtained by PCR amplification using primer combinations DBC-15631 (SEQ ID NO: 103) and DBC-15632 (SEQ ID NO: 104) using pUDE046 as template. The promoter, ORF and terminator sequences were recombined by using the Golden Gate technology, as described by Engler et al (2011) and references therein. The expression cassettes were cloned into a standard subcloning vector. The promoters listed in Table 10 were ligated to Sole_PRK ORF and Sc_PGK1 terminator resulting in expression cassettes listed in Table 11.

TABLE 11

List of expression (promoter-ORF-terminator) cassettes resulting from Golden Gate Cloning of containing promoter variants, S. oleracea PRK ORF and S. cerevisiae PGK1 terminator; on the 5' end and 3'end connector sequences compatable to neighbouring pathway brick are listed.

| Cassette | 5'connector | promoter | ORF | Terminator | 3'-connector |
|---|---|---|---|---|---|
| cDAN1 | C | Sc_DAN1 | Sole_PRK | Sc_PGK1 | D |
| cDIP5 | C | Sc_DIP5 | Sole_PRK | Sc_PGK1 | D |
| cTIR3 | C | Sc_TIR3 | Sole_PRK | Sc_PGK1 | D |
| cTIR2 | C | Sc_TIR2 | Sole_PRK | Sc_PGK1 | D |
| cHEM13 | C | Sc_HEM13 | Sole_PRK | Sc_PGK1 | D |
| cYHK8 | C | Sc_YHK8 | Sole_PRK | Sc_PGK1 | D |
| cFET4 | C | Sc_FET4 | Sole_PRK | Sc_PGK1 | D |
| cTIR4 | C | Sc_TIR4 | Sole_PRK | Sc_PGK1 | D |
| cAAC3 | C | Sc_AAC3 | Sole_PRK | Sc_PGK1 | D |
| cANB1 | C | Sc_ANB1 | Sole_PRK | Sc_PGK1 | D |

Strain Construction

Approach

The followed strain construction approach is described in patent application PCT/EP2013/056623 and PCT/EP2016/050136. PCT/EP2013/056623 describes the techniques enabling the construction of expression cassettes from various genes of interest in such a way, that these cassettes are combined into a pathway and integrated in a specific locus of the yeast genome upon transformation of this yeast. PCT/EP2016/050136 describes the use of a CRISPR-Cas9 system for integration of expression cassettes into the genome of a host cell, in this case S. cerevisiae. In the construction of IMX765 a S. pyogenes Cas9 expression cassette was already integrated at the CAN1 locus. Upon introduction of an in vivo assembled gRNA-expressing plasmid and repair DNA fragments the intended modifications were made. Firstly, an integration site in the yeast genome was selected. DNA fragments of approximately 500 bp of the up- and downstream parts of the integration locus were amplified by PCR using primers introducing connectors to the generated PCR products. These connectors (50 bp in size) allow for correct in vivo recombination of the pathway upon transformation in yeast. Secondly, the genes of interest, are amplified by PCR, incorporating a different connector (compatible with the connector on the of the neighbouring biobrick) at each flank. Upon transformation of yeast cells with the DNA fragments, in vivo recombination and integration into the genome takes place at the desired location. This technique facilitates parallel testing of multiple genetic designs, as one or more genes from the pathway can be replaced with (an)other gene(s) or genetic element(s), as long as that the connectors that allow for homologous recombination remain constant and compatible with the preceding and following biobrick in the design (patent application PCT/EP2013/056623).

gRNA Expression Plasmid

Integration site: the expression cassettes were targeted at the INT1 locus. The INT1 integration site is a non-coding region between NTR1 (YOR071c) and GYP1 (YOR070c) located on chromosome XV of S. cerevisiae. The guide sequence to target INT1 was designed with a gRNA designer tool (www.dna20.com/eCommerce/cas9/input). The gRNA expression cassette (as described by DiCarlo et al., Nucleic Acids Res. 2013; pp. 1-8) was ordered as synthetic DNA cassette (gBLOCK) at Integrated DNA Technologies (Leuven, Belgium) (INT1 gBLOCK; SEQ ID NO: 105). In vivo assembly of the gRNA expression plasmid is then completed by co-transforming a linear fragment derived from yeast vector pRN599. pRN599 is a multi-copy yeast shuttling vector that contains a functional kanMX marker cassette conferring resistance against G418. The backbone of this plasmid is based on pRS305 (Sikorski and Hieter, Genetics 1989, vol. 122, pp. 19-27), including a functional 2 micron ORI sequence and a functional kanMX marker cassette (SEQ ID NO: 106).

Figure 4:
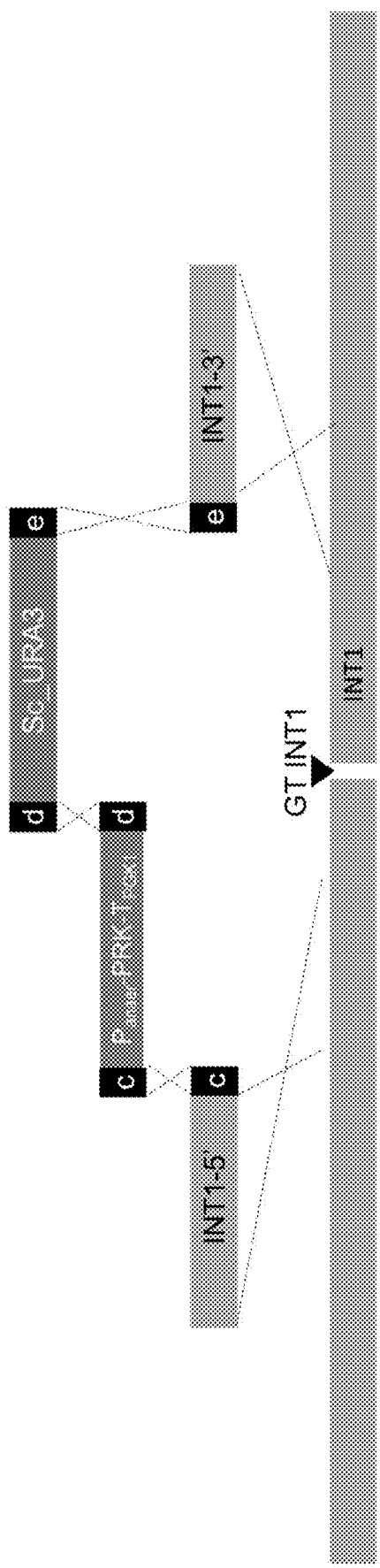
FIG. 4 Illustration of integration of anaerobic promoter-PRK cassettes at INT1 intergenic locus.

Transformation of IMX765 with Specified DNA Fragments Upon Assembly Comprising Anaerobic Promoter PRK Cassette Strain IMX765 was transformed with the following fragments resulting in the assembly of anaerobic promoter PRK as depicted in FIG. 4:

1) a PCR fragment (5'-INT1) generated with primers BoZ-783 (SEQ ID NO: 107) and DBC-19944 (SEQ ID NO: 108) with genomic DNA of strain CEN.PK113-7D as template;
2) a PCR fragment (Anaerobic.pro-PRK) generated with primers DBC-5799 (SEQ ID NO: 109 and DBC-5800 (SEQ ID NO: 110) using either one of the plasmids listed in Table 7 as template;
3) a PCR fragment generated with primers DBC-19947 (SEQ ID NO: 111) and DBC-19949 (SEQ ID NO.112) using genomic DNA of strain CEN.PK113-7D as template; this PCR resulted in the 1.2 kb marker cassette conD-URA3-conE (URA3 marker flanked by connectors D and E).
4) a PCR fragment (3'-INT1) generated with primers DBC-19946 (SEQ ID NO: 113) and BoZ-788 (SEQ ID NO: 114) using genomic DNA of strain CEN.PK113-7D as template;
5) a PCR fragment (BB-599) generated with primers DBC-13775 (SEQ ID NO: 115) and DBC-13776 (SEQ ID NO: 116) using pRN599 (SEQ ID NO: 106) as template;
5) a PCR fragment (gRNA-INT1) generated with primers DBC-13773 (SEQ ID NO: 117) and DBC-13774 (SEQ ID NO: 118) using INT1 gRNA (SEQ ID NO: 105) as template;

Transformants were selected on mineral medium (according to recipe Luttik et al., 2000, Journal of Bacteriology 182, 24: 501-517) supplemented with 1.5% bactoagar supplemented with 20 g L$^{-1}$ glucose and 0.2 mg G418 mL$^{-1}$. Diagnostic PCR was performed to confirm the correct assembly and integration at the INT1 locus of the PRK expression cassettes.

Microtiterplate Batch Fermentation Experiment

Six to nine correct transformants per transformation design and controls strains IME324, IMX765 and IMX774 in nine fold were inoculated to 240 µl mineral medium (according to Luttik et al., 2000) supplemented with 20 g L$^{-1}$ glucose and 0.05 g L$^{-1}$ uracil in microtiterplate format. Inoculated microtiterplates were cultivated for 2 days at 30° C. Subsequently, grown cultures on agar medium were transferred to liquid 350 µl mineral medium (according to Luttik et al., 2000) supplemented with 20 g L$^{-1}$ glucose and 0.05 g $L^{-1}$ uracil with the aid of a pintool to the second microtiterplate for biomass propagation. The microtiterplates were sealed with a gas permeable seal enabling aerobic cultivation conditions and were incubated at 32° C., shaking at 750 rpm at 80% humidity for 2 days. After 2 days, 5 µl grown liquid culture was transferred to 270 µl mineral medium (according to Luttik et al., 2000) supplemented with 20 g $L^{-1}$ glucose and 0.05 g $L^{-1}$ uracil to the third microtiterplate for main fermentation. A high volume of 270 µl leaving little head space volume in the well and sealing microtiterplates with aluminium seal allowed for screening mainly under anaerobic conditions. Cultures were grown for 48 hours at 32° C., 250 rpm at 80% humidity. After 48 hours, samples were taken in order to measure residual glucose, glycerol and ethanol.

Analysis of Glucose, Ethanol, and Glycerol

For the quantification of glucose, ethanol and glycerol, 150 µl of the supernatant sample was transferred accurately into a suitable vial. Subsequently 100 µl internal standard solution, containing maleic acid (20 g/l), EDTA (40 g/l), DSS (4,4-dimethyl-4-silapentane-1-sulfonic acid) (0.5 g/L), adjusted to pH 6.40 with NaOH, in $D_2O$ was added. The sample was further diluted with 400 µl $D_2O$, 1D $^1H$ NMR spectra of the clear solution were recorded on a Bruker Avance III HD spectrometer, operating at a proton frequency of 500 MHz, equipped with a He-cooled cryo probe, using a pulse program with water suppression (ZGCPPR), solvent suppression power of 8 Hz, at a temperature of 300K, 90 degree excitation pulse was used and acquisition time of 2.0 seconds and a relaxation delay of 5 seconds. The number of scans was set at 8, dummy scans were not used. The analyte concentrations [in g/L] were calculated based on the following signals (6 relative to DSS):

Glucose: α-H1 glucose signal (d, 5.21 ppm, 0.38 H, J=4 Hz)
Ethanol: (t, 1.17 ppm, 3H, J=7 Hz)
Glycerol H1/H3 signals: (dd, 3.55 ppm, 2H, J=7 Hz, 12 Hz)
The signal used for the standard:
Maleic acid: (s, 6.05 ppm, 2H)

Results Microtiterplate Fermentation Experiment

Figure 5:
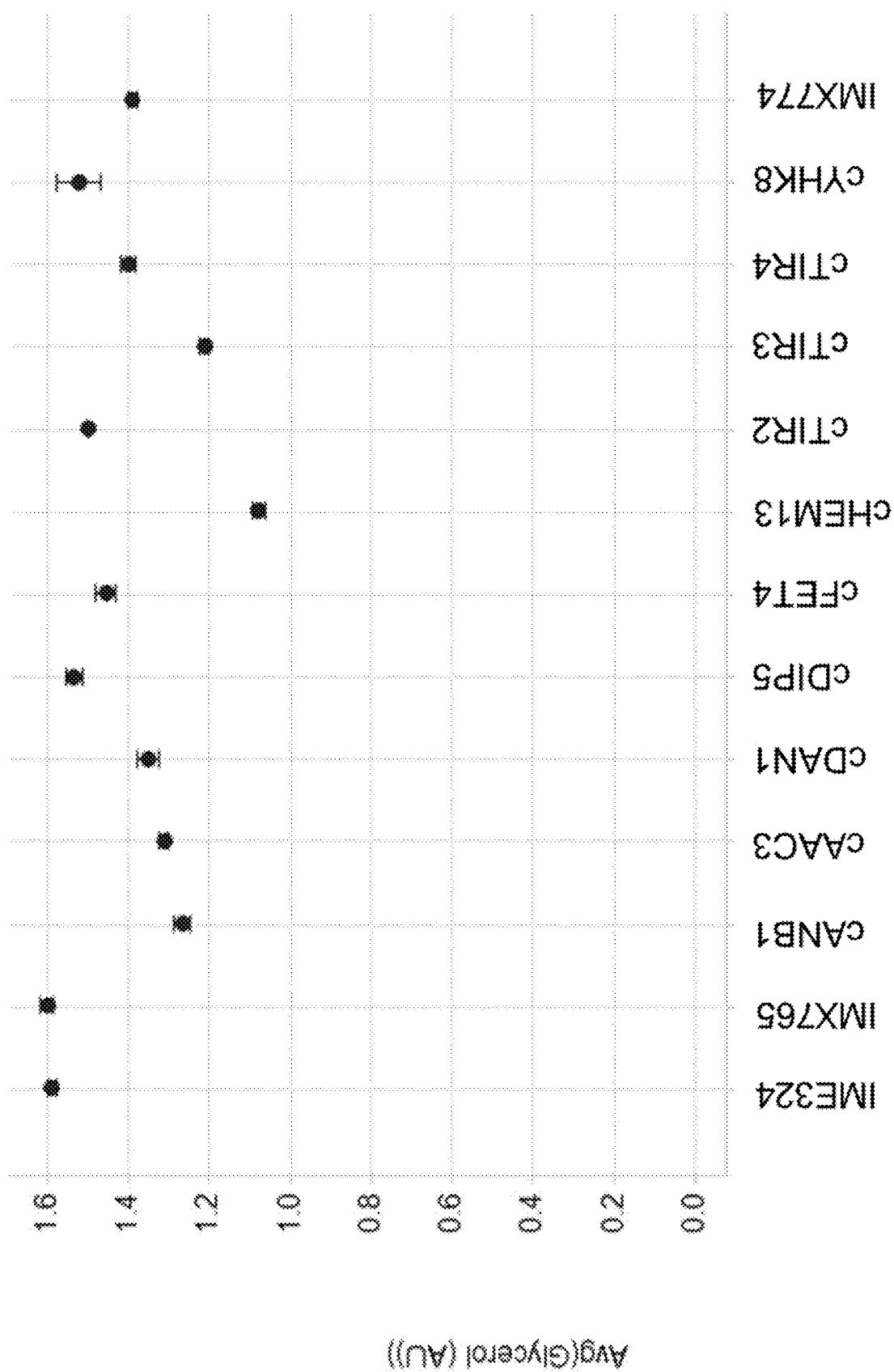
FIG. 5 Average glycerol values end of MTP batch fermentation expressed in arbitrary units (AU) for control strains IME324, IMX774, IMX765 and transformants of IMX765 with expression cassette anaerobic promoter-PRK introduced. Error bars indicate standard error of the mean.
Figure 6:
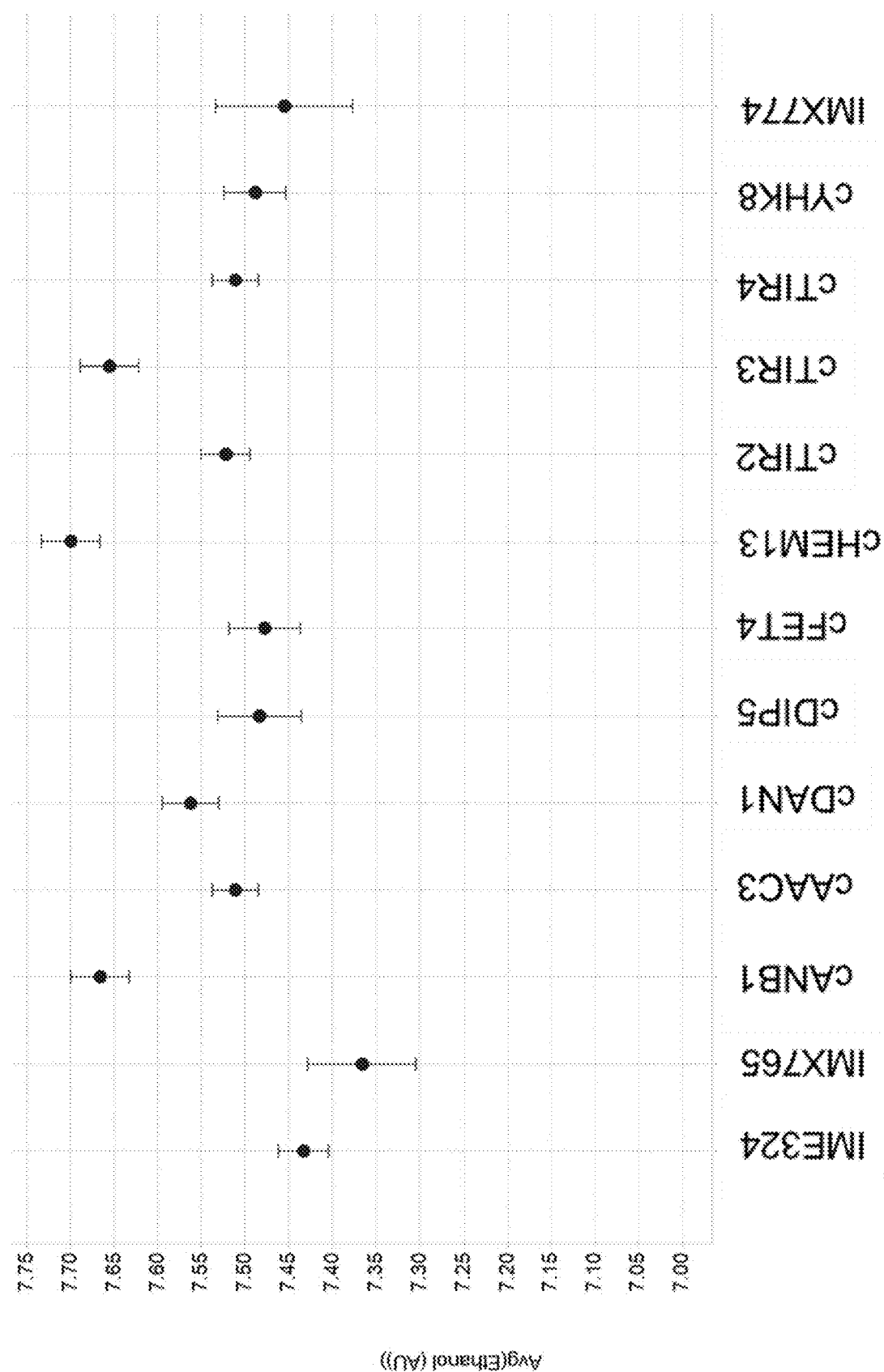
FIG. 6 Average ethanol values expressed in arbitrary units (AU) end of MTP batch fermentation for control strains IME324, IMX774, IMX765 and transformants of IMX765 with expression cassette anaerobic promoter-PRK introduced. Error bars indicate standard error of the mean.

Glucose was completely exhausted in the medium by all replicates of transformants and control strains. The average glycerol levels (expressed as arbitrary units) detected for the transformants with different anaerobic promoter—PRK cassettes and control strains IME324, IMX765 and IMX774 are listed in Table 11 and illustrated in FIG. 5. In this MTP fermentation set up, again IMX774 displayed reduced glycerol levels (87%, reduction of 13%) compared to reference strain IME324 as shown in Example 1. Transformants of cDAN1, which are a reconstruction of IMX774, showed a similar glycerol reduction (85% of IME324 glycerol levels) as IMX774. All tested anaerobic promoter designs displayed reduced glycerol levels compare to IME324. Also one can appreciate designs with anaerobic promoters resulting in transformants with on average even larger reductions of glycerol levels than cDAN1, such as cTIR3, cHEM13, cAAC3, and cANB1 yielding on average 76%, 68%, 82%, and 80%, respectively, of IME324 glycerol levels. As can be observed in Table 12 and FIG. 6 these reductions in glycerol yield were reflected in at least similar, often higher ethanol titers compared to IME324 as seen for cDAN1 (102%), cTIR3 (103%), cHEM13 (104%), cAAC3 (101%), and cANB1 (103%).

TABLE 12

Average glycerol yields expressed as arbitrary units per g glucose of transformants per design anaerobic promoter design and reference strains IME324, IMX774, IMX765 (transformation control) determined in microtiterplate fermentation experiment on mineral medium (according to Luttik) supplemented with 20 g $L^{-1}$ glucose and 0.05 g $L^{-1}$ uracil.

| Background Strain | Cassette | Promoter PRK | Glycerol (AU) | Standard error | Relative to IME324 (%) | Replicates (n = x) |
|---|---|---|---|---|---|---|
| IME324 | N.A. | N.A. | 1.59 | 0.01 | 100 | 9 |
| IMX765 | URA3 | N.A. | 1.60 | 0.02 | 101 | 9 |
| IMX774 | DAN1 (Ex1) | Sc_DAN1 (Ex 1) | 1.39 | 0.01 | 87 | 9 |
| IMX765 | cDAN1 | Sc_DAN1 | 1.35 | 0.03 | 85 | 8 |
| IMX765 | cDIP5 | Sc_DIP5 | 1.53 | 0.02 | 96 | 6 |
| IMX765 | cTIR3 | Sc_TIR3 | 1.21 | 0.01 | 76 | 9 |
| IMX765 | cTIR2 | Sc_TIR2 | 1.50 | 0.01 | 94 | 9 |
| IMX765 | cHEM13 | Sc_HEM13 | 1.08 | 0.01 | 68 | 9 |
| IMX765 | cYHK8 | Sc_YHK8 | 1.52 | 0.05 | 96 | 9 |
| IMX765 | cFET4 | Sc_FET4 | 1.46 | 0.02 | 92 | 9 |
| IMX765 | cTIR4 | Sc_TIR4 | 1.4 | 0.02 | 88 | 9 |
| IMX765 | cAAC3 | Sc_AAC3 | 1.31 | 0.01 | 82 | 9 |
| IMX765 | cANB1 | Sc_ANB1 | 1.27 | 0.02 | 80 | 6 |

N.A., not applicable.

TABLE 13

Average ethanol yields expressed as arbitrary units per g glucose of transformants per design anaerobic promoter design and reference strains IME324, IMX774, IMX765 (transformation control) determined in microtiterplate fermentation experiment on mineral medium (according to Luttik) supplemented with 20 g $L^{-1}$ glucose and 0.05 g $L^{-1}$ uracil.

| Background Strain | Cassette | Promoter PRK | Ethanol (AU)) | Standard error | Relative to IME324 (%) | Replicates (n = x) |
|---|---|---|---|---|---|---|
| IME324 | N.A. | N.A. | 7.43 | 0.03 | 100 | 9 |
| IMX765 | URA3 | N.A. | 7.37 | 0.06 | 99 | 9 |

TABLE 13-continued

Average ethanol yields expressed as arbitrary units per g glucose of transformants per design anaerobic promoter design and reference strains IME324, IMX774, IMX765 (transformation control) determined in microtiterplate fermentation experiment on mineral medium (according to Luttik) supplemented with 20 g $L^{-1}$ glucose and 0.05 g $L^{-1}$ uracil.

| Background Strain | Cassette | Promoter PRK | Ethanol (AU)) | Standard error | Relative to IME324 (%) | Replicates (n = x) |
|---|---|---|---|---|---|---|
| IMX774 | DAN1 (Ex 1) | Sc_DAN1 (Ex 1) | 7.46 | 0.08 | 100 | 9 |
| IMX765 | cDAN1 | Sc_DAN1 (long) | 7.56 | 0.03 | 102 | 8 |
| IMX765 | cDIP5 | Sc_DIP5 | 7.48 | 0.05 | 101 | 6 |
| IMX765 | cTIR3 | Sc_TIR3 | 7.66 | 0.03 | 103 | 9 |
| IMX765 | cTIR2 | Sc_TIR2 | 7.52 | 0.03 | 101 | 9 |
| IMX765 | cHEM13 | Sc_HEM13 | 7.70 | 0.03 | 104 | 9 |
| IMX765 | cYHK8 | Sc_YHK8 | 7.49 | 0.04 | 101 | 9 |
| IMX765 | cFET4 | Sc_FET4 | 7.48 | 0.04 | 101 | 9 |
| IMX765 | cTIR4 | Sc_TIR4 | 7.51 | 0.03 | 101 | 9 |
| IMX765 | cAAC3 | Sc_AAC3 | 7.51 | 0.03 | 101 | 9 |
| IMX765 | cANB1 | Sc_ANB1 | 7.67 | 0.03 | 103 | 6 |

N.A., not applicable.

Example 4. Overexpression of PPP Genes and Deletion of GPD2 Gene

Genes of the non-oxidative branch of the pentose-phosphate pathway (TKL1, NQM1, TKL1, TKL2, RPE1, RKI1) were overexpressed by transforming IMX774 with expression cassettes of the abovementioned genes under control of constitutive promoters as described in pending European Patent Application EP16194660.3. The expression casettes were integrated at the GPD2 locus by co-transforming the guide RNA expression plasmid with GPD2 targeting sequence, thereby abbrogating the coding sequence of gpd2. The resulting strain was named IMX1443. Strain IMX1443 was compared with IME324 and IMX774 in a batch fermentation experiment as described in Example 1. Results are listed in Table 14.

TABLE 14

Results using yeast strain with PPP genes and deletion of GPD2 gene

| Strain | IME324 | IMX774 | IMX1443 |
|---|---|---|---|
| Relevant genotype | reference | 9*cbbM, DAN1p-prk, groES, groEL | 9*cbbM, DAN1p-prk, groES, groEL gpd2::RPE1, TKL1, TAL1, TAL2, RKI1, NQM1 |
| μ ($h^{-1}$) | 0.33 ± 0.01 | 0.20 ± 0.03 | 0.30 ± 0.03 |
| Y glycerol/glucose (g $g^{-1}$) | 0.102 ± 0.001 | 0.058 ± 0.005 | 0.014 ± 0.001 |
| Y biomass/glucose ($g_x$ $g^{-1}$) | 0.091 ± 0.000 | 0.087 ± 0.007 | 0.096 ± 0.004 |
| Y EtOH/glucose (g $g^{-1}$) | 0.356 ± 0.004 | 0.409 ± 0.001 | 0.420 ± 0.001 |
| Ratio glycerol produced/biomass (mmol $g_x^{-1}$) | 12.262 ± 0.122 | 7.272 ± 0.115 | 1.557 ± 0.003 |

REFERENCE LIST

1. Entian K D, Kötter P. Yeast genetic strain and plasmid collections. Method Microbiol. 2007; 629-66.
2. Nijkamp J F, van den Broek M, Datema E, de Kok S, Bosman L, Luttik M A, Daran-Lapujade P, Vongsangnak W, Nielsen J, Heijne W H M, Klaassen P, Paddon C J, Platt D, Kötter P, van Ham R C, Reinders M J T, Pronk J T, de Ridder D, Daran J-M. De novo sequencing, assembly and analysis of the genome of the laboratory strain Saccharomyces cerevisiae CEN.PK113-70, a model for modern industrial biotechnology. Microb Cell Fact. 2012; 11:36.
3. Verduyn C, Postma E, Scheffers W A, van Dijken J P. Effect of benzoic acid on metabolic fluxes in yeasts: A continuous-culture study on the regulation of respiration and alcoholic fermentation. Yeast. 1992; 8:501-17.
4. Mans R, van Rossum H M, Wijsman M, Backx A, Kuijpers N G, van den Broek M, Daran-Lapujade P, Pronk J T, van Maris A J A, Daran J-M. CRISPR/Cas9: a molecular Swiss army knife for simultaneous introduction of multiple genetic modifications in Saccharomyces cerevisiae. FEMS Yeast Res. 2015; 15:fov004.
5. DiCarlo J E, Norville J E, Mali P, Rios X, Aach J, Church G M. Genome engineering in Saccharomyces cerevisiae using CRISPR-Cas systems. Nucleic Acids Res. 2013; 1-8.
6. Mikkelsen M D, Buron L D, Salomonsen B, Olsen C E, Hansen B G, Mortensen U H, Halkier B A. Microbial production of indolylglucosinolate through engineering of a multi-gene pathway in a versatile yeast expression platform. Metab Eng. 2012; 14:104-11.
7. Knijnenburg T A, Daran J M, van den Broek M A, Daran-Lapujade P A, de Winde J H, Pronk J T, Reinders M J, Wessels L F. Combinatorial effects of environmental parameters on transcriptional regulation in *Saccharomyces cerevisiae*: A quantitative analysis of a compendium of chemostat-based transcriptome data. BMC Genomics. 2009; 10:53.
8. Mumberg D, Müller R, Funk M. Yeast vectors for the controlled expression of heterologous proteins in different genetic backgrounds. Gene. 1995; 156:119-22.
9. Gueldener U, Heinisch J, Koehler G J, Voss D, Hegemann J H. A second set of loxP marker cassettes for Cre-mediated multiple gene knockouts in budding yeast. Nucleic Acids Res. 2002; 30:e23.
10. Guadalupe-Medina V, Wisselink H, Luttik M, de Hulster E, Daran J-M, Pronk J T, van Maris A J A. Carbon dioxide fixation by Calvin-Cycle enzymes improves ethanol yield in yeast. Biotechnol Biofuels. 2013; 6:125.
11. Daniel Gietz R, Woods R A: Transformation of yeast by lithium acetate/single-stranded carrier DNA/polyethylene glycol method. Methods Enzymol. 2002:87-96.
12. Solis-Escalante D, Kuijpers N G A, Bongaerts N, Bolat I, Bosman L, Pronk J T, Daran J-M, Daran-Lapujade P. amdSYM, a new dominant recyclable marker cassette for *Saccharomyces cerevisiae*. FEMS Yeast Res. 2013; 13:126-39.
13. Guadalupe-Medina V, Almering M J H, van Maris A J A, Pronk J T. Elimination of glycerol production in anaerobic cultures of a *Saccharomyces cerevisiae* strain engineered to use acetic acid as an electron acceptor. Appl Environ Microb. 2010; 76:190-5.
14. Papapetridis I, van Dijk M, Dobbe A P, Metz B, Pronk J T, van Maris A J A. Improving ethanol yield in acetate-reducing *Saccharomyces cerevisiae* by cofactor engineering of 6-phosphogluconate dehydrogenase and deletion of ALD6. Microb Cell Fact. 2016; 15:1-16.
15. Heijnen J J, van Dijken JP. In search of a thermodynamic description of biomass yields for the chemotrophic growth of microorganisms. Biotechnol Bioeng. 1992; 39:833-58.
16. Postma E, Verduyn C, Scheffers W A, van Dijken J P. Enzymic analysis of the crabtree effect in glucose-limited chemostat cultures of *Saccharomyces cerevisiae*. Appl Environ Microbiol. 1989; 55:468-77.
17. Verduyn C, Postma E, Scheffers W A, van Dijken J P. Physiology of *Saccharomyces cerevisiae* in anaerobic glucose-limited chemostat cultures. J Gen Microbiol. 1990; 136:395-403.
18. Kwast et al. Genomic Analysis of Anaerobically induced genes in *Saccharomyces cerevisiae*: Functional roles of ROX1 and other factors in mediating the anoxic response, 2002, Journal of bacteriology vol 184, not p 250-265.
19. Keng, T. 1992. HAP1 and ROX1 form a regulatory pathway in the repression of HEM13 transcription in *Saccharomyces cerevisiae*. Mol. Cell. Biol. 12: 2616-2623.
20. Labbe-Bois, R., and P. Labbe. 1990. Tetrapyrrole and heme biosynthesis in the yeast *Saccharomyces cerevisiae*, p. 235-285. In H. A. Dailey (ed.), Biosynthesis of heme and chlorophylls. McGraw-Hill, New York, N.Y.
21. Zitomer, R. S., and C. V. Lowry. 1992. Regulation of gene expression by oxygen in *Saccharomyces cerevisiae*. Microbiol. Rev. 56:1-11.
22. Zitomer, R. S., P. Carrico, and J. Decked. 1997. Regulation of hypoxic gene expression in yeast. Kidney Int. 51:507-513.
23. Cohen et al., Induction and repression of DAN1 and the family of anaerobic mannoprotein genes in *Saccharomyces cerevisiae* occurs through a complex array of regulatory sites. Nucleic Acid Research, 2001 Vol. 29, No3, 799-808
24. Ter Kinde and de Steensma, A microarray-assisted screen for potential Hap1 and Rox1 target genes in *Saccharomyces cerevisiae*, 2002, Yeast 19: 825-840.
25. Sertil et al. The DAN1 gene of *S cerevisiae* is regulated in parallel with the hypoxic gene, but by a different mechanism, 1997, Gene Vol 192, pag 199-205.

---

The invention claimed is:

1. A recombinant yeast cell functionally expressing one or more heterologous nucleic acid sequences encoding for ribulose-1,5-phosphate carboxylase/oxygenase (EC4.1.1.39; Rubisco), and one or more phosphoribulokinase (EC2.7.1.19; PRK), wherein the phosphoribulokinase is under control of a promoter or a PRK promoter which has a PRK expression ratio $_{anaerobic/aerobic}$ of 2 or more,
wherein the PRK promoter is the native promoter of a gene selected from the group consisting of: FET4 (FErrous Transport; YMR319C), ANB1 (ANaeroBically induced; YJR047C), YHK8 (YHR048W), DAN1 (Delayed ANaerobic; YJR150C), AAC3 (ADP/ATP Carrier; YBR085W), TIR2 (TIp1-Related; YOR010C), DIP5 (DIcarboxylic amino acid Permease; YPL265W), HEM13 (HEMe biosynthesis; YDR044W), YNR014W, YAR028W, FUN 57, COX5B (Cytochrome c OXidase; YIL111W), OYEZ (Old Yellow Enzyme; YHR179W), SUR2 (SUppressor of Rvs161 and rvs167 mutations; YDR297W), FRDS1 (Fumarate ReDuctase; YEL047C), PIS1 (Phosphatidyl Inositol Synthase; YPR113W), LAC1 (Longevity-Assurance gene Cognate (LAG1 Cognate); YKL008C), YGR035C, FRT2 (Functionally Related to TCP1; YAL028W), EUG1 (ER protein Unnecessary for Growth; YDR518W), HEM14 (HEMe biosynthesis; YER014W), ISU2 (IscU homolog; YOR226C), ERG26 (ERGosterol biosynthesis; YGL001C), MLO01 (Mitochondrially LOcalized protein; YMR252C), SML1 (Suppressor of Mec1 Lethality; YML058W) TIR4 (YOR009W), TIR3 (YIL011W), PAU7 (YAR020C), PAU5 (YFL020C), YLL064C, YGR294W, DAN3 (YBR301W; PAU24), YIL176C, YGL261C, YOL161C, PAU1 (YJL223C), PAU6 (YNR076W), DAN2 (YLR037C; PAU23), YDR542W, YIR041W, YKL224C, PAU3 (YCR104W), YLL025W, YOR394W, YHL046C, YMR325W, YAL068C, YPL282C, PAU2 (YEL049W), and PAU4 (YLR461W).

2. The recombinant yeast cell according to claim 1, wherein the PRK promoter is ROX1 ("regulation by oxygen 1")-repressed.

3. The recombinant yeast cell according to claim 1, wherein the PRK promoter has one or more ROX1 binding motif.

4. The recombinant yeast cell according to claim 1, wherein PRK promoter comprises in a sequence one or more of motif NNNATTGTTNNN (SEQ ID NO:120).

5. The recombinant yeast cell according to claim 1, wherein the PRK promoter is the native promoter of a gene selected from the group consisting of: FET4, ANB1, YHR048W, DAN1, AAC3, TIR2, DIP5 and HEM13.

6. The recombinant yeast cell according to claim 1, wherein the PRK promoter comprises in a sequence thereof one or more of: TCGTTYAG (SEQ ID NO:121); AAAAATTGTTGA (SEQ ID NO:122); or TCGTTYAG (SEQ ID NO:121) and AAAAATTGTTGA (SEQ ID NO:122).

7. The recombinant yeast cell according to claim 1, wherein the PRK promoter is the native promoter of a gene selected from the group consisting of: TIR2, DAN1, TIR4, TIR3, PAU7, PAU5, YLL064C, YGR294W, DAN3, YIL176C, YGL261C, YOL161C, PAU1, PAU6, DAN2, YDR542W, YIR041W, YKL224C, PAU3, YLL025W.

8. The recombinant yeast strain according to claim 1, wherein the PRK promoter is a synthetic oligonucleotide.

9. The recombinant yeast cell according to claim 1, wherein the PRK promoter enables expression only during anaerobic conditions.

10. The recombinant yeast cell according to claim 1, wherein the PRK promoter is the promoter of ANB1; DAN1; or ANB1 and DAN1.

11. The recombinant yeast cell according to claim 1 wherein the Rubisco is under a constitutive promotor.

12. The recombinant yeast cell according to claim 1 in which:
one or more genes of a non-oxidative branch of pentose phosphate pathway are overexpressed;
the yeast cell comprises a deletion or disruption of a glycerol-3-phosphate dehydrogenase (GPD) gene; or
one or more genes of a non-oxidative branch of pentose phosphate pathway are overexpressed and the yeast cell comprises a deletion or disruption of a glycerol-3-phosphate dehydrogenase (GPD) gene.

13. A process for preparing an organic compound, the process comprising converting a carbon source using the recombinant yeast cell according to claim 1, thereby forming the organic compound.

14. The recombinant yeast cell according to claim 1, said cell further functionally expressing one or more heterologous nucleic acid sequences encoding one or more molecular chaperones for Rubisco.

15. The process of claim 13, wherein the organic compound is an alcohol and the carbon source is a carbohydrate.

16. The recombinant yeast cell according to claim 1, wherein the PRK promoter is the native promoter of a gene selected from the group consisting of:
FET4, ANB1, YHK8, DAN1, AAC3, TIR2, DIP5, HEM13, YNR014W, YAR028W, FUN 57, COX5B, OYEZ, SUR2, FRDS1, PIS1, LAC1, YGR035C, FRT2, EUG1, HEM14, ISU2, ERG26, MLO1, and SML1.

17. The recombinant yeast cell according to claim 1, wherein the PRK promoter is the native promoter of a gene selected from the group consisting of:
TIR2, DAN1, TIR4, TIR3, PAU7, PAU5, YLL064C, YGR294W, DAN3, YIL176C, YGL261C, YOL161C, PAU1, PAU6, DAN2, YDR542W, YIR041W, YKL224C, PAU3, YLL025W, YOR394W, YHL046C, YMR325W, YAL068C, YPL282C, PAU2, and PAU4.

* * * * *

SEQUENCE LISTING

```
<160> NUMBER OF SEQ ID NOS: 123

<210> SEQ ID NO 1
<211> LENGTH: 24
<212> TYPE: DNA
<213> ORGANISM: Artificial Sequence
<220> FEATURE:
<223> OTHER INFORMATION: 5793 - pUDR240 construction

<400> SEQUENCE: 1
gatcatttat ctttcactgc ggag                                          24

<210> SEQ ID NO 2
<211> LENGTH: 104
<212> TYPE: DNA
<213> ORGANISM: Artificial Sequence
<220> FEATURE:
<223> OTHER INFORMATION: 6965 - pUDR240 construction

<400> SEQUENCE: 2
gtgcgcatgt ttcggcgttc gaaacttctc cgcagtgaaa gataaatgat cgggcaagga    60
cgtcgaccat agttttagag ctagaaatag caagttaaaa taag                   104

<210> SEQ ID NO 3
<211> LENGTH: 104
<212> TYPE: DNA
```

<213> ORGANISM: Artificial Sequence
<220> FEATURE:
<223> OTHER INFORMATION: 6966 - pUDR240 construction

<400> SEQUENCE: 3
gtgcgcatgt tcggcgttc gaaacttctc cgcagtgaaa gataaatgat cccaagaatt    60
cccattattc ggttttagag ctagaaatag caagttaaaa taag    104

<210> SEQ ID NO 4
<211> LENGTH: 33
<212> TYPE: DNA
<213> ORGANISM: Artificial Sequence
<220> FEATURE:
<223> OTHER INFORMATION: 5792 pUDR119 and pUDR164 construction

<400> SEQUENCE: 4
gttttagagc tagaaatagc aagttaaaat aag    33

<210> SEQ ID NO 5
<211> LENGTH: 17
<212> TYPE: DNA
<213> ORGANISM: Artificial Sequence
<220> FEATURE:
<223> OTHER INFORMATION: 5980 - pUDR119 and pUDR164 construction

<400> SEQUENCE: 5
cgaccgagtt gctcttg    17

<210> SEQ ID NO 6
<211> LENGTH: 20
<212> TYPE: DNA
<213> ORGANISM: Artificial Sequence
<220> FEATURE:
<223> OTHER INFORMATION: 5979 - pUDR119 and pUDR164 construction

<400> SEQUENCE: 6
tattgacgcc gggcaagagc    20

<210> SEQ ID NO 7
<211> LENGTH: 120
<212> TYPE: DNA
<213> ORGANISM: Artificial Sequence
<220> FEATURE:
<223> OTHER INFORMATION: 7023 - pUDR119 construction

<400> SEQUENCE: 7
gttgataacg gactagcctt atttaactt gctatttcta gctctaaaac gaagaattcc    60
agtggtcaat gatcatttat ctttcactgc ggagaagttt cgaacgccga acatgcgca    120

<210> SEQ ID NO 8
<211> LENGTH: 120
<212> TYPE: DNA
<213> ORGANISM: Artificial Sequence
<220> FEATURE:
<223> OTHER INFORMATION: 7374 - pUDR164 construction

<400> SEQUENCE: 8
gttgataacg gactagcctt atttaactt gctatttcta gctctaaaac ctactctctt    60
cctagtcgcc gatcatttat ctttcactgc ggagaagttt cgaacgccga acatgcgca    120

<210> SEQ ID NO 9
<211> LENGTH: 20
<212> TYPE: DNA
<213> ORGANISM: Artificial Sequence

```
<220> FEATURE:
<223> OTHER INFORMATION: 7375 - pUDR164 diagnostic PCR

<400> SEQUENCE: 9
ctactctctt cctagtcgcc                                                  20

<210> SEQ ID NO 10
<211> LENGTH: 40
<212> TYPE: DNA
<213> ORGANISM: Artificial Sequence
<220> FEATURE:
<223> OTHER INFORMATION: 7549 - Addition of 20 bp primer-binding
      sequence to cbbM

<400> SEQUENCE: 10 gcgatacc ct gcgatcttca cagctatgac catgattacg                           40

<210> SEQ ID NO 11
<211> LENGTH: 38
<212> TYPE: DNA
<213> ORGANISM: Artificial Sequence
<220> FEATURE:
<223> OTHER INFORMATION: 7550 - Addition of 20 bp primer-binding
      sequence to cbbM

<400> SEQUENCE: 11
cgcgcagatt agcgaagcct cactataggg cgaattgg                              38

<210> SEQ ID NO 12
<211> LENGTH: 81
<212> TYPE: DNA
<213> ORGANISM: Artificial Sequence
<220> FEATURE:
<223> OTHER INFORMATION: 7074 - cbbM cassette construction - D tag
      addition (single copy cbbm-prk-chaperone integration)

<400> SEQUENCE: 12
acgcatctac gactgtgggt cccgtggaga aatgtatgaa accctgtatg gagagtgatt      60
gctggagctc agtttatcat t                                                81

<210> SEQ ID NO 13
<211> LENGTH: 80
<212> TYPE: DNA
<213> ORGANISM: Artificial Sequence
<220> FEATURE:
<223> OTHER INFORMATION: 7075 - cbbM cassette construction - J tag
      addition (single copy cbbm-prk-chaperone integration)

<400> SEQUENCE: 13
cgacgagatg ctcagactat gtgttctacc tgcttggaca tcttcgcgta tatgacggcc      60
cggccgcaaa ttaaagcctt                                                  80

<210> SEQ ID NO 14
<211> LENGTH: 88
<212> TYPE: DNA
<213> ORGANISM: Artificial Sequence
<220> FEATURE:
<223> OTHER INFORMATION: 7548 - cbbM cassette construction - SGA1 tag
      addition

<400> SEQUENCE: 14
gcatagaaca ttatccgcgg aaacgggtat taggggtgag ggtgaataag gaaagtcagg      60
gaaatcgggc cgcgcagatt agcgaagc                                         88
```

```
<210> SEQ ID NO 15
<211> LENGTH: 79
<212> TYPE: DNA
<213> ORGANISM: Artificial Sequence
<220> FEATURE:
<223> OTHER INFORMATION: 6285 - cbbM cassette construction - G tag
      addition

<400> SEQUENCE: 15
aagggccatg accacctgat gcaccaatta ggtaggtctg gctatgtcta tacctctggc    60 gcgatacccct gcgatcttc                                                 79

<210> SEQ ID NO 16
<211> LENGTH: 79
<212> TYPE: DNA
<213> ORGANISM: Artificial Sequence
<220> FEATURE:
<223> OTHER INFORMATION: 6280 - cbbM cassette construction - A tag
      addition

<400> SEQUENCE: 16
gtgcctattg atgatctggc ggaatgtctg ccgtgccata gccatgcctt cacatatagt    60 gcgatacccct gcgatcttc                                                 79

<210> SEQ ID NO 17
<211> LENGTH: 78
<212> TYPE: DNA
<213> ORGANISM: Artificial Sequence
<220> FEATURE:
<223> OTHER INFORMATION: 6273 - cbbM cassette construction - G tag
      addition

<400> SEQUENCE: 17
gccagaggta tagacatagc cagacctacc taattggtgc atcaggtggt catggccctt    60
cgcgcagatt agcgaagc                                                   78

<210> SEQ ID NO 18
<211> LENGTH: 79
<212> TYPE: DNA
<213> ORGANISM: Artificial Sequence
<220> FEATURE:
<223> OTHER INFORMATION: 6281 - cbbM cassette construction - B tag
      addition

<400> SEQUENCE: 18
gttgaacatt cttaggctgg tcgaatcatt tagacacggg catcgtcctc tcgaaaggtg    60 gcgatacccct gcgatcttc                                                 79

<210> SEQ ID NO 19
<211> LENGTH: 78
<212> TYPE: DNA
<213> ORGANISM: Artificial Sequence
<220> FEATURE:
<223> OTHER INFORMATION: 6270 - cbbM cassette construction - A tag
      addition

<400> SEQUENCE: 19
actatatgtg aaggcatggc tatggcacgg cagacattcc gccagatcat caataggcac    60
cgcgcagatt agcgaagc                                                   78

<210> SEQ ID NO 20
<211> LENGTH: 79
<212> TYPE: DNA
<213> ORGANISM: Artificial Sequence
```

```
<220> FEATURE:
<223> OTHER INFORMATION: 6282 - cbbM cassette construction - C tag
      addition

<400> SEQUENCE: 20
ctagcgtgtc ctcgcatagt tcttagattg tcgctacggc atatacgatc cgtgagacgt      60
gcgataccct gcgatcttc                                                   79

<210> SEQ ID NO 21
<211> LENGTH: 78
<212> TYPE: DNA
<213> ORGANISM: Artificial Sequence
<220> FEATURE:
<223> OTHER INFORMATION: 6271 - cbbM cassette construction - B tag
      addition

<400> SEQUENCE: 21
cacctttcga gaggacgatg cccgtgtcta aatgattcga ccagcctaag aatgttcaac      60
cgcgcagatt agcgaagc                                                    78

<210> SEQ ID NO 22
<211> LENGTH: 79
<212> TYPE: DNA
<213> ORGANISM: Artificial Sequence
<220> FEATURE:
<223> OTHER INFORMATION: 6284 - cbbM cassette construction - D tag
      addition

<400> SEQUENCE: 22
aatcactctc catacagggt ttcatacatt tctccacggg acccacagtc gtagatgcgt      60
gcgataccct gcgatcttc                                                   79

<210> SEQ ID NO 23
<211> LENGTH: 78
<212> TYPE: DNA
<213> ORGANISM: Artificial Sequence
<220> FEATURE:
<223> OTHER INFORMATION: 6272 - cbbM cassette construction - C tag
      addition

<400> SEQUENCE: 23
acgtctcacg gatcgtatat gccgtagcga caatctaaga actatgcgag gacacgctag      60
cgcgcagatt agcgaagc                                                    78

<210> SEQ ID NO 24
<211> LENGTH: 79
<212> TYPE: DNA
<213> ORGANISM: Artificial Sequence
<220> FEATURE:
<223> OTHER INFORMATION: 6283 cbbM cassette construction - D tag
      addition

<400> SEQUENCE: 24
acgcatctac gactgtgggt cccgtggaga aatgtatgaa accctgtatg gagagtgatt      60
gcgataccct gcgatcttc                                                   79

<210> SEQ ID NO 25
<211> LENGTH: 78
<212> TYPE: DNA
<213> ORGANISM: Artificial Sequence
<220> FEATURE:
<223> OTHER INFORMATION: 6275 - cbbM cassette construction - M tag
      addition
```

<400> SEQUENCE: 25
acgagagatg aaggctcacc gatggactta gtatgatgcc atgctggaag ctccggtcat    60
cgcgcagatt agcgaagc                                                  78

<210> SEQ ID NO 26
<211> LENGTH: 79
<212> TYPE: DNA
<213> ORGANISM: Artificial Sequence
<220> FEATURE:
<223> OTHER INFORMATION: 6287 - cbbM cassette construction - M tag
      addition

<400> SEQUENCE: 26
atgaccggag cttccagcat ggcatcatac taagtccatc ggtgagcctt catctctcgt    60
gcgataccct gcgatcttc                                                 79

<210> SEQ ID NO 27
<211> LENGTH: 78
<212> TYPE: DNA
<213> ORGANISM: Artificial Sequence
<220> FEATURE:
<223> OTHER INFORMATION: 6276 - cbbM cassette construction - N tag
      addition

<400> SEQUENCE: 27
ttctaggctt tgatgcaagg tccacatatc ttcgttagga ctcaatcgtg gctgctgatc    60
cgcgcagatt agcgaagc                                                  78

<210> SEQ ID NO 28
<211> LENGTH: 79
<212> TYPE: DNA
<213> ORGANISM: Artificial Sequence
<220> FEATURE:
<223> OTHER INFORMATION: 6288 - cbbM cassette construction - N tag
      addition

<400> SEQUENCE: 28
gatcagcagc cacgattgag tcctaacgaa gatatgtgga ccttgcatca aagcctagaa    60
gcgataccct gcgatcttc                                                 79

<210> SEQ ID NO 29
<211> LENGTH: 78
<212> TYPE: DNA
<213> ORGANISM: Artificial Sequence
<220> FEATURE:
<223> OTHER INFORMATION: 6277 - cbbM cassette construction - O tag
      addition

<400> SEQUENCE: 29
atactccctg cacagatgag tcaagctatt gaacaccgag aacgcgctga acgatcattc    60
cgcgcagatt agcgaagc                                                  78

<210> SEQ ID NO 30
<211> LENGTH: 79
<212> TYPE: DNA
<213> ORGANISM: Artificial Sequence
<220> FEATURE:
<223> OTHER INFORMATION: 6289 - cbbM cassette construction - O tag
      addition

<400> SEQUENCE: 30
gaatgatcgt tcagcgcgtt ctcggtgttc aatagcttga ctcatctgtg cagggagtat    60

```
gcgataccct gcgatcttc                                               79

<210> SEQ ID NO 31
<211> LENGTH: 20
<212> TYPE: DNA
<213> ORGANISM: Artificial Sequence
<220> FEATURE:
<223> OTHER INFORMATION: 7298 - Diagnostic primer cbbM integration

<400> SEQUENCE: 31
ttgttcaatg gatgcggttc                                              20

<210> SEQ ID NO 32
<211> LENGTH: 18
<212> TYPE: DNA
<213> ORGANISM: Artificial Sequence
<220> FEATURE:
<223> OTHER INFORMATION: 4692 - Diagnostic primer cbbM integration

<400> SEQUENCE: 32
aagggccatg accacctg                                                18

<210> SEQ ID NO 33
<211> LENGTH: 21
<212> TYPE: DNA
<213> ORGANISM: Artificial Sequence
<220> FEATURE:
<223> OTHER INFORMATION: 4870 - Diagnostic primer cbbM integration

<400> SEQUENCE: 33
gccagaggta tagacatagc c                                            21

<210> SEQ ID NO 34
<211> LENGTH: 26
<212> TYPE: DNA
<213> ORGANISM: Artificial Sequence
<220> FEATURE:
<223> OTHER INFORMATION: 3275 - Diagnostic primer cbbM integration

<400> SEQUENCE: 34
gtgcctattg atgatctggc ggaatg                                       26

<210> SEQ ID NO 35
<211> LENGTH: 25
<212> TYPE: DNA
<213> ORGANISM: Artificial Sequence
<220> FEATURE:
<223> OTHER INFORMATION: 3847 - Diagnostic primer cbbM integration

<400> SEQUENCE: 35
actatatgtg aaggcatggc tatgg                                        25

<210> SEQ ID NO 36
<211> LENGTH: 27
<212> TYPE: DNA
<213> ORGANISM: Artificial Sequence
<220> FEATURE:
<223> OTHER INFORMATION: 3276 - Diagnostic primer cbbM integration

<400> SEQUENCE: 36
gttgaacatt cttaggctgg tcgaatc                                      27

<210> SEQ ID NO 37
<211> LENGTH: 20
<212> TYPE: DNA
<213> ORGANISM: Artificial Sequence
```

```
<220> FEATURE:
<223> OTHER INFORMATION: 4691 - Diagnostic primer cbbM integration

<400> SEQUENCE: 37
cacctttcga gaggacgatg                                                    20

<210> SEQ ID NO 38
<211> LENGTH: 30
<212> TYPE: DNA
<213> ORGANISM: Artificial Sequence
<220> FEATURE:
<223> OTHER INFORMATION: 3277 - Diagnostic primer cbbM integration

<400> SEQUENCE: 38
ctagcgtgtc ctcgcatagt tcttagattg                                         30

<210> SEQ ID NO 39
<211> LENGTH: 22
<212> TYPE: DNA
<213> ORGANISM: Artificial Sequence
<220> FEATURE:
<223> OTHER INFORMATION: 3283 - Diagnostic primer cbbM integration

<400> SEQUENCE: 39
acgtctcacg gatcgtatat gc                                                 22

<210> SEQ ID NO 40
<211> LENGTH: 20
<212> TYPE: DNA
<213> ORGANISM: Artificial Sequence
<220> FEATURE:
<223> OTHER INFORMATION: 7226 - Diagnostic primer cbbM integration

<400> SEQUENCE: 40
atacatttct ccacgggacc                                                    20

<210> SEQ ID NO 41
<211> LENGTH: 20
<212> TYPE: DNA
<213> ORGANISM: Artificial Sequence
<220> FEATURE:
<223> OTHER INFORMATION: 7225 - Diagnostic primer cbbM integration

<400> SEQUENCE: 41
gtcccgtgga gaaatgtatg                                                    20

<210> SEQ ID NO 42
<211> LENGTH: 20
<212> TYPE: DNA
<213> ORGANISM: Artificial Sequence
<220> FEATURE:
<223> OTHER INFORMATION: 6629 - Diagnostic primer cbbM integration

<400> SEQUENCE: 42
acgagagatg aaggctcacc                                                    20

<210> SEQ ID NO 43
<211> LENGTH: 21
<212> TYPE: DNA
<213> ORGANISM: Artificial Sequence
<220> FEATURE:
<223> OTHER INFORMATION: 4184 - Diagnostic primer cbbM integration

<400> SEQUENCE: 43
atgaccggag cttccagcat g                                                  21
```

```
<210> SEQ ID NO 44
<211> LENGTH: 22
<212> TYPE: DNA
<213> ORGANISM: Artificial Sequence
<220> FEATURE:
<223> OTHER INFORMATION: 3842 - Diagnostic primer cbbM integration

<400> SEQUENCE: 44
ttctaggctt tgatgcaagg tc                                              22

<210> SEQ ID NO 45
<211> LENGTH: 18
<212> TYPE: DNA
<213> ORGANISM: Artificial Sequence
<220> FEATURE:
<223> OTHER INFORMATION: 3843Diagnostic primer cbbM integration

<400> SEQUENCE: 45
gatcagcagc cacgattg                                                   18

<210> SEQ ID NO 46
<211> LENGTH: 19
<212> TYPE: DNA
<213> ORGANISM: Artificial Sequence
<220> FEATURE:
<223> OTHER INFORMATION: 3840 - Diagnostic primer cbbM integration

<400> SEQUENCE: 46
atactccctg cacagatga                                                  19

<210> SEQ ID NO 47
<211> LENGTH: 18
<212> TYPE: DNA
<213> ORGANISM: Artificial Sequence
<220> FEATURE:
<223> OTHER INFORMATION: 3837 Diagnostic primer cbbM integration

<400> SEQUENCE: 47
gaatgatcgt tcagcgcg                                                   18

<210> SEQ ID NO 48
<211> LENGTH: 21
<212> TYPE: DNA
<213> ORGANISM: Artificial Sequence
<220> FEATURE:
<223> OTHER INFORMATION: 7228 - Diagnostic primer cbbM integration

<400> SEQUENCE: 48
tctacctgct tggacatctt c                                               21

<210> SEQ ID NO 49
<211> LENGTH: 20
<212> TYPE: DNA
<213> ORGANISM: Artificial Sequence
<220> FEATURE:
<223> OTHER INFORMATION: 7227 - Diagnostic primer cbbM integration

<400> SEQUENCE: 49
atacgcgaag atgtccaagc                                                 20

<210> SEQ ID NO 50
<211> LENGTH: 22
<212> TYPE: DNA
<213> ORGANISM: Artificial Sequence
<220> FEATURE:
<223> OTHER INFORMATION: 3290 - Diagnostic primer cbbM integration
```

<400> SEQUENCE: 50
gtcacgggtt ctcagcaatt cg                                        22

<210> SEQ ID NO 51
<211> LENGTH: 23
<212> TYPE: DNA
<213> ORGANISM: Artificial Sequence
<220> FEATURE:
<223> OTHER INFORMATION: 3291 - Diagnostic primer cbbM integration

<400> SEQUENCE: 51
ctctaacgcc tcagccatca tcg                                       23

<210> SEQ ID NO 52
<211> LENGTH: 22
<212> TYPE: DNA
<213> ORGANISM: Artificial Sequence
<220> FEATURE:
<223> OTHER INFORMATION: 4229 - Diagnostic primer cbbM integration

<400> SEQUENCE: 52
tggtcgacag atacaatcct gg                                        22

<210> SEQ ID NO 53
<211> LENGTH: 20
<212> TYPE: DNA
<213> ORGANISM: Artificial Sequence
<220> FEATURE:
<223> OTHER INFORMATION: 1370 - Diagnostic primer cbbM integration

<400> SEQUENCE: 53
gtttgatggt ccagctacag                                           20

<210> SEQ ID NO 54
<211> LENGTH: 21
<212> TYPE: DNA
<213> ORGANISM: Artificial Sequence
<220> FEATURE:
<223> OTHER INFORMATION: 1371 - Diagnostic primer cbbM integration

<400> SEQUENCE: 54
aaatagcacc agcagcagga g                                         21

<210> SEQ ID NO 55
<211> LENGTH: 83
<212> TYPE: DNA
<213> ORGANISM: Artificial Sequence
<220> FEATURE:
<223> OTHER INFORMATION: 7076 - groEL cassette construction - J tag
      addition

<400> SEQUENCE: 55
ggccgtcata tacgcgaaga tgtccaagca ggtagaacac atagtctgag catctcgtcg    60
cgaccatagc ttcaaaatgt ttc                                           83

<210> SEQ ID NO 56
<211> LENGTH: 83
<212> TYPE: DNA
<213> ORGANISM: Artificial Sequence
<220> FEATURE:
<223> OTHER INFORMATION: 7077 - groEL cassette construction - H tag
      addition

<400> SEQUENCE: 56
gtcacgggtt ctcagcaatt cgagctatta ccgatgatgg ctgaggcgtt agagtaatct    60
gctcgacatt ttatgatgga atg    83

<210> SEQ ID NO 57
<211> LENGTH: 82
<212> TYPE: DNA
<213> ORGANISM: Artificial Sequence
<220> FEATURE:
<223> OTHER INFORMATION: 7078 - groES cassette construction - H tag
      addition

<400> SEQUENCE: 57
agattactct aacgcctcag ccatcatcgg taatagctcg aattgctgag aacccgtgac    60
gggatctacg tatggtcatt tc    82

<210> SEQ ID NO 58
<211> LENGTH: 81
<212> TYPE: DNA
<213> ORGANISM: Artificial Sequence
<220> FEATURE:
<223> OTHER INFORMATION: 7079 - groES cassette construction - SGA1 tag
      addition

<400> SEQUENCE: 58
tatatttgat gtaaatatct aggaaataca cttgtgtata cttctcgctt ttcttttatt    60 cgcccttttta aacagttgat g    81

<210> SEQ ID NO 59
<211> LENGTH: 79
<212> TYPE: DNA
<213> ORGANISM: Artificial Sequence
<220> FEATURE:
<223> OTHER INFORMATION: 7082 - LYS1p prk cassette construction

<400> SEQUENCE: 59
acgtctcacg gatcgtatat gccgtagcga caatctaaga actatgcgag gacacgctag    60
aacgctggtg tcctagagc    79

<210> SEQ ID NO 60
<211> LENGTH: 21
<212> TYPE: DNA
<213> ORGANISM: Artificial Sequence
<220> FEATURE:
<223> OTHER INFORMATION: 7083 - LYS1p prk cassette construction

<400> SEQUENCE: 60
ttttgcggtt gtgtgaaaaa t    21

<210> SEQ ID NO 61
<211> LENGTH: 80
<212> TYPE: DNA
<213> ORGANISM: Artificial Sequence
<220> FEATURE:
<223> OTHER INFORMATION: 7292UBC6p prk cassette construction

<400> SEQUENCE: 61
acgtctcacg gatcgtatat gccgtagcga caatctaaga actatgcgag gacacgctag    60
gcccgcgatt tatccttctt    80

<210> SEQ ID NO 62
<211> LENGTH: 25
<212> TYPE: DNA
<213> ORGANISM: Artificial Sequence
<220> FEATURE:
<223> OTHER INFORMATION: 7294 - UBC6p prk cassette construction

<400> SEQUENCE: 62
tactattgta cgtactttgt ttgca                                           25

<210> SEQ ID NO 63
<211> LENGTH: 82
<212> TYPE: DNA
<213> ORGANISM: Artificial Sequence
<220> FEATURE:
<223> OTHER INFORMATION: 7293 - YEN1p prk cassette construction

<400> SEQUENCE: 63
acgtctcacg gatcgtatat gccgtagcga caatctaaga actatgcgag gacacgctag      60
ggaattcaag caatagcgtt tc                                              82

<210> SEQ ID NO 64
<211> LENGTH: 24
<212> TYPE: DNA
<213> ORGANISM: Artificial Sequence
<220> FEATURE:
<223> OTHER INFORMATION: 7295 - YEN1p prk cassette construction

<400> SEQUENCE: 64
tttcttgtgc agtatccaga atat                                            24

<210> SEQ ID NO 65
<211> LENGTH: 80
<212> TYPE: DNA
<213> ORGANISM: Artificial Sequence
<220> FEATURE:
<223> OTHER INFORMATION: 7930 - DAN1p prk cassette construction

<400> SEQUENCE: 65
tcacagaggg atcccgttac ccatctatgc tgaagattta tcatactatt cctccgctcg      60
agaatgcaag ggcaaacagg                                                 80

<210> SEQ ID NO 66
<211> LENGTH: 25
<212> TYPE: DNA
<213> ORGANISM: Artificial Sequence
<220> FEATURE:
<223> OTHER INFORMATION: 7931 - DAN1p prk cassette construction

<400> SEQUENCE: 66
tacttggggt atatatttag tatgc                                           25

<210> SEQ ID NO 67
<211> LENGTH: 24
<212> TYPE: DNA
<213> ORGANISM: Artificial Sequence
<220> FEATURE:
<223> OTHER INFORMATION: 7084 - prk cassette construction (PGK1t)

<400> SEQUENCE: 67
attgaattga attgaaatcg atag                                            24

<210> SEQ ID NO 68
<211> LENGTH: 81
<212> TYPE: DNA
<213> ORGANISM: Artificial Sequence
<220> FEATURE:
<223> OTHER INFORMATION: 7085 - prk cassette construction (PGK1t) - D
      tag addition (single copy cbbm-prk-chaperone integration)

```
<400> SEQUENCE: 68
aatcactctc catacagggt tcatacatt tctccacggg acccacagtc gtagatgcgt      60
gcttcaagct tacacaacac g                                              81

<210> SEQ ID NO 69
<211> LENGTH: 81
<212> TYPE: DNA
<213> ORGANISM: Artificial Sequence
<220> FEATURE:
<223> OTHER INFORMATION: 7934 - prk cassette construction (PGK1t) - X-2
      tag addition

<400> SEQUENCE: 69
gtcataactc aatttgccta tttcttacgg cttctcataa aacgtcccac actattcagg      60
gcttcaagct tacacaacac g                                              81

<210> SEQ ID NO 70
<211> LENGTH: 54
<212> TYPE: DNA
<213> ORGANISM: Artificial Sequence
<220> FEATURE:
<223> OTHER INFORMATION: 7080 - prk amplification (LYS1p cassette)

<400> SEQUENCE: 70
aaacgcttta ttttcacac aaccgcaaaa atgtcacaac aacaaacaat tgtg            54

<210> SEQ ID NO 71
<211> LENGTH: 50
<212> TYPE: DNA
<213> ORGANISM: Artificial Sequence
<220> FEATURE:
<223> OTHER INFORMATION: 7081 - prk amplification

<400> SEQUENCE: 71
attgatctat cgatttcaat tcaattcaat ctaggcttta gcagctgttg                50

<210> SEQ ID NO 72
<211> LENGTH: 56
<212> TYPE: DNA
<213> ORGANISM: Artificial Sequence
<220> FEATURE:
<223> OTHER INFORMATION: 7296 - prk amplification (UBC6p cassette)

<400> SEQUENCE: 72
cgcaaattgc aaacaaagta cgtacaatag taatgtcaca acaacaaaca attgtg         56

<210> SEQ ID NO 73
<211> LENGTH: 54
<212> TYPE: DNA
<213> ORGANISM: Artificial Sequence
<220> FEATURE:
<223> OTHER INFORMATION: 7297 - prk amplification (YEN1p cassette)

<400> SEQUENCE: 73
acttgtatat tctggatact gcacaagaaa atgtcacaac aacaaacaat tgtg           54

<210> SEQ ID NO 74
<211> LENGTH: 81
<212> TYPE: DNA
<213> ORGANISM: Artificial Sequence
<220> FEATURE:
<223> OTHER INFORMATION: 7932 - prk amplification (DAN1p cassette)

<400> SEQUENCE: 74
```

```
ttgcagataa aagtgtagca gataaaagtg tagcatacta aatatatacc ccaagtaatg    60
tcacaacaac aaacaattgt g                                             81
```

<210> SEQ ID NO 75
<211> LENGTH: 82
<212> TYPE: DNA
<213> ORGANISM: Artificial Sequence
<220> FEATURE:
<223> OTHER INFORMATION: 7086 - URA3 amplification - SGA1 tag addition
      (single copy cbbm-prk-chaperone integration)

<400> SEQUENCE: 75

```
tttacaatat agtgataatc gtggactaga gcaagatttc aaataagtaa cagcagcaaa    60
gatcccaata caacagatca cg                                            82
```

<210> SEQ ID NO 76
<211> LENGTH: 83
<212> TYPE: DNA
<213> ORGANISM: Artificial Sequence
<220> FEATURE:
<223> OTHER INFORMATION: 7087 - URA3 amplification - C tag addition
      (single copy cbbm-prk-chaperone integration)

<400> SEQUENCE: 76

```
ctagcgtgtc ctcgcatagt tcttagattg tcgctacggc atatcgatc cgtgagacgt     60 ctcgagagct cgttttattt agg                                           83
```

<210> SEQ ID NO 77
<211> LENGTH: 27
<212> TYPE: DNA
<213> ORGANISM: Artificial Sequence
<220> FEATURE:
<223> OTHER INFORMATION: 4221 - Diagnostic primer single copy cbbm-prk-
      chaperone integration

<400> SEQUENCE: 77

```
aaacttagat tagattgcta tgctttc                                       27
```

<210> SEQ ID NO 78
<211> LENGTH: 20
<212> TYPE: DNA
<213> ORGANISM: Artificial Sequence
<220> FEATURE:
<223> OTHER INFORMATION: 2674 - Diagnostic primer single copy cbbm-prk-
      chaperone integration

<400> SEQUENCE: 78

```
atagccaccc aaggcatttc                                               20
```

<210> SEQ ID NO 79
<211> LENGTH: 20
<212> TYPE: DNA
<213> ORGANISM: Artificial Sequence
<220> FEATURE:
<223> OTHER INFORMATION: 7376 - Diagnostic primer prk integration in X-2

<400> SEQUENCE: 79

```
ggtctaggcc tgcataatcg                                               20
```

<210> SEQ ID NO 80
<211> LENGTH: 20
<212> TYPE: DNA
<213> ORGANISM: Artificial Sequence
<220> FEATURE:

<223> OTHER INFORMATION: 7377 - Diagnostic primer prk integration in X-2

<400> SEQUENCE: 80
tgcggcatca tgtctacttg                                                      20

<210> SEQ ID NO 81
<211> LENGTH: 24
<212> TYPE: DNA
<213> ORGANISM: Artificial Sequence
<220> FEATURE:
<223> OTHER INFORMATION: 2375 - Diagnostic primer prk integration in X-2

<400> SEQUENCE: 81
tgagccactt aaatttcgtg aatg                                                 24

<210> SEQ ID NO 82
<211> LENGTH: 21
<212> TYPE: DNA
<213> ORGANISM: Artificial Sequence
<220> FEATURE:
<223> OTHER INFORMATION: 2376 - Diagnostic primer prk integration in X-2

<400> SEQUENCE: 82
gcctttgagt gagctgatac c                                                    21

<210> SEQ ID NO 83
<211> LENGTH: 120
<212> TYPE: DNA
<213> ORGANISM: Artificial Sequence
<220> FEATURE:
<223> OTHER INFORMATION: 6967 - Repair fragment GPD1

<400> SEQUENCE: 83
tggtattggc agtttcgtag ttatatatat actaccatga gtgaaactgt tacgttacct          60
gcattatgtc atttctcata actactttat cacgttagaa attacttatt attattaaat         120

<210> SEQ ID NO 84
<211> LENGTH: 120
<212> TYPE: DNA
<213> ORGANISM: Artificial Sequence
<220> FEATURE:
<223> OTHER INFORMATION: 6968 - Repair fragment GPD1

<400> SEQUENCE: 84
atttaataat aataagtaat ttctaacgtg ataaagtagt tatgagaaat gacataatgc          60
aggtaacgta acagtttcac tcatggtagt atatatataa ctacgaaact gccaatacca         120

<210> SEQ ID NO 85
<211> LENGTH: 120
<212> TYPE: DNA
<213> ORGANISM: Artificial Sequence
<220> FEATURE:
<223> OTHER INFORMATION: 6969 - Repair fragment GPD2

<400> SEQUENCE: 85
gtattttggt agattcaatt ctctttccct ttccttttcc ttcgctcccc ttccttatca          60
aaccaattta tcattataca caagttctac aactactact agtaacatta ctacagttat         120

<210> SEQ ID NO 86
<211> LENGTH: 120
<212> TYPE: DNA
<213> ORGANISM: Artificial Sequence
<220> FEATURE:
<223> OTHER INFORMATION: 6970 - Repair fragment GPD2

<400> SEQUENCE: 86
ataactgtag taatgttact agtagtagtt gtagaacttg tgtataatga taaattggtt     60
tgataaggaa ggggagcgaa ggaaaaggaa agggaaagag aattgaatct accaaaatac    120

<210> SEQ ID NO 87
<211> LENGTH: 20
<212> TYPE: DNA
<213> ORGANISM: Artificial Sequence
<220> FEATURE:
<223> OTHER INFORMATION: 4398 - Diagnostic primer GPD1 deletion

<400> SEQUENCE: 87
tctcacctct caccgctgac                                                 20

<210> SEQ ID NO 88
<211> LENGTH: 20
<212> TYPE: DNA
<213> ORGANISM: Artificial Sequence
<220> FEATURE:
<223> OTHER INFORMATION: 4401 - Diagnostic primer GPD1 deletion

<400> SEQUENCE: 88
acggtgagct ccgtattatc                                                 20

<210> SEQ ID NO 89
<211> LENGTH: 18
<212> TYPE: DNA
<213> ORGANISM: Artificial Sequence
<220> FEATURE:
<223> OTHER INFORMATION: 2112 - Diagnostic primer GPD2 deletion

<400> SEQUENCE: 89
acggacctat tgccattg                                                   18

<210> SEQ ID NO 90
<211> LENGTH: 20
<212> TYPE: DNA
<213> ORGANISM: Artificial Sequence
<220> FEATURE:
<223> OTHER INFORMATION: 2015 - Diagnostic primer GPD2 deletion

<400> SEQUENCE: 90
ccaaatgcga catgagtcac                                                 20

<210> SEQ ID NO 91
<211> LENGTH: 600
<212> TYPE: DNA
<213> ORGANISM: Saccharomyces cerevisiae
<220> FEATURE:
<221> NAME/KEY: misc_feature
<222> LOCATION: (1)..(600)
<223> OTHER INFORMATION: Promoter ANB1

<400> SEQUENCE: 91
agatcggtga aaacatcttg atcttgctcc cgggaatttt agattcaggt aggaaattga     60
ttacatcaat actgttaccc tgaatcatat tcgacgatgt cgtctcacac ggaaatataa    120
ttcatttctt ggttttccaa aaaaattttc attttttttc acttttttgt ttcgtcctcc    180
tttttttttt tttttttttta ttttttttcc tgtgttcacc ttttttttttt tcagttgaca    240 tctttctgca ttcttttctg tgttttttttt tttttttttc gttttttccat tgttcgttcg    300 ttgcctgttt tttcgcccta ttgttctcga gcctaaaaat ttttttccttt cctgctttcc    360

```
tttcttcgtt caaagtttcc tattccattg ttctctttgg taaactcatt gttgtcggaa    420
ctcagatata ttcaggtcaa tttactgtac ttcaattgac ttttttcttg aaatttcaac    480
ttgccttttc aacttgttct tctttttttaa tcttattcta cactttagtt cccttacctt    540
gttcctaatt attgtctagc aaaagaaaa catacaccta tttcattcac acactaaaac    600
```

<210> SEQ ID NO 92
<211> LENGTH: 825
<212> TYPE: DNA
<213> ORGANISM: Saccharomyces cerevisiae
<220> FEATURE:
<221> NAME/KEY: misc_feature
<222> LOCATION: (1)..(825)
<223> OTHER INFORMATION: Promoter DAN1

<400> SEQUENCE: 92

```
agaatgcaag ggcaaacagg cctgaggtaa cttttaaaata taatgtacct tgaaaactat     60
gtatacattg catttattaa gcagtagggt attttgtttg caagaaaata aagctcaaaa    120
tatctttgga gtttgacaat agtatagaaa aaatagctca gcaaccttaa taaaaaaagg    180
gtcattgggc aaagcgtttt aaaaagattt aagtggtagt gtttaaagtg aaagagattg    240
atatagttaa aaattgttga gctcaattca cgctggattc ggcgatccgt ttcttcaat    300 cctcacgtgc tttcttcgtt tgagtgcaaa agttcatatg atgctatctc ccgcttatct    360
tattagtcga aaatggggag aatttcctat tttatctgtc gtttagcaca tacggccagg    420
aaaatacata agatttcgcc gaacgacggg gtcaattcgt ccttttgta cacatcgttt     480 aatttatgag gaaaaattga tgaacgtatc ctccgtagac gctcctctga aaagtttcat    540
gtttcctgcg cgttcctttg ataggcaata aacaataca acgcgtgcct ttgaaaatgc    600
caagatctat acgaggcctc taacaaaaca tcgttcagga acagagaatg ctaaaaatgc    660
aaaagggtcc ctgggtactc attgaataga aatgattgaa aatactgcgt ataaaatagc    720
acgactaaat gatactattt ttatgtcgac acggtactat ttcttctttt gcagataaaa    780
gtgtagcaga taaaagtgta gcatactaaa tatatacccc aagta                   825
```

<210> SEQ ID NO 93
<211> LENGTH: 1000
<212> TYPE: DNA
<213> ORGANISM: Saccharomyces cerevisiae
<220> FEATURE:
<221> NAME/KEY: misc_feature
<222> LOCATION: (1)..(1000)
<223> OTHER INFORMATION: Sc_DAN1 promoter

<400> SEQUENCE: 93

```
gtttatggat gcacttaggg gtcctacaag ccttcgtatg aagttgcccc tcgcaagcac     60
actataaatt catgaacaat tgcgcagtca aagttagatt gtaagccgaa ttcaaacgat    120
ttcaacagtc gtagctaacg aggccttttg tctcacaccc ttacaaaggg actgtagaat    180
gcaagggcaa acaggcctga ggtaacttta aaatataatg taccttgaaa actatgtata    240
cattgcattt attaagcagt agggtatttt gtttgcaaga aaataaagct caaaatatct    300
ttggagtttg acaatagtat agaaaaaata gctcagcaac cttaataaaa aaagggtcat    360
tgggcaaagc gttttaaaaa gatttaagtg gtagtgttta agtgaaaga gattgatata    420 gttaaaaatt gttgagctca attcacgctg gattcggcga tccgttttct tcaatcctca    480
cgtgctttct tcgtttgagt gcaaaagttc atatgatgct atctcccgct tatcttatta    540
gtcgaaaatg gggagaattt cctattttat ctgtcgttta gcacatacgg ccaggaaaat    600
```

| acataagatt tcgccgaacg acggggtcaa ttcgtccttt ttgtacacat cgtttaattt | 660 |
| atgaggaaaa attgatgaac gtatcctccg tagacgctcc tctgaaaagt ttcatgtttc | 720 |
| ctgcgcgttc ctttgatagg caataaaaca atacaacgcg tgcctttgaa aatgccaaga | 780 |
| tctatacgag gcctctaaca aaacatcgtt caggaacaga gaatgctaaa aatgcaaaag | 840 |
| ggtccctggg tactcattga atagaaatga ttgaaaatac tgcgtataaa atagcacgac | 900 |
| taaatgatac tatttttatg tcgacacggt actatttctt cttttgcaga taaaagtgta | 960 |
| gcagataaaa gtgtagcata ctaaatatat accccaagta | 1000 |

<210> SEQ ID NO 94
<211> LENGTH: 967
<212> TYPE: DNA
<213> ORGANISM: Saccharomyces cerevisiae
<220> FEATURE:
<221> NAME/KEY: misc_feature
<222> LOCATION: (1)..(967)
<223> OTHER INFORMATION: Sc_DIP5 promoter

<400> SEQUENCE: 94

| gctctcttat caattatgta agtgcttgta tactatttac ctaagataag aaaaaaaaaa | 60 |
| aagcaattca aaattaagct tatcttgaca gcggggctgg tttgtttcta gaagacaaaa | 120 |
| agtggggaat catttttacg taactccccc tgataagaag gactcacatc cttataggta | 180 |
| cgataaagaa tggttgtatc tttcctattt ttcgaaatcg ttatcttata tagttgaact | 240 |
| actacggtta aaaagcttaa gcctcagccc tcttaatcaa acttcttttt tgaaggcacc | 300 |
| agggtgcata aaagtgcgtc tattgttttcc cagtggaact ctgttgagat agcgatgttt | 360 |
| gttttttttt acttaacggc aaccaatacc gatagcgacg tcgctggcag tgtagagtgg | 420 |
| ccgtacggcg tcgctagatg gcacggcact aattgcggcg ggagtcgcta ggcggtgatg | 480 |
| catttccgca cagggaccag aggaagcttc ccaggcggtg acagtaagtg aactcattat | 540 |
| catgtcttct ccaaaacatt cgtgacatct agtcatgctc ctcgcaattc actccgattg | 600 |
| gtatagcttt ttcggtagtt ttagctacta tgcttagggg aaagaggaga aaccgtaccg | 660 |
| tcagtctcag tcaaaaaatt ttgatattca atctgatagc aaagttggaa cttggggtta | 720 |
| tctggccctt ttttgttatc atattcgtat acccaacaac atatcggttc caccggtcct | 780 |
| ttttatatat aaaagacgat gtgtagatgc actcgagtat tcttggagaa cgtgacttgt | 840 |
| attgagctag agtgctggat aaagtaccac atattaacgt tcttttatag agccaaacac | 900 |
| aattctttttg cactttcaac ataaggtaca actgaaaaca caggaaaaaa agaactaact | 960 |
| ctaagta | 967 |

<210> SEQ ID NO 95
<211> LENGTH: 1000
<212> TYPE: DNA
<213> ORGANISM: Saccharomyces cerevisiae
<220> FEATURE:
<221> NAME/KEY: misc_feature
<222> LOCATION: (1)..(1000)
<223> OTHER INFORMATION: Sc_TIR3 promoter

<400> SEQUENCE: 95

| gttcgaggcc aaacaaaaac cgcagcacaa tggagtaaaa gtcgaaggca cgggccccaa | 60 |
| acgatagagt ggaagttgta ggaaacaaaa gtggccgtct atgtggcgct tctctgcggt | 120 |
| gaattctgtg cgaagtgcct aaacgaaaac ggacggagaa ggctgcgggg ggatatccct | 180 |

| | |
|---|---|
| tgcataaagg atgcccggca ctgtcctaga cggtgccttc ccttagagac taggagagac | 240 |
| ttgagtagga gaaactgagc aggaaaattc gagagataaa gtacatgtgc ctaggtaagc | 300 |
| tgtacttcga acagctaata ttagtaagat gcataaaggg gcgtcaaagt ggaaatataa | 360 |
| cgacaggaga atctcggtgt gtaagttgga atgtgtattg caccacttcc atgattgggc | 420 |
| tttttttcctg gcgcaaaatg ttgcttttc aacatttttc ttatacgcag agagagaatc | 480 |
| gtcagatagg tggtaaaact tggagcctaa ttagctcatt atttcatttg aacgagacat | 540 |
| tggcttctgc cctacatcac ccatacgaga cattggcctt atacgaggcg tacttcgcct | 600 |
| tgcgggaaaa aaaatttctt ttgtaagcga ggttactcag aaactgtgac tgaaggcaga | 660 |
| ggttggaaac gtgtgtagac tccaaatgga acgataggaa cgtgtaccct accgcttctg | 720 |
| cacacgtttc ttagatatgc gtgccttaag gcgacccatt gttcctgttt accatgattt | 780 |
| ctgtaggctt ttttttagaa ggccctagaa tggattgcag atttccgtct gagaaggcag | 840 |
| tatacgtaca tatgaatata tatatacata tattctttgg tggagagtat aagcgtttcg | 900 |
| tctcctcttc ctttctctac tgcagatttt cttgctggtt gtttgatttt ttcttttttag | 960 |
| tgttccccag atccaattgt tcaaccgccc acacacaaca | 1000 |

<210> SEQ ID NO 96
<211> LENGTH: 1000
<212> TYPE: DNA
<213> ORGANISM: Saccharomyces cerevisiae
<220> FEATURE:
<221> NAME/KEY: misc_feature
<222> LOCATION: (1)..(1000)
<223> OTHER INFORMATION: Sc_TIR2 promoter

<400> SEQUENCE: 96

| | |
|---|---|
| aaacttaaaa caatccatta cctgcctagt ataatttttt tagaccagaa tatgactcca | 60 |
| taaaacgtga agcagcagct agaaaaacga cgcctcggcg gagtttgcgt ttaactctca | 120 |
| tgtgcggcca aacaggtgcg taagagctgt gactatttaa ttatgtaata tttacggaaa | 180 |
| aaggagtgga caaaaaaggc gtgaatttta ctccactggc ggtagccgcc tataaagaaa | 240 |
| ttgataagag gcgtgcctct tatgcgatct tcggaccaac aacaaagcac acaatagcgc | 300 |
| aaagtataca caatagagag cctgtaggaa agcagtgggg aatgtcttgg cttttttttat | 360 |
| gcccagaaaa aaataaacgt aacgttgggg aactacgcgc aatcatattt catgccctcc | 420 |
| ccacggtgct tagagcagcg cgttgcctac agaaacatct ttataaaatc ttggccggcc | 480 |
| aagattccca acgagactc acatttccca aaaaagacat ttctgtccaa agtagaagg | 540 |
| caagaaaacc ctggaggaat cataggcaaa gaaagaaaag aagaagttca tctttaaaac | 600 |
| taccttttcaa gcctttattc gttcctcgta aaggacacac gaaaaaaata aacagtacct | 660 |
| tgcagaagga gtgcagagtt aggtcgcagg gaatccttga aagccaagag tttttttttcc | 720 |
| gtaatgatct cccaaagcaa ccatcaacat tgtggtgcaa agtttagtgt aagatgttct | 780 |
| actgaactat cttaatagct gagcatcatg tgagtaaacg agtaagcaag aaaacaacaa | 840 |
| agtaatgttc aactttcgta actacggaaa ataatatata agtagttaac gaaattcgaa | 900 |
| caatgagagc tctcacatat catcttcttt tccagtttag ccattatcag cacaataata | 960 |
| caaaacacac tcgtacactc gcttcaacta taacaaaaaa | 1000 |

<210> SEQ ID NO 97
<211> LENGTH: 1000
<212> TYPE: DNA
<213> ORGANISM: Saccharomyces cerevisiae

```
<220> FEATURE:
<221> NAME/KEY: misc_feature
<222> LOCATION: (1)..(1000)
<223> OTHER INFORMATION: Sc_HEM13 promoter

<400> SEQUENCE: 97
aaaggtagaa ggtattgcac cgattcctag tatcaattct tttcaaaacc acttattttg      60
caaaacatgc gtctaacctg ccatttcagc aacgtaaata ataattactt ccatatatat     120
tcttctcccc cagtagcaat tttgacatga caaatttcag cgatagttgc ttcggcattc     180
gaaaatcgta gaagtatgtc ttaatgtaga aggttgagaa caaccggatc ttgcggtcat     240
tttttctttc gaggaaagtg caagtctgcc actttccaga aggcatagcc ttgccctttt     300
gttgatattt ctccccaccg taattgttgc attcgcgatc ttttcaacaa tacattttat     360
catcaagccc gcaaatcctc tggagtttgt cctctcgttc actgttggga aaaacaatac     420
gcctaattcg tgattaagat tcttcaaacc atttcctgcg gagtttttac tgtgtgttga     480
acggttcaca gcgtaaaaaa aagttactat aggcacggta ttttaatttc aattgtttag     540
aaagtgcctt cacaccatta gcccctggga ttaccgtcat aggcactttc tgctgagctc     600
ctgcgagatt tttgcgctga aagagtaaaa gaaatctttc acagcggctc cgcgggccct     660 tctacttta aacgagtcgc aggaacagaa gccaaatttc aaagaacgct acgctttcgc      720
cgtttctggt tctcccacca ataacgctcc agcttgaaca aagcataaga ctgcaaccaa     780
agcgctgacg gacgatccga agataaagct tgctttgccc attgttctcg tttcgaaagg     840
ctatataagg acacggattt ccttttttt ttccacctat tgtctttctt tgttaagctt      900
ttattctccg ggtttttttt ttgagcatat cgaaagcttt cttttcgcaa atcaaacata     960
gcaaaccgaa ctcttcgaac acaattaaat acacataaaa                          1000

<210> SEQ ID NO 98
<211> LENGTH: 1000
<212> TYPE: DNA
<213> ORGANISM: Saccharomyces cerevisiae
<220> FEATURE:
<221> NAME/KEY: misc_feature
<222> LOCATION: (1)..(1000)
<223> OTHER INFORMATION: Sc_YHK8 promoter

<400> SEQUENCE: 98
acagcggtac caagtgacac attgcgtact gtgtagtatg cgccgtatat aacttttttt      60
ttctgaaggt actttgaatt acaatctatt ttttacagtt cctatggcag gggttgaaga    120
tatttgggtc tgaaccatag caggattagt gttatagtag gtatgtgaat agaagctaac    180
aaaatgagat gaacctcata caaagtcgta gagaaaactg ctaacagaag agctgcgcct    240
tgaaatcgta tctctaagct tataataaat tgaaaggaaa aaatacgtgg taaatgcaag    300
cgaccaaaag gctacggccc aacgctaacc cgccgatagg tgcataatct aatttacctc    360
caccagcagg agcccttttt ctaagtaata agcaaaccag ataacttaca tcttgctgta    420
ggaaacaaaa gccggaataa tggttcactc atattcttcg tgtgaaacac agaagaaatc    480
caatatttgc ttcagtattt atctctaaaa attggtccta cattggaaac cataaaccaa    540
ttataaccgg tgtacgaatt gtaagctagt tctggaaatg tcatgttgcg caggtaaaag    600
tggagctgaa ttgtatatct gttttgatca ttattatccc tctgggtgag tggaaatatc    660
aataaaatgc aatggcacat ttaatatcct tctcttaatt ccgtgattta aacatcttg     720 atgccagaaa caccttttcgg atccggcaat aaagcggaga ttagcacgct tttcgccggt    780
```

| | | |
|---|---|---|
| cctacggatt tagtgttggc tattgttgag attagtaata cgcagagaat tttctaccg | 840 | |
| gtgaagcgac catctcagat tattaggtca agcaataaca cttgttatta gatgcgttac | 900 | |
| gttcacctgg accctatata aaggcatatt tgccttacat ttggtgtatg gtatcacctt | 960 | |
| gtatactaag aacatatata tgcagatata acaacaggat | 1000 | |

```
<210> SEQ ID NO 99
<211> LENGTH: 1000
<212> TYPE: DNA
<213> ORGANISM: Saccharomyces cerevisiae
<220> FEATURE:
<221> NAME/KEY: misc_feature
<222> LOCATION: (1)..(1000)
<223> OTHER INFORMATION: Sc_FET4 promoter

<400> SEQUENCE: 99
```

| | | |
|---|---|---|
| ctgtgcttgc tgttctaacc atacgtacta ctacgttgat tggattataa tgtcctttgg | 60 | |
| gtattctccg attacgttgt cccattttc ttttttgcct tgttgcgaag agcgttgttc | 120 | |
| cgaaaaccgg gtgcactttt tgttcacttt atatatccca cgaggagact gcgcgaacat | 180 | |
| gatatgtttg acctggcata gtgctattgt tcataaacaa taagccccct aaatacctgc | 240 | |
| atgtacgaag gtgtacgtac ggtcattcgc atttccctag cattactttc agtactggac | 300 | |
| aggttatttt taccctcta gtttgcgact accactaaat gggccatttt tacgtgtcta | 360 | |
| cgacatatcg caagggtttt tttcttttgt cttattcgag taattatata agcgcgcgta | 420 | |
| gtcatttttt tagcgacacc ctagggtcct gtagcagtaa tttgaggttt tcatggctcg | 480 | |
| aacaacgaca aaatattgag gaatcttgag ccttattggg gcgtaaatca cacaggtgtt | 540 | |
| gaatgagctt ggagcttgtg cggttatgta ttagatatgg gcagtttcct ttaacgttgg | 600 | |
| cgcctctttc tttcctaccc gtggggttgc tctcgaaact gattaggtca tgagcatttt | 660 | |
| tgctgagtct ttttaggaag cagcattttt ctcaaacgaa aaaaaaaaa accaaaaaaa | 720 | |
| aaaataaaga caaaaaaact atataatgct actggccttg aacttgcttg gtagaagcct | 780 | |
| tcttaattgc acccattagt ttagcatcta ccacatcttg attcgatgct cttcatttag | 840 | |
| aaatacttgt ttatataaat atacttcaca cggcatgaat taattgatag gtaagtaagt | 900 | |
| ttcttttatc ataagtcaaa cagtatcaga tataagaagg gaaaaggtag atatagaaac | 960 | |
| ctaataagac ccttattatt aaacattcgt taatcaaata | 1000 | |

```
<210> SEQ ID NO 100
<211> LENGTH: 1000
<212> TYPE: DNA
<213> ORGANISM: Saccharomyces cerevisiae
<220> FEATURE:
<221> NAME/KEY: misc_feature
<222> LOCATION: (1)..(1000)
<223> OTHER INFORMATION: Sc_TIR4 promoter

<400> SEQUENCE: 100
```

| | | |
|---|---|---|
| atgaagtaga cacgataaag ttcttgaaga aagattgtgg atgggtttgc tgaagcttag | 60 | |
| aactaagaaa agaaacaagc acgcgcaaga aaaccgctac ggctaacttc taaggtgagg | 120 | |
| atattgtgat tgtttatgcc tcatatttg ctttttatat gttcttcctt catacggcgt | 180 | |
| gcaaattatc cgccggcgaa cagggtgcta ttctaagagg aactttgaaa ctgtaaacgc | 240 | |
| ggtgtactga aggggtcatc tgaacgaaca atatttatg cttttgttag ccaaacggta | 300 | |
| ctgataaggg actgtgaaaa aaaaagacaa tgtatgggg tcacggtttc ccagattcgt | 360 | |
| gtgtgtgtaa taattcgttt acggcgcacg acagacactt caggaaattt aaagatcaga | 420 | |

```
ataggcatac actccacgca aggaaaacaa aagttgctac cgtaaccggc tcgtacgggg      480
aaagcaaggt catctagtgc tcacttacga actggcataa tcgagttgtg acttccaaac      540
ttaaccgtac tctcacagct gatgtgatcc gaagaaaacc ctgaagatac aacaatggca      600
accaaaggca acttaaaaag gcaaacgaag tactttcaa caatagctta cactgaaact       660
cgcggagagg cgacgctgcg cgcgaattat cagtaaaaat ctcgtaacaa cccatctgcc      720
acttttagaa ggaatggaaa ttctcaaaaa atgacgaaa ataatagaac agggttccta       780
aacgatgcat ttctaacaag taggatagtc caaagggag gatgcaaatt ctttgttttc       840
cacgcagtaa gatatgatcc caagctttcg aatataaaaa gggaaggatc gctaggacag      900
atcagttttt agcccgttta cttatctcgt tccctactct tgttctgata gaaaccagca      960
acaaaaacct attcactcgc ttattaatac cataaaaaaa                           1000
```

<210> SEQ ID NO 101
<211> LENGTH: 600
<212> TYPE: DNA
<213> ORGANISM: Saccharomyces cerevisiae
<220> FEATURE:
<221> NAME/KEY: misc_feature
<222> LOCATION: (1)..(600)
<223> OTHER INFORMATION: Sc_AAC3 promoter

<400> SEQUENCE: 101

```
gatgcctatc gtagtttgca aggaagacgg cttccaactg acaccgccct agtctggcag       60
gattcgtgaa aggagtccat gccagctgct acccagggat tgccacggcc ccggccagcg      120
tatagtacac tgtcaggagc aattcgaaga ggcaaccaaa attatgctaa gcatcgcact      180
ctctctcagt ctggtgctaa gcggaagaca tgcttccaat ggcctcctca ccgagaacgg      240
atattaaacg aaacgaagaa aaaaaatctt cacggaaaat gcgtaatgtc tggatgacaa      300
aatgcatggg tgtaaaaaag gaatgagac gaacttgtaa taaaccttag tggggttgacg     360 aattttgaaa taaagttttt ccttttttttt tttttttttc tttttcattg tttggttgcc      420
ttcaaattac atataagatt tctcgagaag ggttttccat tgtccttttc attaggcgtt      480
gaagtgaatc taaagtgcgc ttgaatgatt tcagatagaa agactaaaga agtggtgtga      540
gtataattaa ctcaattgaa gacggtttac ctgaagtgat atactgtgcc ttgagaaaca      600
```

<210> SEQ ID NO 102
<211> LENGTH: 300
<212> TYPE: DNA
<213> ORGANISM: Saccharomyces cerevisiae
<220> FEATURE:
<221> NAME/KEY: misc_feature
<222> LOCATION: (1)..(300)
<223> OTHER INFORMATION: Sc_PGK1 terminator

<400> SEQUENCE: 102

```
aattgaattg aattgaaatc gatagatcaa ttttttttctt ttctctttcc ccatcctttta     60 cgctaaaata atagtttatt ttatttttttg aatatttttt atttatatac gtatatatag      120
actattattt atcttttaat gattattaag attttttatta aaaaaaaatt cgctcctctt      180
ttaatgcctt tatgcagttt tttttttccca ttcgatattt ctatgttcgg gttcagcgta      240
ttttaagttt aataactcga aaattctgcg ttcgttaaag ctttcgagaa ggatattatt      300
```

<210> SEQ ID NO 103
<211> LENGTH: 36
<212> TYPE: DNA

<213> ORGANISM: Artificial Sequence
<220> FEATURE:
<223> OTHER INFORMATION: Oligononucleotide primer Fw-PRK (DBC-15631)

<400> SEQUENCE: 103
ccccggtctc gaatgtcaca acaacaaaca attgtg                                36

<210> SEQ ID NO 104
<211> LENGTH: 35
<212> TYPE: DNA
<213> ORGANISM: Artificial Sequence
<220> FEATURE:
<223> OTHER INFORMATION: Oligononucleotide primer Rv-PRK (DBC-15632)

<400> SEQUENCE: 104 gggggggtctc ctttaggctt tagcagctgt tgcag                                35

<210> SEQ ID NO 105
<211> LENGTH: 486
<212> TYPE: DNA
<213> ORGANISM: Artificial Sequence
<220> FEATURE:
<223> OTHER INFORMATION: gBLOCK bearing sequence of SNR52p-gRNA.INT1-
      SUP4t

<400> SEQUENCE: 105
ctgcagcccg gggatccac tagttctaga gcggccgcca ccgcccgcgg tctttgaaaa      60
gataatgtat gattatgctt tcactcatat ttatacagaa acttgatgtt ttctttcgag    120
tatatacaag gtgattacat gtacgtttga agtacaactc tagattttgt agtgccctct    180
tgggctagcg gtaaaggtgc gcattttttc acaccctaca atgttctgtt caaaagattt    240
tggtcaaacg ctgtagaagt gaaagttggt gcgcatgttt cggcgttcga aacttctccg    300
cagtgaaaga taaatgatct attagaacca gggaggtccg ttttagagct agaaatagca    360
agttaaaata aggctagtcc gttatcaact tgaaaaagtg gcaccgagtc ggtggtgctt    420
tttttgtttt ttatgtctcc gcggcaatta accctcacta aagggaacaa aagctggagc    480
tccacc                                                                486

<210> SEQ ID NO 106
<211> LENGTH: 5949
<212> TYPE: DNA
<213> ORGANISM: Artificial Sequence
<220> FEATURE:
<223> OTHER INFORMATION: pRN599

<400> SEQUENCE: 106
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatcga ctacgtcgta aggccgtttc tgacagagta aaattcttga gggaactttc    240
accattatgg gaaatggttc aagaaggtat tgacttaaac tccatcaaat ggtcaggtca    300
ttgagtgttt tttatttgtt gtattttttt tttttagag aaaatcctcc aatatcaaat    360
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tcctttttct ccttcttgat aaatgtatgt    540
agattgcgta tatagtttcg tctaccctat gaacatattc catttgtaa tttcgtgtcg    600

```
tttctattat gaatttcatt tataaagttt atgtacacct aggatccgtc gacactggat    660
ggcggcgtta gtatcgaatc gacagcagta tagcgaccag cattcacata cgattgacgc    720
atgatattac tttctgcgca cttaacttcg catctgggca gatgatgtcg aggcgaaaaa    780
aaatataaat cacgctaaca tttgattaaa atagaacaac tacaatataa aaaaactata    840
caaatgacaa gttcttgaaa acaagaatct ttttattgtc agtactgatt agaaaaactc    900
atcgagcatc aaatgaaact gcaatttatt catatcagga ttatcaatac catattttg     960
aaaaagccgt ttctgtaatg aaggagaaaa ctcaccgagg cagttccata ggatggcaag   1020
atcctggtat cggtctgcga ttccgactcg tccaacatca atacaaccta ttaatttccc   1080
ctcgtcaaaa ataaggttat caagtgagaa atcaccatga gtgacgactg aatccggtga   1140
gaatggcaaa agcttatgca tttctttcca gacttgttca acaggccagc cattacgctc   1200
gtcatcaaaa tcactcgcat caaccaaacc gttattcatt cgtgattgcg cctgagcgag   1260
acgaaatacg cgatcgctgt taaaaggaca attacaaaca ggaatcgaat gcaaccggcg   1320
caggaacact gccagcgcat caacaatatt ttcacctgaa tcaggatatt cttctaatac   1380
ctggaatgct gttttgccgg ggatcgcagt ggtgagtaac catgcatcat caggagtacg   1440
gataaaatgc ttgatggtcg gaagaggcat aaattccgtc agccagttta gtctgaccat   1500
ctcatctgta acatcattgg caacgctacc tttgccatgt ttcagaaaca actctggcgc   1560
atcgggcttc ccatacaatc gatagattgt cgcacctgat gcccgacat tatcgcgagc    1620
ccatttatac ccatataaat cagcatccat gttggaattt aatcgcggcc tcgaaacgtg   1680
agtcttttcc ttacccatgg ttgtttatgt tcggatgtga tgtgagaact gtatcctagc   1740
aagattttaa aaggaagtat atgaaagaag aacctcagtg gcaaatccta acctttata    1800
tttctctaca ggggcgcggc gtggggacaa ttcaacgcgt ctgtgagggg agcgtttccc   1860
tgctcgcagg tctgcagcga ggagccgtaa tttttgcttc gcgccgtgcg gccatcaaaa   1920
tgtatggatg caaatgatta tacatgggga tgtatgggct aaatgtacgg gcgacagtca   1980
catcatgccc ctgagctgcg cacgtcaaga ctgtcaagga gggtattctg gcctccatg    2040
tcgctggccg ggtgacccgg cggggacgag gccttaagtt cgaacgtacg agctccggca   2100
ttgcgaatac cgctttccac aaacattgct caaaagtatc tctttgctat atatctctgt   2160
gctatatccc tatataacct acccatccac ctttcgctcc ttgaacttgc atctaaactc   2220
gacctctaca ttttttatgt ttatctctag tattactctt tagacaaaaa aattgtagta   2280
agaactattc atagagtgaa tcgaaaacaa tacgaaaatg taaacatttc ctatacgtag   2340
tatatagaga caaaatagaa gaaaccgttc ataatttcct gaccaatgaa gaatcatcaa   2400
cgctatcact ttctgttcac aaagtatgcg caatccacat cggtatagaa tataatcggg   2460
gatgcctta tcttgaaaaa atgcacccgc agcttcgcta gtaatcagta aacgcgggaa    2520
gtggagtcag gcttttttta tggaagagaa aatagacacc aaagtagcct tcttctaacc   2580
ttaacggacc tacagtgcaa aaagttatca agagactgca ttatagagcg cacaaaggag   2640
aaaaaaagta atctaagatg ctttgttaga aaatagcgc tctcgggatg cattttgta    2700
gaacaaaaaa gaagtataga ttctttgttg gtaaaatagc gctctcgcgt tgcatttctg   2760
ttctgtaaaa atgcagctca gattctttgt ttgaaaaatt agcgctctcg cgttgcattt   2820
tgttttaca aaaatgaagc acagattctt cgttggtaaa atagcgcttt cgcgttgcat    2880
ttctgttctg taaaaatgca gctcagattc tttgtttgaa aaattagcgc tctcgcgttg   2940
catttttgtt ctacaaaatg aagcacagat gcttcgttaa caaagatatg ctattgaagt   3000
```

```
gcaagatgga aacgcagaaa atgaaccggg gatgcgacgt gcaagattac ctatgcaata    3060
gatgcaatag tttctccagg aaccgaaata catacattgt cttccgtaaa gcgctagact    3120
atatattatt atacaggttc aaatatacta tctgtttcag ggaaaactcc caggttcgga    3180
tgttcaaaat tcaatgatgg gtaacaagta cgatcgtaaa tctgtaaaac agtttgtcgg    3240
atattaggct gtatctcctc aaagcgtatt cgaatatcat tgagaagctg cagcgtcaca    3300
tcggataata atgatggcag ccattgtaga agtgcctttt gcatttctag tctctttctc    3360
ggtctagcta gttttactac atcgcgaaga tagaatctta gatcacactg cctttgctga    3420
gctggatcaa tagagtaaca aaagagtggt aaggcctcgt taaggacaa ggacctgagc     3480 ggaagtgtat cgtacagtag acggagtata ctaggtatag tctatagtcc gtggaattaa    3540
ttctcatgtt tgacagctta tcatcgataa tccggagcta gcatgcggcc gctctagaac    3600
tagtggatcc cccgggctgc aggaattcga tatcaagctt atcgataccg tcgacctcga    3660
gggggggccc ggtacccagc ttttgttccc tttagtgagg gttaattccg agcttggcgt    3720
aatcatggtc atagctgttt cctgtgtgaa attgttatcc gctcacaatt ccacacaaca    3780
taggagccgg aagcataaag tgtaaagcct ggggtgccta atgagtgagg taactcacat    3840
taattgcgtt gcgctcactg cccgctttcc agtcgggaaa cctgtcgtgc cagctgcatt    3900
aatgaatcgg ccaacgcgcg gggagaggcg gtttgcgtat tgggcgctct tccgcttcct    3960
cgctcactga ctcgctgcgc tcggtcgttc ggctgcggcg agcggtatca gctcactcaa    4020
aggcggtaat acggttatcc acagaatcag gggataacgc aggaaagaac atgtgagcaa    4080
aaggccagca aaaggccagg aaccgtaaaa aggccgcgtt gctggcgttt ttccataggc    4140
tcggcccccc tgacgagcat cacaaaaatc gacgctcaag tcagaggtgg cgaaacccga    4200
caggactata aagataccag gcgttccccc ctggaagctc cctcgtgcgc tctcctgttc    4260
cgaccctgcc gcttaccgga tacctgtccg cctttctccc ttcgggaagc gtggcgcttt    4320
ctcaatgctc acgctgtagg tatctcagtt cggtgtaggt cgttcgctcc aagctgggct    4380
gtgtgcacga accccccgtt cagcccgacc gctgcgcctt atccggtaac tatcgtcttg    4440
agtccaaccc ggtaagacac gacttatcgc cactggcagc agccactggt aacaggatta    4500
gcagagcgag gtatgtaggc ggtgctacag agttcttgaa gtggtggcct aactacggct    4560
acactagaag gacagtattt ggtatctgcg ctctgctgaa gccagttacc ttcggaaaaa    4620
gagttggtag ctcttgatcc ggcaaacaaa ccaccgctgg tagcggtggt ttttttgttt    4680
gcaagcagca gattacgcgc agaaaaaaag gatctcaaga agatcctttg atcttttcta    4740
cggggtctga cgctcagtgg aacgaaaact cacgttaagg gattttggtc atgagattat    4800
caaaaaggat cttcacctag atcctttaa attaaaaatg aagttttaa tcaatctaaa      4860 gtatatatga gtaaacttgg tctgacagtt accaatgctt aatcagtgag gcacctatct    4920
cagcgatctg tctatttcgt tcatccatag ttgcctgact gcccgtcgtg tagataacta    4980
cgatacggga gggcttacca tctggcccca gtgctgcaat gataccgcga gacccacgct    5040
caccggctcc agatttatca gcaataaacc agccagccgg aagggccgag cgcagaagtg    5100
gtcctgcaac tttatccgcc tccatccagt ctattaattg ttgccgggaa gctagagtaa    5160
gtagttcgcc agttaatagt ttgcgcaacg ttgttgccat tgctacaggc atcgtggtgt    5220
cacgctcgtc gtttggtatg gcttcattca gctccggttc ccaacgatca aggcgagtta    5280
catgatcccc catgttgtga aaaaagcgg ttagctcctt cggtcctccg atcgttgtca     5340
```

-continued

```
gaagtaagtt ggccgcagtg ttatcactca tggttatggc agcactgcat aattctctta    5400
ctgtcatgcc atccgtaaga tgcttttctg tgactggtga gtactcaacc aagtcattct    5460
gagaatagtg tatgcggcga ccgagttgct cttgcccggc gtcaatacgg gataataccg    5520
cgccacatag cagaacttta aaagtgctca tcattggaaa acgttcttcg ggcgaaaac     5580 tctcaaggat cttaccgctg ttgagatcca gttcgatgta acccactcgt gcacccaact    5640
gatcttcagc atcttttact ttccaccagcg tttctgggtg agcaaaaaca ggaaggcaaa   5700
atgccgcaaa aaagggaata agggcgacac ggaaatgttg aatactcata ctcttccttt    5760
ttcaatatta ttgaagcatt tatcagggtt attgtctcat gagcggatac atatttgaat    5820
gtatttagaa aaataaacaa ataggggttc cgcgcacatt tccccgaaaa gtgccacctg    5880
acgtctaaga aaccattatt atcatgacat aacctataa aaataggcgt atcacgaggc     5940
cctttcgtc                                                            5949
```

<210> SEQ ID NO 107
<211> LENGTH: 19
<212> TYPE: DNA
<213> ORGANISM: Artificial Sequence
<220> FEATURE:
<223> OTHER INFORMATION: Forward primer INT1-5'flank (BOZ-783)

<400> SEQUENCE: 107

```
cggcattatt gtgtatggc                                                 19
```

<210> SEQ ID NO 108
<211> LENGTH: 72
<212> TYPE: DNA
<213> ORGANISM: Artificial Sequence
<220> FEATURE:
<223> OTHER INFORMATION: reverse primer INT1-5 'flank with connector c
    (DBC-19944)

<400> SEQUENCE: 108

```
caacaggagg cggatggata tactgtggtc tggaagatgc cggaaagcgt catgttatgc    60
tcctcaatca cg                                                        72
```

<210> SEQ ID NO 109
<211> LENGTH: 21
<212> TYPE: DNA
<213> ORGANISM: Artificial Sequence
<220> FEATURE:
<223> OTHER INFORMATION: forward primer connector c to amplify anaerobic
    promoter-PRK-PGK1 terminator expression cassette (DBC-5799)

<400> SEQUENCE: 109

```
acgctttccg gcatcttcca g                                              21
```

<210> SEQ ID NO 110
<211> LENGTH: 20
<212> TYPE: DNA
<213> ORGANISM: Artificial Sequence
<220> FEATURE:
<223> OTHER INFORMATION: reverse primer connector d to amplify PRK
    expression cassette (DBC-5800)

<400> SEQUENCE: 110

```
gcggaatatt ggcggaacgg                                                20
```

<210> SEQ ID NO 111
<211> LENGTH: 74
<212> TYPE: DNA

```
<213> ORGANISM: Artificial Sequence
<220> FEATURE:
<223> OTHER INFORMATION: forward primer to amplify URA3 marker with
      flank connector d (DBC-19947)

<400> SEQUENCE: 111
aacgttgtcc aggtttgtat ccacgtgtgt ccgttccgcc aatattccgc gctgtggttt    60
cagggtccat aaag                                                     74

<210> SEQ ID NO 112
<211> LENGTH: 72
<212> TYPE: DNA
<213> ORGANISM: Artificial Sequence
<220> FEATURE:
<223> OTHER INFORMATION: reverse primer to amplify URA3 locus with flank
      connector e (DBC-19949)

<400> SEQUENCE: 112
aggtacaaca agcacgaccg agcatatggg aaggatgttt gtggttattt cgagattccc    60
gggtaataac tg                                                       72

<210> SEQ ID NO 113
<211> LENGTH: 20
<212> TYPE: DNA
<213> ORGANISM: Artificial Sequence
<220> FEATURE:
<223> OTHER INFORMATION: forward primer INT1-3'flank with connector d
      (DBC-19946)

<400> SEQUENCE: 113
aactccatca aatggtcagg                                               20

<210> SEQ ID NO 114
<211> LENGTH: 20
<212> TYPE: DNA
<213> ORGANISM: Artificial Sequence
<220> FEATURE:
<223> OTHER INFORMATION: reverse primer INT1-3 'flank (BoZ-788)

<400> SEQUENCE: 114
aacaaaagct gggtaccggg                                               20

<210> SEQ ID NO 115
<211> LENGTH: 73
<212> TYPE: DNA
<213> ORGANISM: Artificial Sequence
<220> FEATURE:
<223> OTHER INFORMATION: forward primer on backbone pRN599 (DBC-13775)

<400> SEQUENCE: 115
cttatcgata ccgtcgacct cgagggggggg cccggtaccc agcttttgtt ccgcggtctt   60
tgaaaagata atg                                                      73

<210> SEQ ID NO 116
<211> LENGTH: 69
<212> TYPE: DNA
<213> ORGANISM: Artificial Sequence
<220> FEATURE:
<223> OTHER INFORMATION: reverse primer on backbone pRN599 (DBC-13776)

<400> SEQUENCE: 116
aaaatacaac aaataaaaaa cactcaatga cctgaccatt tgatggagtt ccgcggagac    60
ataaaaaac                                                           69
```

<210> SEQ ID NO 117
<211> LENGTH: 73
<212> TYPE: DNA
<213> ORGANISM: Artificial Sequence
<220> FEATURE:
<223> OTHER INFORMATION: forward primer on gRNA cassette INT1
      (DBC-13773)

<400> SEQUENCE: 117
cttatcgata ccgtcgacct cgaggggggg cccggtaccc agcttttgtt ccgcggtctt    60
tgaaaagata atg                                                      73

<210> SEQ ID NO 118
<211> LENGTH: 69
<212> TYPE: DNA
<213> ORGANISM: Artificial Sequence
<220> FEATURE:
<223> OTHER INFORMATION: reverse primer on gRNa cassette INT1
      (DBC-13774)

<400> SEQUENCE: 118
aaaatacaac aaataaaaaa cactcaatga cctgaccatt tgatggagtt ccgcggagac    60
ataaaaaac                                                           69

<210> SEQ ID NO 119
<211> LENGTH: 82
<212> TYPE: DNA
<213> ORGANISM: Artificial Sequence
<220> FEATURE:
<223> OTHER INFORMATION: forward primer 7933 YEN1p prk cassette
      construction

<400> SEQUENCE: 119
tcacagaggg atcccgttac ccatctatgc tgaagattta tcatactatt cctccgctcg    60
ggaattcaag caatagcgtt tc                                            82

<210> SEQ ID NO 120
<211> LENGTH: 12
<212> TYPE: DNA
<213> ORGANISM: Artificial Sequence
<220> FEATURE:
<223> OTHER INFORMATION: PRK promoter motif
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 120
nnnattgttn nn                                                       12

<210> SEQ ID NO 121
<211> LENGTH: 8
<212> TYPE: DNA
<213> ORGANISM: Artificial Sequence
<220> FEATURE:
<223> OTHER INFORMATION: PRK promoter motif

<400> SEQUENCE: 121 tcgttyag                                                             8

<210> SEQ ID NO 122

```
<211> LENGTH: 12
<212> TYPE: DNA
<213> ORGANISM: Artificial Sequence
<220> FEATURE:
<223> OTHER INFORMATION: PRK promoter motif

<400> SEQUENCE: 122
aaaaattgtt ga                                                          12

<210> SEQ ID NO 123
<211> LENGTH: 11
<212> TYPE: DNA
<213> ORGANISM: Artificial Sequence
<220> FEATURE:
<223> OTHER INFORMATION: PRK promoter motif

<400> SEQUENCE: 123
aaaaattgtt g                                                           11
```